(12) United States Patent
Rueckle et al.

(10) Patent No.: US 7,846,925 B2
(45) Date of Patent: Dec. 7, 2010

(54) AZOLIDINONE-VINYL FUSED-BENZENE DERIVATIVES

(75) Inventors: Thomas Rueckle, Plan-les-Ouates (CH); Xuliang Jiang, Braintree, MA (US); Pascale Gaillard, Saint-Julien-en-genevois (FR); Dennis Church, Commugny (CH); Tania Grippi Vallotton, Corsier (CH)

(73) Assignee: Merck Serono SA, Coinsins (CH)

( * ) Notice: Subject to any disclaimer, the term of this patent is extended or adjusted under 35 U.S.C. 154(b) by 231 days.

(21) Appl. No.: 10/520,621

(22) PCT Filed: Jul. 10, 2003

(86) PCT No.: PCT/EP03/50302

§ 371 (c)(1),
(2), (4) Date: Aug. 24, 2005

(87) PCT Pub. No.: WO2004/007491

PCT Pub. Date: Jan. 22, 2004

(65) Prior Publication Data

US 2006/0122176 A1    Jun. 8, 2006

Related U.S. Application Data

(63) Continuation-in-part of application No. 10/289,998, filed on Nov. 7, 2002, now abandoned.

(30) Foreign Application Priority Data

Jul. 10, 2002   (EP)   .................. 02100798

(51) Int. Cl.
| | | |
|---|---|---|
| A61K 31/536 | (2006.01) | |
| A61K 31/53 | (2006.01) | |
| A61K 31/498 | (2006.01) | |
| A61K 31/517 | (2006.01) | |
| A61K 31/4709 | (2006.01) | |
| A61K 31/427 | (2006.01) | |
| A61K 31/423 | (2006.01) | |
| A61K 31/4184 | (2006.01) | |
| A61K 31/343 | (2006.01) | |
| A61K 31/352 | (2006.01) | |
| C07D 265/36 | (2006.01) | |
| C07D 253/08 | (2006.01) | |
| C07D 417/02 | (2006.01) | |
| C07D 241/36 | (2006.01) | |
| C07D 215/38 | (2006.01) | |
| C07D 277/32 | (2006.01) | |
| C07D 261/20 | (2006.01) | |
| C07D 235/04 | (2006.01) | |
| C07D 319/16 | (2006.01) | |
| C07D 317/46 | (2006.01) | |
| C07D 307/78 | (2006.01) | |

(52) U.S. Cl. ............... 514/230.5; 514/243; 514/249; 514/266.2; 514/314; 514/369; 514/379; 514/394; 514/452; 514/465; 514/469; 544/105; 544/183; 544/284; 544/353; 546/169; 548/183; 548/241; 548/304.7; 549/366; 549/435; 549/467

(58) Field of Classification Search ............... 514/230.5, 514/243, 249, 266.2, 314, 369, 379, 394, 514/452, 465, 469; 544/105, 183, 284, 353; 546/169; 548/183, 241, 304.7; 549/366, 549/435, 467

See application file for complete search history.

(56) References Cited

FOREIGN PATENT DOCUMENTS

| | | |
|---|---|---|
| EP | 0 283 036 | 9/1988 |
| JP | 55-36429 | 3/1980 |
| JP | 55-45648 | 3/1980 |
| JP | 2000095770 A * | 4/2000 |
| WO | 02/051409 | 7/2002 |

OTHER PUBLICATIONS

Prabhakar et al. "Synthesis and biological activity of novel thiazolidinediones" Bioorganic & Medicinal Chemistry Letters, 1998, vol. 8, Iss 6, pp. 2725-2730.*

Janusz, John M. et al. "New Cyclooxygenase-2/5-Lipoxygenase Inhibitors. 3.7-tert-Butyl-2,3-dihydro-3,3-dimethylbenzofuran Derivates as Gastrointestinal Safe Antiinflammatory and Analgesic Agents: Variations at the 5 Position", J. Med. Chem., vol. 41, No. 18, pp. 3515-3529, XP002223203 1998.

Brummond, Kay M. et al. "Solid-Phase Synthesis of BRL 49653", J. Org. Chem., vol. 64, pp. 1723-1726 1999.

Cha, Jin Soon et al. "Exceptionally Facile Reduction of Acid Chlorides to Aldehydes by Sodium Tri-tert-butoxyaluminohydride", J. Org. Chem., vol. 58, pp. 4732-4734 1993.

(Continued)

*Primary Examiner*—Joseph R Kosack
(74) *Attorney, Agent, or Firm*—Oblon, Spivak, McClelland, Maier & Neustadt, L.L.P.

(57) ABSTRACT

The present invention is related to azolidinedione-vinyl fused-benzene derivatives of formula (I) for the treatment and/or prophylaxis of autoimmune disorders and/or inflammatory diseases, cardiovascular diseases, neurodegenerative diseases, bacterial or viral infections, kidney diseases, platelet aggregation, cancer, graft rejection or lung injuries. Formula (I), wherein A, X, Y, Z, $R^1$, $R^2$ and n are as described in the description.

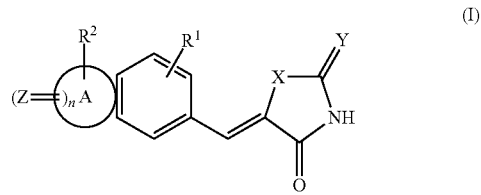

(I)

25 Claims, No Drawings

OTHER PUBLICATIONS

Fraser, James D. et al. "Regulation of Interleukin-2 Gene Enhancer Activity by the T Cell Accessory Molecule CD28", Science, vol. 251, pp. 313-316 1991.
Fruman, David A. et al. "Phosphoinositide Kinases", Annu. Rev. Biochem., vol. 67, pp. 481-507 1998.
Gerard, Craig et al. "Chemokines and Disease", Nature Immunology, vol. 2, No. 2, pp. 108-115 2001.
Hirsch, Emilio et al. "Resistance to thromboembolism in PI3Kgamma-deficient mice", The FASEB Journal, vol. 15, No. 11, pp. 2019-2021 2001.
Hirsch, Emilio et al. "Central Role for G Protein-Coupled Phosphoinositide 3-Kinase gamma in inflammation", Science, vol. 287, No. 5455, pp. 1049-1053 2000.
Katso, Roy et al. "Cellular Function of Phosphoinositide 3-Kinases: Implications for Development, Immunity, Homeostasis, and Cancer", Annu. Rev. Cell Dev. Biol, vol. 17, pp. 615-675 2001.
Laffargue, Muriel et al. "Phosphoinositide 3-Kinase gamma Is an Essential Amplifier of Mast Cell Function", Immunity, vol. 16, No. 3, pp. 441-451 2002.
Lawlor, Margaret A. et al. "PKB/Akt: a key mediator of cell proliferation, survival and insulin responses?", Journal of Cell Science, vol. 114, No. 16, pp. 2903-2910 2001.
Leslie, Nick R. et al. "Phosphoinositide-Regulated Kinases and Phosphoinositide Phosphatases", Chem. Rev., vol. 101, No. 8, pp. 2365-2380 2001.
Lopez-Ilasaca, Marco et al. "Phosphoinositide 3-Kinase gamma Is a Mediator of Gbetagamma-dependent Jun Kinase Activation", The Journal of Biological Chemistry, vol. 273, No. 5, pp. 2505-2508 1998.
Panayotou, George et al. "Phosphatidyl-inositol 3-Kinase: a key enzyme in diverse signalling processes", Trends in Cell Biology, vol. 2, pp. 358-360 1992.
Parker, Peter J. "PI 3-kinase puts GTP on the Rac", Current Biology, vol. 5, No. 6, pp. 577-579 1995.
Petrov, Ognyan et al. "C-Formylation of some 2(3H)-Benzazolones and 2H-1,4-Benzoxazin-3(4H)-One", Collect. Czech. Chem. Commun., vol. 62, pp. 494-497 1997.
Pages, Francoise et al. "Binding of phosphatidyl-inositol-3-OH kinase to CD28 is required for T-cell signalling", Nature, vol. 369, pp. 327-329 1994.
Rudd, Christopher E. "Upstream-Downstream: CD28 Cosignaling Pathways and T Cell Function", Immunity, vol. 4, pp. 527-534 1996.
Stephens, Len et al. "Roles of PI3Ks in leukocyte chemotaxis and phagocytosis", Curr. Opinion Cell Biol., vol. 14, No. 2, pp. 203-213 2002.
Stein, Robert C. et al. "PI3-kinase inhibition: a target for drug development?", Molecular Medicine Today, vol. 6, No. 9, pp. 347-357 2000.
Thelen, Marcus et al. "Wortmannin binds specifically to 1-phosphatidylinositol 3-kinase while inhibiting guanine nucleotide-binding protein-coupled receptor signaling in neutrophil leukocytes", Proc. Natl. Acad. Sci., vol. 91, pp. 4960-4964 1994.
Toker, A. "Phosphoinositides and signal transduction", Cell. Mol. Life Sci., vol. 59, No. 5, pp. 761-779 2002.
Vanhaesebroeck, B. et al. "Signaling by Distinct Classes of Phosphoinositide 3-Kinases", Experimental Cell Research, vol. 253, vol. 1, pp. 239-254 1999.
Vanhaesebroeck, Bart et al. "Phosphoinositide 3-kinases: a conserved family of signal transducers", TIBS, vol. 22, No. 7, pp. 267-272 1997.
Wymann, Matthias P. et al. "Lipids on the move: phosphoinositide 3-kinases in leukocyte function", Immunology Today, vol. 21, No. 6, pp. 260-264 2000.
Yao, Ryoji et al. "Requirement for Phosphatidylinositol-3 Kinase in the Prevention of Apoptosis by Nerve Growth Factor", Science, vol. 267, pp. 2003-2005 1995.
Hirsch et at. The Faseb Journal vol. 15 Sep. 2001, 2019-2021.
Brennan et at. Oncogene 2002, 21, 1263-1 271.
Martin, et al. Journal of Biological Chemistry, vol. 276, No. 19, Issue of May 11, 2001, pp. 15840-1 5849.
Johnson et al. Proc. Natl. Acad. Sci, U.S.A. vol. 94, pp. 3052-3057. Apr. 1997.
Benjamin et al. Journal of Virology. Apr. 1998, pp. 3221-3226.
Chock et al. PNAS, Jun. 20, 2000, vol. 97, No. 13, 71 18-7123.
Hirai et al. Oncogene 1997, 14, 3067-3072.
Kita et al. FEBS Letters 441(1998) 63-66.
Bierer et al. Proc. Natl. Acad. Sci., USA vol. 92, pp. 8808-881 2. Sep. 1995.
Downey et at. Microbes and Infection 5 (2003), 1293-1 298.
Yano et at Biochem. J. 1995, 312, 145-1 50.
Nienaber et al. *The Journal of Clinical Investigation* Oct. 2003 vol. 112 No. 7, 1067-1079.
Wymann et at. Biochemical Society Transactions (2003) vol. 31 Part 1, 275-280.
Plevin et al. Biochem. J. 1996, 318, pp. 965-971.
Roche et at. *Oncogene* 2000, 19, 5083-5090.
Sawyers et al. *Nature Review Cancer* vol. 2 Jul. 2002, 489-501.
Thelen et al.Thel Biochemical and Biophysical Research Communications, vol. 217, No. 3, 1995, pp. 1255-1262.
Vogt et al. PNAS, Feb. 15, 2000, vol. 97, No. 4, 1749-1 753.
Ward et at. *Trends in Molecular Medecine* vol. 7, No10. Oct. 2001, pp. 455-462.
Weaver et at, *Gastroenterology* 2001, 120, 1117-1127.
Weinstein et at. Journal of Leucocyte Biology vol. 67, Mar. 2000, 405-414.
Sheng et at. Gut 2003 52: 1472-1478.

* cited by examiner

AZOLIDINONE-VINYL FUSED-BENZENE DERIVATIVES

FIELD OF THE INVENTION

This present invention is related to the use of azolidinone-vinyl fused-benzene derivatives of formula (I) for the treatment and/or prophylaxis of autoimmune disorders and/or inflammatory diseases, cardiovascular diseases, neurodegenerative diseases, bacterial or viral infections, kidney diseases, platelet aggregation, cancer, graft rejection or lung injuries. Specifically, the present invention is related to substituted azolidinone-vinyl fused-benzene derivatives for the modulation, notably the inhibition of the activity or function of the phospho-inositide-3'OH kinase family, PI3K, particularly of the PI3Kγ.

BACKGROUND OF THE INVENTION

Cellular plasma membranes can be viewed as a large store of second messenger that can be enlisted in a variety of signal transduction pathways. As regards function and regulation of effector enzymes in phospholipid signalling pathways, these enzymes generate second messengers from the membrane phospholipid pool (class I PI3 kinases (e.g. PI3Kgamma)) are dual-specific kinase enzymes, means they display both: lipid kinase (phosphorylation of phospho-inositides) as well as protein kinase activity, shown to be capable of phosphorylation of other protein substrates, including auto-phosphorylation as intra-molecular regulatory mechanism. These enzymes of phospholipid signalling are activated in response to a variety of extra-cellular signals such as growth factors, mitogens, integrins (cell-cell interactions) hormones, cytokines, viruses and neurotransmitters such as described in Scheme 1 hereinafter and also by intra-cellular cross regulation by other signaling molecules (cross-talk, where the original signal can activate some parallel pathways that in a second step transmit signals to PI3Ks by intra-cellular signaling events), such as small GTPasesu, kinases or phosphatases for example.

The inositol phospholipids (phosphoinositides) intracellular signalling pathway begins with binding of a signalling molecule (extracellular ligands, stimuli, receptor dimerization, transactivation by heterologous receptor (e.g. receptor tyrosine kinase)) to a G-protein linked transmembrane receptor integrated into the plasma membrane.

PI3K converts the membrane phospholipid PIP(4,5)2 into PIP(3,4,5)3 which in turn can be further converted into another 3' phosphorylated form of phosphoinositides by 5'-specific phospho-inositide phosphatases, thus PI3K enzymatic activity results either directly or indirectly in the generation of two 3'-phosphoinositide subtypes that function as $2^{nd}$ messengers in intra-cellular signal transduction (*Trends Biochem Sci.* 22(7) p. 267-72 (1997) by Vanhaesebroeck B et al., *Chem Rev.* 101(8) p. 2365-80 (2001) by Leslie N. R et al (2001); *Annu Rev Cell Dev Biol.* 17 p. 615-75 (2001) by Katso R. et al. and *Cell Mol Life Sci.* 59(5) p. 761-79 (2002) by Toker a. et al.). Multiple PI3K isoforms categorized by their catalytic subunits, their regulation by corresponding regulatory subunits, expression patterns and signaling-specific functions (p110α, β, δ, and γ) perform this enzymatic reaction (*Exp Cell Res.* 25(1) p. 239-54 (1999) by Vanhaesebroeck B. and *Annu Rev Cell Dev Biol.* 17 p. 615-75 (2001) by Katso R. et al).

The evolutionary conserved isoforms p110α and β are ubiquitously expressed, while δ and γ are more specifically expressed in the haematopoietic cell system, smooth muscle cells, myocytes and endothelial cells (*Trends Biochem Sci.* 22(7) p. 267-72 (1997) by Vanhaesebroeck B et al.). Their expression might also be regulated in an inducible manner depending on the cellular-, tissue type and stimuli as well as disease context. To date, eight mammalian PI3Ks have been identified, divided into three main classes (I, II, and III) on the basis of sequence homology, structure, binding partners, mode of activation, and substrate preference in vitro. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI (*Trends Biochem Sci.* 22(7) p. 267-72 (1997) by Vanhaesebroeck B et al, *Exp Cell Res.* 25(1) p. 239-54 (1999) by Vanhaesebroeck B. and *Chem Rev.* 101(8) p. 2365-80 (2001) by Leslie N. R et al (2001)) G-protein coupled receptors mediated phosphoinositide 3'OH-kinase activation via small GTPases such as Gβγ and Ras, and consequently PI3K signaling plays a central role in establishing and coordinating cell polarity and dynamic organization of the cytoskeleton—which together provides the driving force of cells to move.

Scheme 1

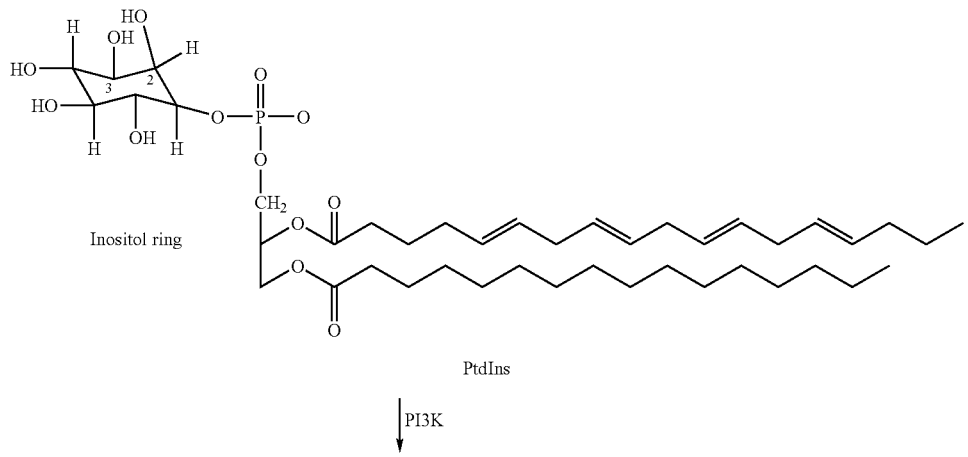

Inositol ring

PtdIns

PI3K

-continued

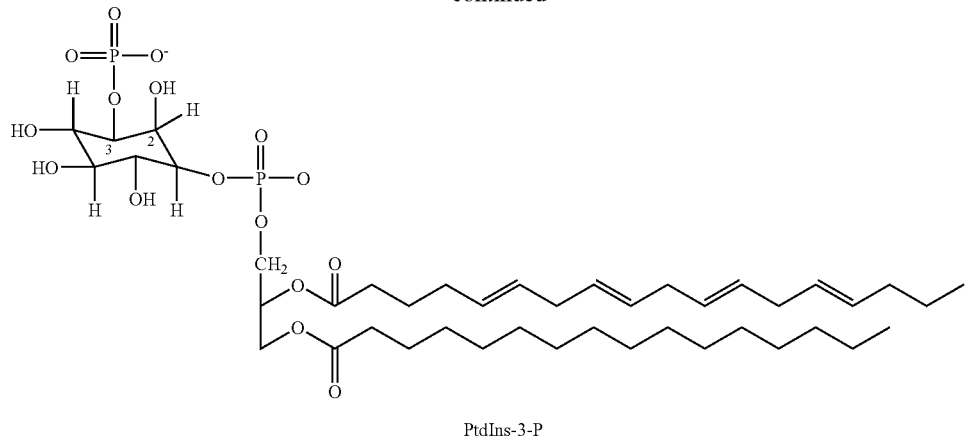

PtdIns-3-P

As above illustrated in Scheme 1, Phosphoinositide 3-kinase (PI3K) is involved in the phosphorylation of Phosphatidylinositol (PtdIns) on the third carbon of the inositol ring. The phosphorylation of PtdIns to 3,4,5-triphosphate (PtdIns (3,4,5)$P_3$), PtdIns(3,4)$P_2$ and PtdIns(3)P act as second messengers for a variety of signal transduction pathways, including those essential to cell proliferation, cell differentiation, cell growth, cell size, cell survival, apoptosis, adhesion, cell motility, cell migration, chemotaxis, invasion, cytoskeletal rearrangement, cell shape changes, vesicle trafficking and metabolic pathway (*Annu Rev Cell Dev Biol.* 17 p. 615-75 (2001) by Katso et al. and *Mol Med Today* 6(9) p. 347-57 (2000) by Stein R. C). Chemotaxis—the directed movement of cells toward a concentration gradient of chemical attractants, also called chemokines is involved in many important diseases such as inflammation/auto-immunity, neurodegeneration, angiogenesis, invasion/metastisis and wound healing (*Immunol Today* 21(6) p. 260-4 (2000) by Wyman N P et al.; *Science* 287(5455) p. 1049-53 (2000) by Hirsch et al.; *FASEB J* 15(11) p. 2019-21 (2001) by Hirsch et al. and *Nat Immunol.* 2(2) p. 108-15 (2001) by Gerard C. et al.).

Recent advances using genetic approaches and pharmacological tools have provided insights into signaling and molecular pathways that mediate chemotaxis in response to chemoattractant activated G-protein coupled receptors PI3-Kinase, responsible for generating these phosphorylated signalling products, was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., *Trends Cell Biol.* 2 p. 358-60 (1992)). However, more recent biochemical studies revealed that, class I PI3 kinases (e.g. class IB isoform PI3Kγ) are dual-specific kinase enzymes, means they display both: lipid kinase (phosphorylation of phospho-inositides) as well as protein kinase activity, shown to be capable of phosphorylation of other protein as substrates, including auto-phosphorylation as intra-molecular regulatory mechanism.

So, PI3-kinase activation, therefore, is believed to be involved in a range of cellular responses including cell growth, differentiation, and apoptosis (Parker et al., *Current Biology*, 5 p. 577-99 (1995), Yao et al., *Science*, 267 p. 2003-05 (1995)).

PI3-kinase appears to be involved in a number of aspects of leukocyte activation. A p85-associated PI3-kinase activity has been shown to physically associate with the cytoplasmic domain of CD28, which is an important costimulatory molecule for the activation of T-cells in response to antigen (Pages et al., *Nature*, 369 p, 327-29 (1994); Rudd, *Immunity* 4 p. 527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., *Science*, 251 p. 313-16 (1991)). Mutation of CD28 such that it can longer interact with PI3-kinase leads to a failure to initiate IL2 production, suggesting a critical role for PI3-kinase in T cell activation. PI3Kγ has been identified as a mediator of G beta-gamma-dependent regulation of JNK activity, and G beta-gamma are subunits of heterotrimeric G proteins (*J. Biol. Chem.* 273(5) p. 2505-8 (1998). Cellular processes in which PI3Ks play an essential role include suppression of apoptosis, reorganization of the actin skeleton, cardiac myocyte growth, glycogen synthase stimulation by insulin, TNFα-mediated neutrophil priming and superoxide generation, and leukocyte migration and adhesion to endothelial cells. Recently, (*Immunity* 16(3) p. 441-51 (2002)) it has been described that PI3Kγ relays inflammatory signals through various G(i)-coupled receptors and its central to mast cell function, stimuli in context of leukocytes, immunology includes cytokines, chemokines, adenosines, antibodies, integrins, aggregation factors, growth factors, viruses or hormones for example (*J. Cell. Sci* 114(Pt 16) p. 2903-10 (2001) by Lawlor M A et al., *Immunity* 16(3) p. 441-51 (2002) by Laffargue M. et al. and *Curr. Opinion Cell Biol.* 14(2) p. 203-13 (2002) by Stephens L. et al.).

Specific inhibitors against individual members of a family of enzymes provide invaluable tools for deciphering functions of each enzyme. Two compounds, LY294002 and wortmannin (cf.hereinafter), have been widely used as PI3-kinase inhibitors. These compounds are non-specific PI3K inhibitors, as they do not distinguish among the four members of Class I PI3-kinases. For example, the $IC_{50}$ values of wortmannin against each of the various Class I PI3-kinases are in the range of 1-10 nM. Similarly, the $IC_{50}$ values for LY294002 against each of these PI3-kinases is about 15-20 μM (Fruman et al., *An. Rev. Biochem.*, 67 p. 481-507 (1998)), also 5-10 microM on CK2 protein kinase and some inhibitory activity on phospholipases. Wortmannin is a fungal metabolite which irreversibly inhibits PI3K activity by binding covalently to the catalytic domain of this enzyme. Inhibition of PI3K activity by wortmannin eliminates the subsequent cellular response to the extracellular factor. For example, neutrophils respond to the chemokine fMet-Leu-Phe (fMLP) by stimulating PI3K and synthesizing PtdIns (3, 4, 5)$P_3$. This synthesis correlates with activation of the respirators burst involved in neutrophil destruction of invading microorganisms. Treatment of neutrophils with wortmannin prevents the fMLP-induced respiratory burst response (Thelen et al. *PNAS* 91 p. 4960-64 (1994)). Indeed, these experiments with wortmannin, as well as other experimental evidence, shows that PI3K activity in cells of hematopoietic lineage, particularly neutrophils, monocytes, and other types of leukocytes, is involved in many of the non-memory immune response associated with acute and chronic inflammation.

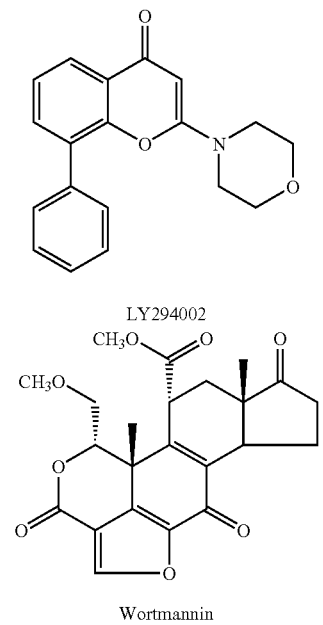

LY294002

Wortmannin

Based on studies using wortmannin, there is evidence that PI3-kinase function also is required for some aspects of leukocyte signaling through G-protein coupled receptors (Thelen et al., *Proc. Natl. Acad. Sci. USA*, 91 p. 4960-64 (1994)). Moreover, it has been shown that wortmannin and LY294002 block neutrophil migration and superoxide release. However, in as much as these compounds do not distinguish among the various isoforms of PI3K, it remains unclear which particular PI3K isoform or isoforms are involved in these phenomena.

Azolidinone-vinyl benzene derivatives—having a mandatory benzimidazole moiety though—are described in WO 02/051409. The compounds are said to inhibit telomerase and are purportedly useful in the treatment of cancer.

SUMMARY OF THE INVENTION

The present invention relates to the use of azolidinone-vinyl fused-benzene derivatives of formula (I)

(I)

wherein A, X, Y, Z, n, $R^1$ and $R^2$ are described in details in the description hereinafter, as well as pharmaceutically acceptable salts thereof, for the preparation of pharmaceutical compositions for the treatment and/or prophylaxis of autoimmune disorders and/or inflammatory diseases, cardiovascular diseases, neurodegenerative diseases, bacterial or viral infections, kidney diseases, platelet aggregation, cancer, transplantation complications, graft rejection or lung injuries. Compounds of this invention are inhibitors of Phosphatoinositides 3-kinases (PI3Ks), particularly of Phosphatoinositides 3-kinases gamma (PI3Kγ).

DESCRIPTION OF THE INVENTION

It has now been found that compounds of the present invention are modulators of the Phosphatoinositides 3-kinases (PI3Ks), particularly of Phosphatoinositides 3-kinase γ (PI3Kγ). When the phosphatoinositides 3-kinase (PI3K) enzyme is inhibited by the compounds of the present invention, PI3K is unable to exert its enzymatic, biological and/or pharmacological effects. The compounds of the present invention are therefore useful in the treatment and prevention of autoimmune disorders and/or inflammatory diseases, cardiovascular diseases, neurodegenerative diseases, bacterial or viral infections, kidney diseases, platelet aggregation, cancer, transplantation complications, graft rejection or lung injuries.

The following paragraphs provide definitions of the various chemical moieties that make up the compounds according to the invention and are intended to apply uniformly through-out the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-pentyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=CH$_2$), n-2-propenyl (allyl, —CH$_2$CH=CH$_2$) and the like.

"$C_2$-$C_6$-alkenyl aryl" refers to $C_2$-$C_6$-alkenyl groups having an aryl substituent including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—CH$_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"Heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Preferred heterocycloalkyl include pyrrolidine, piperidine, piperazine, 1-methylpiperazine, morpholine, and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having an carboxy substituent, including 2-carboxyethyl and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", heterocycloalkyl "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —C(O)OR where R includes H, "$C_1$-$C_6$-alkyl" or "aryl" or "heteroaryl" or "$C_1$-$C_6$-alkyl aryl" or "$C_1$-$C_6$-alkyl heteroaryl".

"$C_1$-$C_6$-alkyl alkoxycarbonyl" refers to $C_1$-$C_5$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino)ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R,R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_5$-alkyl groups having an amino substituent, including 2-(1-pyrrolidinyl)ethyl and the like.

"Ammonium" refers to a positively charged group —N$^+$RR'R", where each R,R',R" is independently "$C_1$-$C_6$-alkyl" or "$C_1$-$C_6$-alkyl aryl" or "$C_1$-$C_6$-alkyl heteroaryl", or "cycloalkyl", or "heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyloxy" refers to C$_1$-C$_5$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "C$_1$-C$_6$-alkyl", "C$_1$-C$_6$-alkyl" substituted with halogens, e.g., an —SO$_2$—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonyl" refers to C$_1$-C$_5$-alkyl groups having a sulfonyl substituent, including 2-(methylsulfonyl)ethyl and the like.

"Sulfinyl" refers to a group "—S(O)—R" wherein R is selected from H, "C$_1$-C$_6$-alkyl", "C$_1$-C$_6$-alkyl" substituted with halogens, e.g., a —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfinyl" refers to C$_1$-C$_5$-alkyl groups having a sulfinyl substituent, including 2-(methylsulfinyl)ethyl and the like.

"Sulfanyl" refers to groups —S—R where R includes H, "C$_1$-C$_6$-alkyl", "C$_1$-C$_6$-alkyl" substituted with halogens, e.g., a —SO—CF$_3$ group, "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl". Preferred sulfanyl groups include methylsulfanyl, ethylsulfanyl, and the like.

"C$_1$-C$_6$-alkyl sulfanyl" refers to C$_1$-C$_5$-alkyl groups having a sulfanyl substituent, including 2-(ethylsulfanyl)ethyl and the like.

"Sulfonylamino" refers to a group —NRSO$_2$—R' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl"; "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl sulfonylamino" refers to C$_1$-C$_5$-alkyl groups having a sulfonylamino substituent, including 2-(ethylsulfonylamino)ethyl and the like.

"Aminosulfonyl" refers to a group SO$_2$—NRR' where each R, R' includes independently hydrogen, "C$_1$-C$_6$-alkyl", "C$_2$-C$_6$-alkenyl", "C$_2$-C$_6$-alkynyl", "C$_3$-C$_8$-cycloalkyl", "heterocycloalkyl", "aryl", "heteroaryl", "C$_1$-C$_6$-alkyl aryl" or "C$_1$-C$_6$-alkyl heteroaryl", "C$_2$-C$_6$-alkenyl aryl", "C$_2$-C$_6$-alkenyl heteroaryl", "C$_2$-C$_6$-alkynyl aryl", "C$_2$-C$_6$-alkynylheteroaryl", "C$_1$-C$_6$-alkyl cycloalkyl", "C$_1$-C$_6$-alkyl heterocycloalkyl".

"C$_1$-C$_6$-alkyl aminosulfonyl" refers to C$_1$-C$_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "C$_1$-C$_6$-alkyl", "C$_2$-C$_6$-alkenyl", "C$_2$-C$_6$-alkynyl", "cycloalkyl", "heterocycloalkyl", "C$_1$-C$_6$-alkyl aryl", "C$_1$-C$_6$-alkyl heteroaryl", "C$_1$-C$_6$-alkyl cycloalkyl", "C$_1$-C$_6$-alkyl heterocycloalkyl", "amino", "ammonium", "acyl", "acyloxy", "acylamino", "aminocarbonyl", "alkoxycarbonyl", "ureido", "aryl", "carbamate", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable cationic salts or complexes" is intended to define such salts as the alkali metal salts, (e.g. sodium and potassium), alkaline earth metal salts (e.g. calcium or magnesium), aluminium salts, ammonium salts and salts with organic amines such as with methylamine, dimethylamine, trimethylamine, ethylamine, triethylamine, morpholine, N-Me-D-glucamine, N,N'-bis(phenylmethyl)-1,2-ethanediamine, ethanolamine, diethanolamine, ethylenediamine, N-methylmorpholine, piperidine, benzathine (N,N'-dibenzylethylenediamine), choline, ethylene-diamine, meglumine (N-methylglucamine), benethamine (N-benzylphenethylamine), diethylamine, piperazine, thromethamine (2-amino-2-hydroxymethyl-1,3-propanediol), procaine as well as amines of formula —NR,R',R" wherein R,R',R" is independently hydrogen, alkyl or benzyl. Especially preferred salts are sodium and potassium salts.

"Pharmaceutically acceptable salts or complexes" refers to salts or complexes of the below-identified compounds of the present invention that retain the desired biological activity. Examples of such salts include, but are not restricted to acid addition salts formed with inorganic acids (e.g., hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. Said compounds can also be administered as pharmaceutically acceptable quaternary salts known by a person skilled in the art, which specifically include the quarternary ammonium salt of the formula —NR, R',R"$^+$ Z$^-$, wherein R, R', R" is independently hydrogen, alkyl, or benzyl, C$_1$-C$_6$-alkyl, C$_2$-C$_6$-alkenyl, C$_2$-C$_6$-alkynyl, C$_1$-C$_6$-alkyl aryl, C$_1$-C$_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

General formula (I) according to the present invention also comprises its tautomers, its geometrical isomers, its optically active forms as enantiomers, diastereomers and its racemate forms, as well as pharmaceutically acceptable salts thereof. Preferred pharmaceutically acceptable salts of the formulae of the present invention are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

The compounds of the present invention may be obtained as E/Z isomer mixture or as essentially pure E-isomers or Z isomers. The E/Z isomerism preferably refers to the vinyl moiety linking the phenyl with the azolidinone moiety. In a specific embodiment, the compounds of formula (I) are Z-isomers.

A first aspect of the present invention consists in the use of compounds of formula (I)

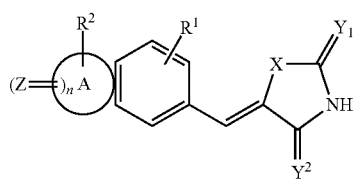

as well as its geometrical isomers, its optically active forms as enantiomers, diastereomers and its racemate forms, as well as pharmaceutically acceptable salts and pharmaceutically active derivatives thereof for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation complications due to rejection reactions, graft rejection or lung injuries.

In a preferred embodiment, these compounds are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another preferred embodiment according to the invention, these compounds are useful for the treatment and/or prophylaxis of neurodegenerative diseases including multiple sclerosis, Alzheimer's disease, Huntington's disease, CNS trauma, stroke or ischemic conditions.

In a particularly preferred embodiment according to the invention, these compounds are useful for the treatment and/or prophylaxis of cardiovascular diseases such as atherosclerosis, heart hypertrophy, cardiac myocyte dysfunction, elevated blood pressure or vasoconstriction.

In another particularly preferred embodiment according to the invention, these compounds are useful for the treatment and/or prophylaxis of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastisis, in particular melanoma, Karposi's sarcoma, acute and chronic bacterial and viral infections, sepsis, transplantation complications due to rejection reactions, graft rejection, glomerulo sclerosis, glomerulo nephritis, progressive renal fibrosis, endothelial and epithelial injuries in the lung or in general lung airways inflammation.

The substituents within formula (I) are defined as follows:

A is an unsubstituted or substituted 5-8 membered heterocyclic group or an unsubstituted or substituted carbocyclic group.

Said carbocyclic group may be fused with an unsubstituted or substituted aryl, an unsubstituted or substituted heteroaryl, an unsubstituted or substituted cycloalkyl or an unsubstituted or substituted heterocycloalkyl.

Such heterocyclic or carbocyclic groups comprise aryl, heteroaryl, cycloalkyl and heterocycloalkyl, including phenyl, phenantrenyl, cyclopentyl, cyclohexyl, norbornyl, pyrrolidine, piperidine, piperazine, 1-methylpiperazine, morpholine, pyrrolyl, furanyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xantbenyl or benzoquinolyl Further exemplary heterocyclic or carbocyclic groups A include unsubstituted or substituted dioxol, unsubstituted or substituted dioxin, unsubstituted or substituted dihydrofuran, unsubstituted or substituted (dihydro) furanyl, unsubstituted or substituted (dihydro)oxazinyl, unsubstituted or substituted oxazinoyl, unsubstituted or substituted pyridinyl, unsubstituted or substituted isooxazolyl, unsubstituted or substituted oxazolyl unsubstituted or substituted (dihydro)napthalenyl, unsubstituted or substituted pyrimidinyl, unsubstituted or substituted triazolyl, unsubstituted or substituted imidazolyl, unsubstituted or substituted pyrazinyl, unsubstituted or substituted thiazolyl, unsubstituted or substituted thiadiazolyl, unsubstituted or substituted oxadiazolyl.

X is S, O or NH, preferably S.

$Y^1$ and $Y^2$ are independently from each other selected from the group consisting of S, O or —NH, preferably O.

Z is S or O, preferably O.

$R^1$ is selected from the group comprising or consisting of H, CN, carboxy, acyl, $C_1$-$C_6$-alkoxy, halogen, hydroxy, acyloxy, an unsubstituted or substituted $C_1$-$C_6$-alkyl carboxy, an unsubstituted or substituted $C_1$-$C_6$-alkyl acyloxy, an unsubstituted or substituted $C_1$-$C_6$-alkyl alkoxy, alkoxycarbonyl, an unsubstituted or substituted $C_1$-$C_6$-alkyl alkoxycarbonyl, aminocarbonyl, an unsubstituted or substituted $C_1$-$C_6$-alkyl aminocarbonyl, acylamino, an unsubstituted or substituted $C_1$-$C_6$-alkyl acylamino, ureido, an unsubstituted or substituted $C_1$-$C_6$-alkyl ureido, amino, an unsubstituted or substituted $C_1$-$C_6$-alkyl amino, ammonium, sulfonyloxy, an unsubstituted or substituted $C_1$-$C_6$-alkyl sulfonyloxy, sulfonyl, an unsubstituted or substituted $C_1$-$C_6$-alkyl sulfonyl, sulfinyl, an unsubstituted or substituted $C_1$-$C_6$-alkyl sulfinyl, sulfanyl, an unsubstituted or substituted $C_1$-$C_6$-alkyl sulfanyl, sulfonylamino, an unsubstituted or substituted $C_1$-$C_6$-alkyl sulfonylamino or carbamate. In a specific embodiment $R^1$ is H.

$R^2$ is selected from the group comprising or consisting of H, halogen, acyl, amino, an unsubstituted or substituted $C_1$-$C_6$-alkyl, an unsubstituted or substituted $C_2$-$C_6$-alkenyl, an unsubstituted or substituted $C_2$-$C_6$-alkynyl, an unsubstituted or substituted $C_1$-$C_6$-alkyl carboxy, an unsubstituted or substituted $C_1$-$C_6$-alkyl acyl, an unsubstituted or substituted $C_1$-$C_6$-alkyl alkoxycarbonyl, an unsubstituted or substituted $C_1$-$C_6$-alkyl aminocarbonyl, an unsubstituted or substituted $C_1$-$C_6$-alkyl acyloxy, an unsubstituted or substituted $C_1$-$C_6$-alkyl acylamino, an unsubstituted or substituted $C_1$-$C_6$-alkyl ureido, an unsubstituted or substituted $C_1$-$C_6$-alkyl carbamate, an unsubstituted or substituted $C_1$-$C_6$-alkyl amino, an unsubstituted or substituted $C_1$-$C_6$-alkyl alkoxy, an unsubstituted or substituted $C_1$-$C_6$-alkyl sulfanyl, an unsubstituted or substituted $C_1$-$C_6$-alkyl sulfinyl, an unsubstituted or substituted $C_1$-$C_6$-alkyl sulfonyl, an unsubstituted or substituted $C_1$-$C_6$-alkyl sulfonylaminoaryl, an unsubstituted or substituted aryl, an unsubstituted or substituted $C_3$-$C_8$-cycloalkyl or heterocycloalkyl, an unsubstituted or substituted $C_1$-$C_6$-alkyl aryl, an unsubstituted or substituted $C_2$-$C_6$-alkenyl aryl, an unsubstituted or substituted $C_2$-$C_6$-alkynyl aryl, carboxy, cyano, hydroxy, $C_1$-$C_6$-alkoxy, nitro, acylamino, ureido, sulfonylamino, sulfanyl, or sulfonyl.

n is an integer 0, 1 or 2, preferably n is 0 or 1. Most preferred is n=0.

According to a specific embodiment of the invention, $R^1$ and $R^2$ are both H.

In a further specific embodiment according to the invention, X is S, $Y^1$ and $Y^2$ are both O, $R^1$ and $R^2$ are as above defined and n is 0.

A further particularly preferred aspect of the present invention is related to the use of thiazolidinedione-vinyl fused-benzene derivatives of formula (Ia), (Ib), (Ic) and (Id) for the preparation of a medicament for the prophylaxis and/or treatment of autoimmune disorders and/or inflammatory diseases, cardiovascular diseases, neurodegenerative diseases, bacterial or viral infections, kidney diseases, platelet aggregation, cancer, transplantation complications due to rejection reactions, graft rejection or lung injuries

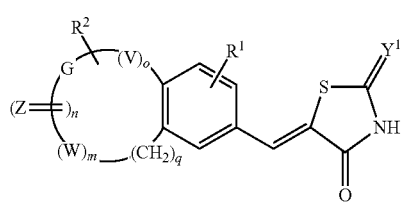

(Ia)

$R^1$, $R^2$, $Y^1$, Z and n in formula (Ia) are as above-defined.

G in formula (Ia) is an unsubstituted or substituted $C_1$-$C_5$ alkylene (e.g. methylene, ethylene, propylene etc.) or an unsubstituted or substituted $C_1$-$C_5$ alkenylene group (e.g. a methine (—CH=), a —CH=CH— group, a propenylene group, etc.).

W and V in formula (Ia) are each independently from each other selected from O, S, —NR³ wherein R³ is H or an unsubstituted or substituted $C_1$-$C_6$ alkyl group, m and o are each independently from each other 0 or 1; o is an integer from 1 to 4 and q is an integer from 0 to 4.

Even more preferred compounds of formula (Ia) is where G is an $C_1$-$C_4$ alkylene, thus giving compounds of formula (Ib) (i.e. p=1, 2, 3 or 4, preferably 1 or 2).

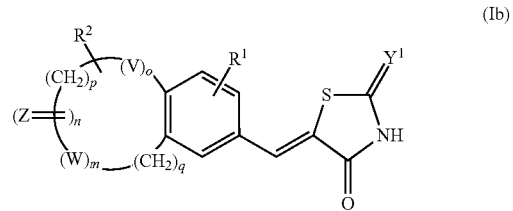

(Ib)

A specific sub-group of formula (Ib) are compounds having the formula (Ic), whereby W, $R^1$, $Y^1$ are as above defined; specifically $R^1$ may be an unsubstituted or substituted $C_1$-$C_4$ alkyl group or an unsubstituted or substituted $C_1$-$C_5$ alkenyl group, carboxy, cyano, $C_1$-$C_4$-alkoxy, nitro, acylamino, ureido.

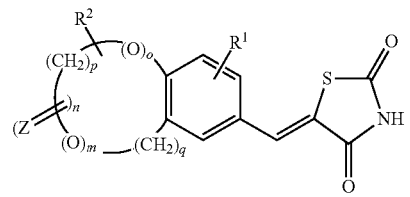

(Ic)

Still a further specific sub-group of formula (Ia) are compounds, wherein V, W and $Y^1$ are all O, thus providing compounds of formula (Id).

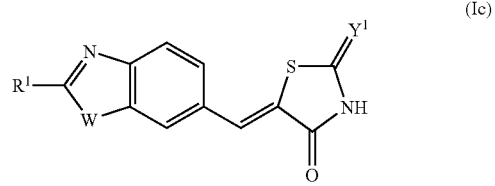

(Id)

In a preferred embodiment of formulae (Ia), (Ib) or (Id), n is 0, m is 1, p is 1 or 2, o is 0, q is 1, and $R^1$ and $R^2$ are as above-defined.

In a further specific embodiment of formulae (Ia), (Ib) or (Id), m is 1, n is 0, p is 1 or 2, q is 0, o is 1 while $R^1$ and $R^2$ are as above-defined, more particularly $R^1$ is halogen or a hydrogen atom.

In another specific embodiment of formula (Ia), (Ib) or (Id), p is 1 or 2, q is 0, m is 0, n is 1 and $R^1$ and $R^2$ are as above-defined.

The compounds of the present invention are suitable for the modulation, notably the inhibition of the activity of phosphatoinositides 3-kinases (PI3K), particularly phosphatoinositides 3-kinase (PI3Kγ). It is therefore believed that the compounds of the present invention are also particularly useful for the treatment and/or prevention of disorders which are mediated by PI3Ks, particularly PI3Kγ. Said treatment involves the modulation—notably the inhibition or the down regulation—of the phosphatoinositides 3-kinases.

The following compounds are not included by formula (I):

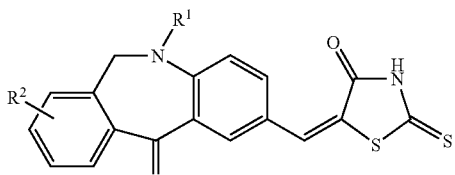

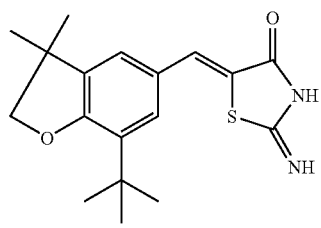

R¹ is a lower alkyl or aralkyl and R² is H or a halogen. The compounds TE are disclosed in JP 55 045648 as intermediate compounds without any biological activity, while JA is mentioned in the *Journal of Medicinal Chemistry* (1998), 41(18), 3515-3529 as being inactive in a paw swelling assay.

Compounds of the present invention include in particular those of the group consisting of:

5-(1,3-benzodioxol-5-ylmethylene)-1,3-thiazolidine-2,4-dione
5-(1,3-benzodioxol-5-ylmethylene)-2-thioxo-1,3-thiazolidin-4-one
5-(2,3-dihydro-1,4-benzodioxin-6-ylmethylene)-1,3-thiazolidine-2,4-dione
5-(2,3-dihydro-1-benzofuran-5-ylmethylene)-1,3-thiazolidine-2,4-dione
5-[(7-methoxy-1,3-benzodioxol-5-yl)methylene]-1,3-thiazolidine-2,4-dione
5-[(9,10-dioxo-9,10-dihydroanthracen-2-yl)methylene]-1,3-thiazolidine-2,4-dione
(5-[(2,2-difluoro-1,3-benzodioxol-5-yl)methylene]-1,3-thiazolidine-2,4-dione
(5Z)-5-(1,3-dihydro-2-benzofuran-5-ylmethylene)-1,3-thiazolidine-2,4-dione
5-(1-benzofuran-5-ylmethylene)-1,3-thiazolidine-2,4-dione
5-[(4-methyl-3-oxo-3,4-dihydro-2H-1,4-benzoxazin-6-yl)methylene]-1,3-thiazolidine-2,4-dione
5-(1,3-benzodioxol-5-ylmethylene)-2-imino-1,3-thiazolidin-4-one
5-Quinolin-6-ylmethylene-thiazolidine-2,4-dione
5-Quinolin-6-ylmethylene-2-thioxo-thiazolidin-4-one
2-Imino-5-quinolin-6-ylmethylene-thiazolidin-4-one
5-(3-Methyl-benzo[d]isoxazol-5-ylmethylene)-thiazolidine-2,4-dione
5-(4-Phenyl-quinazolin-6-ylmethylene)-thiazolidine-2,4-dione
5-(4-Dimethylamino-quinazolin-6-ylmethylene)-thiazolidine-2,4-dione
5-[(4-aminoquinazolin-6-yl)methylene]-1,3-thiazolidine-2,4-dione
5-[(4-piperidin-1-ylquinazolin-6-yl)methylene]-1,3-thiazolidine-2,4-dione
5-[(4-morpholin-4-ylquinazolin-6-yl)methylene]-1,3-thiazolidine-2,4-dione
5-{[4-(benzylamino)quinazolin-6-yl]methylene}-1,3-thiazolidine-2,4-dione
5-{[4-(diethylamino)quinazolin-6-yl]methylene}-1,3-thiazolidine-2,4-dione
5-({4-[(pyridin-2-ylmethyl)amino]quinazolin-6-yl}methylene)-1,3-thiazolidine-2,4-dione
5-({4-[(pyridin-3-ylmethyl)amino]quinazolin-6-yl}methylene)-1,3-thiazolidine-2,4-dione
ethyl 1-{6-[(2,4-dioxo-1,3-thiazolidin-5-ylidene)methyl]quinazolin-4-yl}piperidine-3-carboxylate
ethyl 1-{6-[(2,4-dioxo-1,3-thiazolidin-5-ylidene)methyl]quinazolin-4-yl}piperidine-4-carboxylate
tert-butyl 1-{6-[(2,4-dioxo-1,3-thiazolidin-5-ylidene)methyl]quinazolin-4-yl}-L-prolinate
5-{[4-(4-methylpiperazin-1-yl)quinazolin-6-yl]methylene}-1,3-thiazolidine-2,4-dione
5-{[4-(4-pyrimidin-2-ylpiperazin-1-yl)quinazolin-6-yl]methylene}-1,3-thiazolidine-2,4-dione
5-({4-[4-(4-fluorophenyl)piperidin-1-yl]quinazolin-6-yl}methylene)-1,3-thiazolidine-2,4-dione
5-{[4-(4-benzylpiperidin-1-yl)quinazolin-6-yl]methylene}-1,3-thiazolidine-2,4-dione
5-({4-[4-(2-phenylethyl)piperidin-1-yl]quinazolin-6-yl}methylene)-1,3-thiazolidine-2,4-dione
5-{[4-(4-methylpiperidin-1-yl)quinazolin-6-yl]methylene}-1,3-thiazolidine-2,4-dione
5-{[4-(4-hydroxypiperidin-1-yl)quinazolin-6-yl]methylene}-1,3-thiazolidine-2,4-dione
1-[6-(2,4-Dioxo-thiazolidin-5-ylidenemethyl)-quinazolin-4-yl]-piperidine-4-carboxylic acid
1-[6-(2,4-Dioxo-thiazolidin-5-ylidenemethyl)-quinazolin-4-yl]-piperidine-3-carboxylic acid
1-[6-(2,4-Dioxo-thiazolidin-5-ylidenemethyl)-quinazolin-4-yl]-pyrrolidine-2-carboxylic acid
5-(4-Methylamino-quinazolin-6-ylmethylene)-thiazolidine-2,4-dione
5-(4-Methoxy-quinazolin-6-ylmethylene)-thiazolidine-2,4-dione
2-Imino-5-(4-methylamino-quinazolin-6-ylmethylene)-thiazolidin-4-one
2-Imino-5-(4-piperidine-quinazolin-6-ylmethylene)-thiazolidin-4-one
2-Imino-5-(4-dimethylamino-quinazolin-6-ylmethylene)-thiazolidin-4-one
5-(2-Methyl-2H-benzotriazol-5-ylmethylene)-thiazolidine-2,4-dione
5-(3-Methyl-3H-benzotriazol-5-ylmethylene)-thiazolidine-2,4-dione
5-(3-Ethyl-3H-benzoimidazol-5-ylmethylene)-thiazolidine-2,4-dione
5-{[1-(4-phenylbutyl)-1H-benzimidazol-6-yl]methylene}-1,3-thiazolidine-2,4-dione
5-[(1-prop-2-yn-1-yl-1H-benzimidazol-6-yl)methylene]-1,3-thiazolidine-2,4-dione
5-[(1-{2-[4-(trifluoromethyl)phenyl]ethyl}-1H-benzimidazol-6-yl)methylene]-1,3-thiazolidine-2,4-dione
5-({1-[2-(4-hydroxyphenyl)ethyl]-1H-benzimidazol-6-yl}methylene)-1,3-thiazolidine-2,4-dione
methyl 4-{6-[(2,4-dioxo-1,3-thiazolidin-5-ylidene)methyl]-1H-benzimidazol-1-yl}cyclohexanecarboxylate
5-({1-[2-(5-methoxy-1H-indol-3-yl)ethyl]-1H-benzimidazol-6-yl}methylene)-1,3-thiazolidine-2,4-dione
5-({1-[(1-methyl-1H-pyrazol-4-yl)methyl]-1H-benzimidazol-6-yl}methylene)-1,3-thiazolidine-2,4-dione
5-({1-[2-(3,4-dimethoxyphenyl)ethyl]-1H-benzimidazol-6-yl}methylene)-1,3-thiazolidine-2,4-dione
5-({1-[2-(4-phenoxyphenyl)ethyl]-1H-benzimidazol-6-yl}methylene)-1,3-thiazolidine-2,4-dione 5-({1-[4-(trifluoromethyl)benzyl]-1H-benzimidazol-6-yl}methylene)-1,3-thiazolidine-2,4-dione
4-{6-[(2,4-dioxo-1,3-thiazolidin-5-ylidene)methyl]-1H-benzimidazol-1-yl}cyclohexanecarboxylic acid
5-[(1-isobutyl-1H-benzimidazol-6-yl)methylene]-1,3-thiazolidine-2,4-dione
5-({1-[2-(1,3-benzodioxol-4-yl)ethyl]-1H-benzimidazol-6-yl}methylene)-1,3-thiazolidine-2,4-dione
5-({1-[2-(2-phenoxyphenyl)ethyl]-1H-benzimidazol-6-yl}methylene)-1,3-thiazolidine-2,4-dione
5-{[1-(3,3-diphenylpropyl)-1H-benzimidazol-6-yl]methylene}-1,3-thiazolidine-2,4-dione
5-{[1-(2-methoxybenzyl)-1H-benzimidazol-6-yl]methylene}-1,3-thiazolidine-2,4-dione
5-{[1-(3-furylmethyl)-1H-benzimidazol-6-yl]methylene}-1,3-thiazolidine-2,4-dione
5-[(1-propyl-1H-benzimidazol-6-yl)methylene]-1,3-thiazolidine-2,4-dione
5-Quinoxalin-6-ylmethylene-thiazolidine-2,4-dione
5-Quinoxalin-6-ylmethylene-2-thioxo-thiazolidin-4-one
2-Imino-5-quinoxalin-6-ylmethylene-thiazolidin-4-one
5-Benzothiazol-6-ylmethylene-thiazolidine-2,4-dione
5-(3-Methyl-benzofuran-5-ylmethylene)-thiazolidine-2,4-dione
5-(2-Bromo-3-methyl-benzofuran-5-ylmethylene)-thiazolidine-2,4-dione
5-(3-bromo-benzofuran-5-ylmethylene)-thiazolidine-2,4-dione
3-[5-(2,4-Dioxo-thiazolidin-5-ylidenemethyl)-benzofuran-3-yl]-acrylic acid ethyl ester
3-[5-(2,4-Dioxo-thiazolidin-5-ylidenemethyl)-benzofuran-3-yl]-acrylic acid
5-[3-(3-Oxo-3-piperidin-1-yl-propenyl)-benzofuran-5-ylmethylene]-thiazolidine-2,4-dione
Methyl 1-((3-{5-[(2,4-dioxo-1,3-thiazolidin-5-ylidene)methyl]-1-benzofuran-3-yl}prop-2-enoyl)prolinate
Methyl 1-((3-{5-[(2,4-dioxo-1,3-thiazolidin-5-ylidene)methyl]-1-benzofuran-3-yl}prop-2-enoyl)-D-prolinate
(5-({3-[(3-oxo-3-pyrrolidin-1-ylprop-1-en-1-yl]-1-benzofuran-5-yl}methylene)-1,3-thiazolidine-2,4-dione
5-({3-[3-morpholin-4-yl-3-oxoprop-1-en-1-yl]-1-benzofuran-5-yl}methylene)-1,3-thiazolidine-2,4-dione
Methyl 1-(3-{5-[(2,4-dioxo-1,3-thiazolidin-5-ylidene)methyl]-1-benzofuran-3-yl}prop-2-enoyl)-L-prolinate
N-cyclohexyl-3-{5-[(2,4-dioxo-1,3-thiazolidin-5-ylidene)methyl]-1-benzofuran-3-yl}-N-methylacrylamide
3-{5-[(2,4-dioxo-1,3-thiazolidin-5-ylidene)methyl]-1-benzofuran-3-yl}-N-ethyl-N-(2-hydroxyethyl)acrylamide
N-cyclobutyl-3-{5-[(2,4-dioxo-1,3-thiazolidin-5-ylidene)methyl]-1-benzofuran-3-yl}acrylamide
5-({3-[3-azetidin-1-yl-3-oxoprop-1-en-1-yl]-1-benzofuran-5-yl}methylene)-1,3-thiazolidine-2,4-dione
5-({3-[3-(1,3-dihydro-2H-isoindol-2-yl)-3-oxoprop-1-en-1-yl]-1-benzofuran-5-yl}methylene)-1,3-thiazolidine-2,4-dione
5-({3-[3-azepan-1-yl-3-oxoprop-1-en-1-yl]-1-benzofuran-5-yl}methylene)-1,3-thiazolidine-2,4-dione
3-{5-[(2,4-dioxo-1,3-thiazolidin-5-ylidene)methyl]-1-benzofuran-3-yl}-N-piperidin-1-ylacrylamide
3-{5-[(2,4-dioxo-1,3-thiazolidin-5-ylidene)methyl]-1-benzofuran-3-yl}-N-(pyridin-3-ylmethyl)acrylamide
N-cyclohexyl-3-{5-[(2,4-dioxo-1,3-thiazolidin-5-ylidene)methyl]-1-benzofuran-3-yl}acrylamide
5-({3-[3-(4-methylpiperazin-1-yl)-3-oxoprop-1-en-1-yl]-1-benzofuran-5-yl}methylene)-1,3-thiazolidine-2,4-dione
N-cycloheptyl-3-{5-[(2,4-dioxo-1,3-thiazolidin-5-ylidene)methyl]-1-benzofuran-3-yl}acrylamide
5-({3-[3-(2,5-dihydro-1H-pyrrol-1-yl)-3-oxoprop-1-en-1-yl]-1-benzofuran-5-yl}methylene)-1,3-thiazolidine-2,4-dione
N-cyclopentyl-3-{5-[(2,4-dioxo-1,3-thiazolidin-5-ylidene)methyl]-1-benzofuran-3-yl}acrylamide
3-[5-(2,4-Dioxo-thiazolidin-5-ylidenemethyl)-benzofuran-3-yl]-propionic acid ethyl ester
3-[5-(2,4-Dioxo-thiazolidin-5-ylidenemethyl)-benzofuran-3-yl]-propionic acid
5-[3-(3-Oxo-3-piperidin-1-yl-propyl)-benzofuran-5-ylmethylene]-thiazolidine-2,4-dione
6-(2,4-Dioxo-thiazolidin-5-ylidenemethyl)-2,3-dihydro-benzo[1,4]oxazine-4-carboxylic acid tert-butyl ester
5-(3,4-Dihydro-2H-benzo[1,4]oxazin-6-ylmethylene)-thiazolidine-2,4-dione
5-(4-Benzoyl-3,4-dihydro-2H-benzo[1,4]oxazin-6-ylmethylene)-thiazolidine-2,4-dione
5-(4-Acetyl-3,4-dihydro-2H-benzo[1,4]oxazin-6-ylmethylene)-thiazolidine-2,4-dione
6-(2,4-Dioxo-thiazolidin-5-ylidenemethyl)-benzo[1,4]oxazine-4-carboxylic acid tert-butyl ester
[6-(2,4-Dioxo-thiazolidin-5-ylidenemethyl)-3-oxo-2,3-dihydro-benzo[1,4]-oxazin-4-yl]-acetic acid methyl ester
N-Benzyl-2-[6-(2,4-dioxo-thiazolidin-5-ylidenemethyl)-3-oxo-2,3-dihydro-benzo[1,4]oxazin-4-yl]-acetamide
5-(4-Butyl-3-oxo-3,4-dihydro-2H-benzo[1,4]oxazin-6-ylmethylene)-thiazolidine-2,4-dione
5-(4-Benzyl-3-oxo-3,4-dihydro-2H-benzo[1,4]oxazin-6-ylmethylene)-thiazolidine-2,4-dione
5-(2-Chloro-benzofuran-5-ylmethylene)-thiazolidine-2,4-dione
5-(3-Amino-benzo[d]isoxazol-5-ylmethylene)-thiazolidine-2,4-dione
5-(3-Phenylethynyl-benzofuran-5-ylmethylene)-thiazolidine-2,4-dione
5-Benzo[1,2,5]thiadiazol-5-ylmethylene-thiazolidine-2,4-dione
5-Benzo[1,2,5]oxadiazol-5-ylmethylene-thiazolidine-2,4-dione
5-(2-Methyl-benzofuran-6-ylmethylene)-thiazolidine-2,4-dione
5-(2-Carboxymethyl-benzofuran-6-ylmethylene)-thiazolidine-2,4-dione
5-(3-Bromo-2-fluoro-2,3-dihydro-benzofuran-6-ylmethylene)-thiazolidine-2,4-dione
5-(2-Fluoro-benzofuran-6-ylmethylene)-thiazolidine-2,4-dione A further aspect of the invention consists in novel thiazolidinedione-vinyl fused-benzene derivatives of formula (II-a)

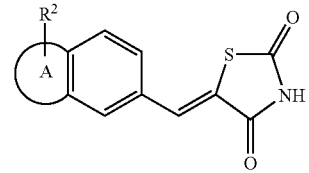

(II-a)

A is selected from the group consisting of unsubstituted or substituted dioxol, unsubstituted or substituted dioxin, unsubstituted or substituted dihydrofuran, unsubstituted or substituted (dihydro) furanyl, unsubstituted or substituted (dihydro)oxazinyl, unsubstituted or substituted oxazinoyl, unsubstituted or substituted pyridinyl, unsubstituted or substituted isooxazolyl, unsubstituted or substituted oxazolyl unsubstituted or substituted (dihydro)napthalenyl, unsubstituted or substituted pyrimidinyl, unsubstituted or substituted triazolyl, unsubstituted or substituted imidazolyl, unsubstituted or substituted pyrazinyl, unsubstituted or substituted thiazolyl, unsubstituted or substituted thiadiazolyl, unsubstituted or substituted oxadiazolyl.

$R^2$ is selected from the group comprising or consisting of H, halogen, acyl, amino, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkyl carboxy, unsubstituted or substituted $C_1$-$C_6$-alkyl acyl, unsubstituted or substituted $C_1$-$C_6$-alkyl alkoxycarbonyl, unsubstituted or substituted $C_1$-$C_6$-alkyl aminocarbonyl, unsubstituted or substituted $C_1$-$C_6$-alkyl acyloxy, unsubstituted or substituted $C_1$-$C_6$-alkyl acylamino, unsubstituted or substituted $C_1$-$C_6$-alkyl ureido, unsubstituted or substituted $C_1$-$C_6$-alkyl carbamate, unsubstituted or substituted $C_1$-$C_6$-alkyl amino, unsubstituted or substituted $C_1$-$C_6$-alkyl alkoxy, unsubstituted or substituted $C_1$-$C_6$-alkyl sulfanyl, unsubstituted or substituted $C_1$-$C_6$-alkyl sulfinyl, unsubstituted or substituted $C_1$-$C_6$-alkyl sulfonyl, unsubstituted or substituted $C_1$-$C_6$-alkyl sulfonylaminoaryl, an unsubstituted or substituted aryl, unsubstituted or substituted $C_3$-$C_8$-cycloalkyl or heterocycloalkyl, unsubstituted or substituted $C_1$-$C_6$-alkyl aryl, unsubstituted or substituted $C_2$-$C_6$-alkenyl-aryl, unsubstituted or substituted $C_2$-$C_6$-alkynyl aryl, carboxy, cyano, hydroxy, $C_1$-$C_6$-alkoxy, nitro, acylamino, ureido, sulfonylamino, sulfanyl, or sulfonyl.

More specific novel thiazolidinone-vinyl fused-benzene derivatives of formula (II)

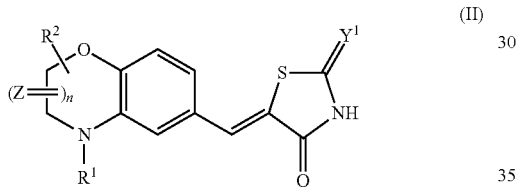
(II)

as well as its geometrical isomers, its optically active forms as enantiomers, diastereomers and its racemate forms, as well as pharmaceutically acceptable salts and pharmaceutically active derivatives thereof, wherein $Y^1$, Z, $R^1$, $R^2$ are as above defined and n is 0 or 1.

In a specific embodiment $R^1$ is an unsubstituted or substituted $C_1$-$C_6$-alkyl, an unsubstituted or substituted $C_1$-$C_6$-alkyl aryl, an unsubstituted or substituted aryl, an unsubstituted or substituted $C_3$-$C_8$-cycloalkyl or -heterocycloalkyl, an unsubstituted or substituted $C_1$-$C_6$-alkyl aryl, an unsubstituted or substituted $C_2$-$C_6$-alkenyl-aryl, an unsubstituted or substituted $C_2$-$C_6$-alkynyl aryl.

In another preferred embodiment according to the present invention $Y^1$ is O.

Still another aspect of the invention consists in novel thiazolidinone-vinyl fused-benzene derivatives of formula (III)

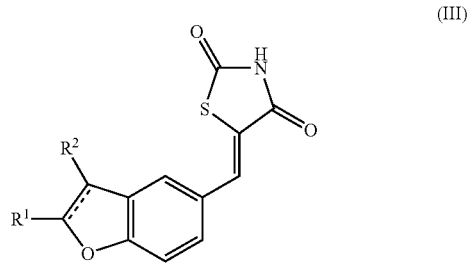
(III)

as well as its geometrical isomers, its optically active forms as enantiomers, diastereomers and its racemate forms, as well as pharmaceutically acceptable salts and pharmaceutically active derivatives thereof, wherein $R^1$ and $R^2$ are as above defined (the dotted line represents the optional presence of a double bond).

Still a further embodiment comprises compounds of formulae (IV), (V) and (VI):

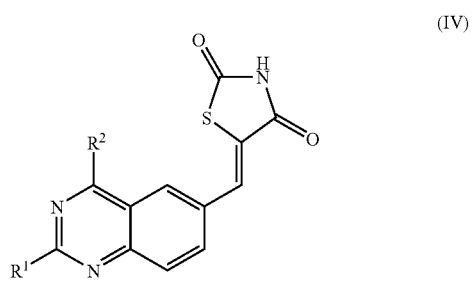
(IV)

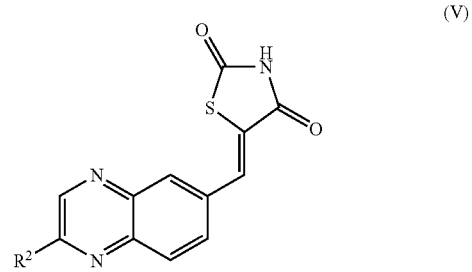
(V)

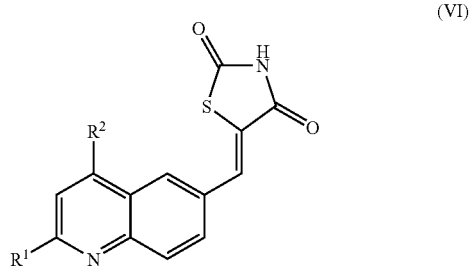
(VI)

$R^1$ is selected from the group consisting of hydrogen, halogen, cyano, $C_1$-$C_6$-alkyl, $C_1$-$C_6$-alkoxy, acyl, alkoxy cabonyl, while $R^2$ is as above defined. In a specific embodiment $R^2$ is an amino moiety.

A further aspect of the present invention is the use of the novel compounds of formulae (II), (II-a), (III), (IV), (V) or (VI) as medicament.

Another further aspect of the invention is a pharmaceutical composition containing at least one thiazolidinone-vinyl fused-benzene derivative according to formulae (II), (III), (IV), (V) or (VI) and a pharmaceutically acceptable carrier, diluent or excipient thereof.

Still a further aspect of the invention is the use of compounds according to formula (II), (III), (IV), (V) or (VI) for the preparation of a medicament for the prophylaxis and/or treatment of diseases mediated by a PI3 Kinase, particularly PI3 Kinase γ.

Specific diseases are the ones selected in the group comprising or consisting of autoimmune disorders and/or inflammatory diseases, cardiovascular diseases, neurodegenerative diseases, bacterial or viral infections, kidney diseases, platelet aggregation, cancer, transplantation complications due to rejection reactions, graft rejection or lung injuries.

In a preferred embodiment, said compounds are useful for the treatment and/or prophylaxis of autoimmune diseases or inflammatory diseases such as multiple sclerosis, psoriasis, rheumatoid arthritis, systemic lupus erythematosis, inflammatory bowel disease, lung inflammation, thrombosis or brain infection/inflammation such as meningitis or encephalitis.

In another preferred embodiment according to the invention, these compounds are useful for the treatment and/or prophylaxis of neurodegenerative diseases including multiple sclerosis, Alzheimer's disease, Huntington's disease, CNS trauma, stroke or ischemic conditions.

In a particularly preferred embodiment according to the invention, these compounds are useful for the treatment and/or prophylaxis of cardiovascular diseases such as atherosclerosis, heart hypertrophy, cardiac myocyte dysfunction, elevated blood pressure or vasoconstriction.

In another particularly preferred embodiment according to the invention, these compounds are useful for the treatment and/or prophylaxis of chronic obstructive pulmonary disease, anaphylactic shock fibrosis, psoriasis, allergic diseases, asthma, stroke or ischemic conditions, ischemia-reperfusion, platelets aggregation/activation, skeletal muscle atrophy/hypertrophy, leukocyte recruitment in cancer tissue, angiogenesis, invasion metastisis, in particular melanoma, Karposi's sarcoma, acute and chronic bacterial and viral infections, sepsis, transplantation complications due to rejection reactions, graft rejection, glomerulo sclerosis, glomerulo nephritis, progressive renal fibrosis, endothelial and epithelial injuries in the lung or in general lung airways inflammation.

According to the present invention, compounds of formula (II), (II-a), (III) (IV), (V) or (VI) are suitable to modulate, particularly to inhibit, PI3 kinase activity and more particularly PI3Kγ activity.

Still a further object of the present invention is a process for preparing azolidinone-vinyl fused-benzene derivatives according to formula (I), (Ia), (Ib), (Ic) or (Id) but also thiazolidinone-vinyl fused-benzene derivatives of formulae (II), (II-a), (III), (IV), (V) or (VI).

The azolidinone-vinyl fused-benzene derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

In the process illustrated in the following schemes $R^1$, $R^2$, G, V, W, $Y^1$, $Y^2$, Z, m, n, o, p and q are each as above-defined in the description.

Generally, the azolidinone-vinyl fused-benzene derivatives according to the general formula (I) could be obtained by several synthetic approaches, using both solution-phase and solid-phase chemistry protocols (Brummond et. al., J.O.C., 64, 1723-1726 (1999)), either by conventional methods or by microwave-assisted techniques.

Scheme 1

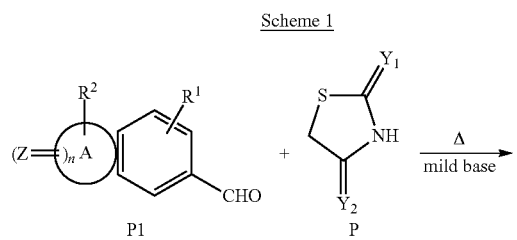

-continued

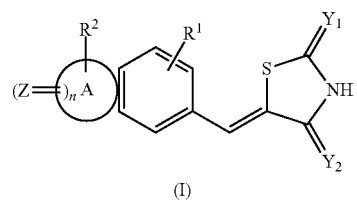

Scheme 2

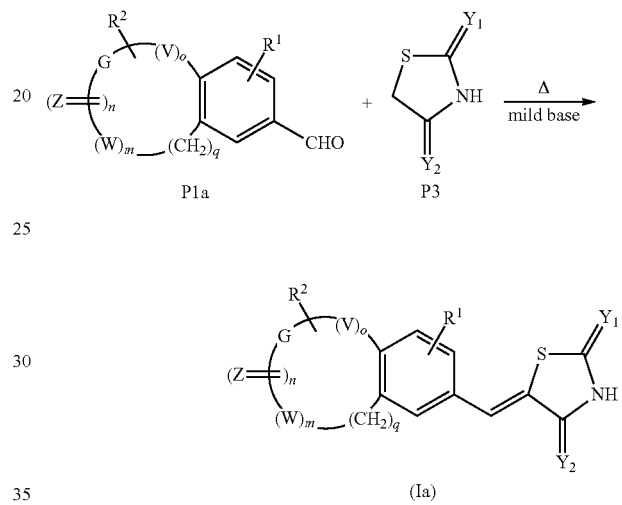

In a first step, approximately equimolar amounts of the aldehyde reactant P1 (P1a) and compound 2 (in particular thiazolidinedione or rhodanin P3) are heated in the presence of a preferably mild base to provide the corresponding olefin of formula (Ia). In the first step, P1a may be replaced by precursors P1b and P1c in order to obtain the final compounds (Ib) and (Ic) respectively as above described in the description.

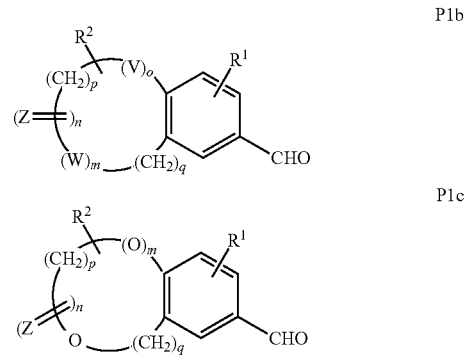

Particularly preferred process according to the invention are illustrated by the following schemes 3 and 4 in which compounds of formula (II) and (III) respectively, may be obtained using the same reaction as above-mentioned.

Scheme 3

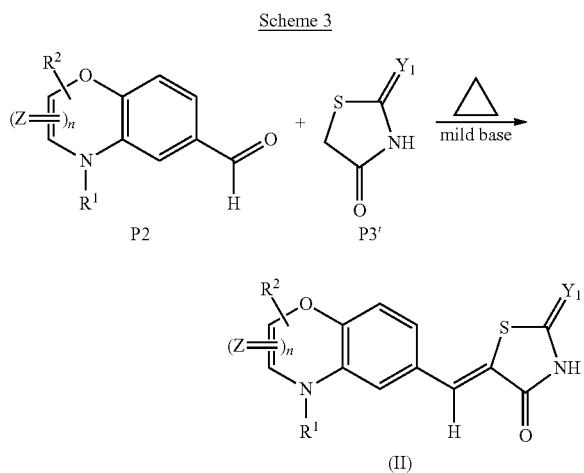

Scheme 4

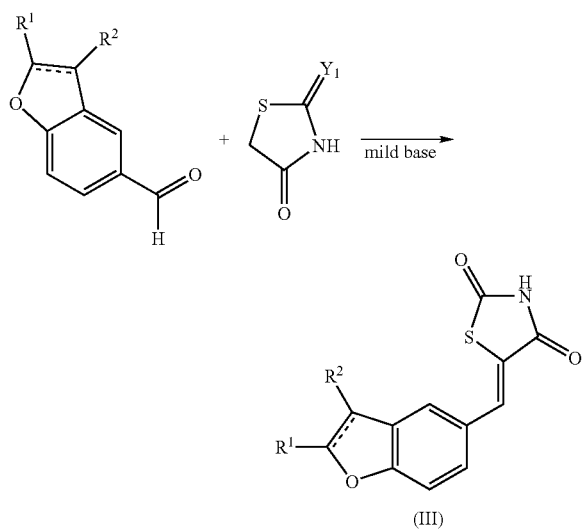

While this step may be carried out in the absence of a solvent at a temperature, which is sufficiently high to cause at least partial melting of the reaction mixture, it is preferably carried out in the presence of a inert solvent. A preferred temperature range is from about 100° C. to 250° C., and especially preferred is a temperature of from about 120° C. to 200° C. Examples of such solvents for the above reaction include solvents like dimethoxymethane, xylene, toluene, o-dichlorobenzene etc. Examples of suitable mild bases for the above reaction are alkali metal and alkaline earth salts of week acids such as the ($C_1$-$C_{12}$)-alkyl carboxylic acids and benzoic acid, alkali metal and alkaline earth carbonates and bicarbonates such as calcium carbonate, magnesium carbonate, potassium bicarbonate and secondary amines such as piperidine, morpholine as well as tertiary amines such as pyridine, triethylamine, diisopropylethylamine, N-methylmorpholine, N-ethylpiperidine, N-methylpiperidine and the like. Especially preferred mild bases are sodium acetate or piperidine for reasons of economy and efficiency.

In a typical such reaction (Tietze et. al., in "The Knoevenagel reaction", p. 341 ff., Pergamon Press, Oxford 1991, Eds.: Trost B. M., Fleming I.) the aldehyde starting material P1a and the other starting compound (e.g. thiazolidinedione) P3 are combined in approximately equimolar amounts with 0.5 to one equivalent of piperidine in dimethoxymethane or similar solvent and heated between 120 and 200° C. at which the reaction is substantially complete in from about 15 minutes to 3 hours. The desired olefin of formula (Ia) is then isolated by filtration, in case it precipitated out of the reaction mixture upon cooling, or for example, by mixing with water and subsequent filtration, to obtain the crude product, which is purified, if desired, e.g. by crystallization or by standard chromatographic methods.

Alternatively compounds of formula (Ia) may be obtained typically by mixing equimolar amounts of thiazolidinedione P3 with aldehyde P1a and molar excess, preferably a 2-4 fold excess, of anhydrous sodium acetate and the mixture is heated at a temperature high enough to effect melting, at which temperature the reaction is mainly complete in from 5 to 60 minutes.

Preferably the above reaction is carried out in acidic media such as acetic acid in the presence of sodium acetate or beta-alanine.

Above described reactions may be carried out alternatively under microwave conditions as heating source. Typically the aldehyde starting material P1a and thiazolidinedione P3 are combined in approximately equimolar amounts with 0.5 to one equivalent of piperidine in dimethoxymethane or similar solvent and heated between 140° C. and 240° C. at which the reaction is substantially complete in from 3 to 10 minutes.

The pharmaceutically acceptable cationic salts of compounds of the present invention are readily prepared by reacting the acid forms with an appropriate base, usually one equivalent, in a co-solvent. Typical bases are sodium hydroxide, sodium methoxide, sodium ethoxide, sodium hydride, potassium hydroxide, potassium methoxide, magnesium hydroxide, calcium hydroxide, benzathine, choline, diethanolamine, ethylenediamine, meglumine, benethamine, diethylamine, piperazine and tromethamine. The salt is isolated by concentration to dryness or by addition of a non-solvent. In some cases, salts can be prepared by mixing a solution of the acid with a solution of the cation (sodium ethylhexanoate, magnesium oleate), employing a solvent in which the desired cationic salt precipitates, or can be otherwise isolated by concentration and addition of a non-solvent.

2,4-Azolidinone derivatives P3 are commercially available from various sources. The aldehydes of formula PI a are prepared by a variety of well known methods, for example starting from the corresponding carboxylic acid alkyl ester or carboxylic acid by oxido-reduction, using standard techniques to reduce carboxylic acid alkyl ester or carboxylic acid to benzylic alcohols with lithium aluminium hydride, diisopropylaluminum etc. and ultimately re-oxidize the corresponding benzylic alcohol to the corresponding aldehyde by mild oxidation with reagents such as manganese dioxide, chromic acid, Dess-Martin reagent or Swern oxidation, or under conditions known to produce aldehydes from primary alcohols. An alternative way may be the direct reduction of the corresponding carboxylic acid alkyl ester or carboxylic acid to the corresponding aldehyde, using DIBAL at low temperature or any other techniques known in the field.

Scheme 5

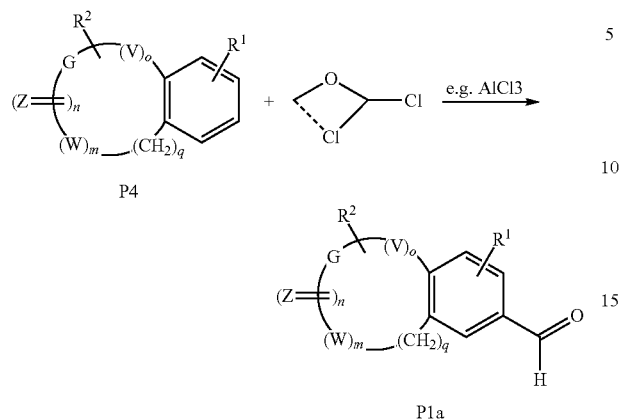

An alternative way to prepare the appropriate aldehydes is the selective reduction of a nitrile moiety to the corresponding aldehyde using known methods like e.g. DIBAL etc. Another way to access aldehydes of formula P1a is the selective reduction of the corresponding acyl chloride using e.g. Lithiumaluminium-tri-tert-butoxyhydride (Cha J. S., Brown H. C., *J.O.C* 1993, 58, p. 4732-34). Another alternative way to produce the appropriate aldehydes is the reaction of the corresponding benzene derivative in a Friedl-Crafts type of reaction wherein the substrate P4 as shown in the above scheme 5 is reacted with 1,1-dichloromethylmethyl ether in the presence of a Lewis acid such as titanium tetrachloride or aluminium trichloride or any corresponding Lewis acids suitable for such type of reaction.

According to a more particularly preferred process of the invention, as described in the literature (Petrov O. I., Kalcheva V. B., Antonova A. T., *Collect. Czech. Chem. Commun*, 62, p. 494-7 (1997)) and illustrated by Scheme 6 hereinafter, reactant P2 may be obtained starting from P5 by reacting with 1,1-dichloromethylmethyl ether as above-described.

Scheme 6

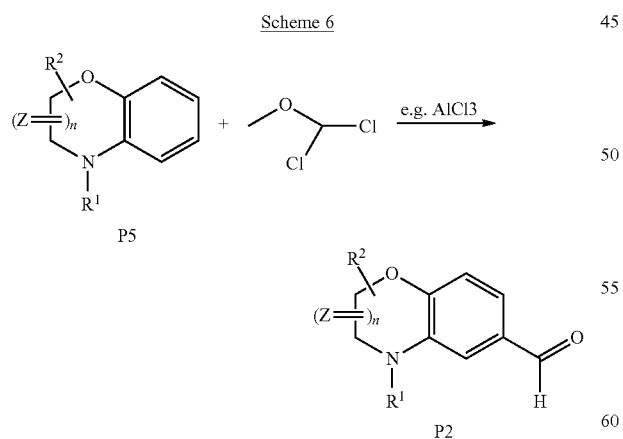

According to another more particularly preferred process of the invention, as illustrated by Scheme 7 hereinafter, reactant P6 may be obtained starting from P7 by reacting with DMF and the presence of magnesium or n-butyl-lithium or any other method known to the person skilled in the art.

Scheme 7

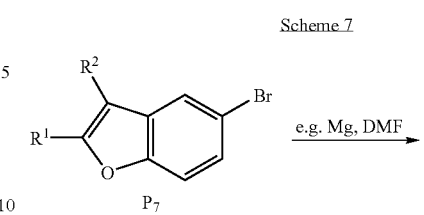

According to another more particularly preferred process of the invention, as illustrated by Scheme 8 hereinafter, reactant P6 may be obtained starting from P9 by reacting n-butyllithium or LDA in the presence of an appropriate electrophile $R^1$—X, or any other method known to the person skilled in the art. This method may be repeated for P8 in order to obtain P6 accordingly.

Scheme 8

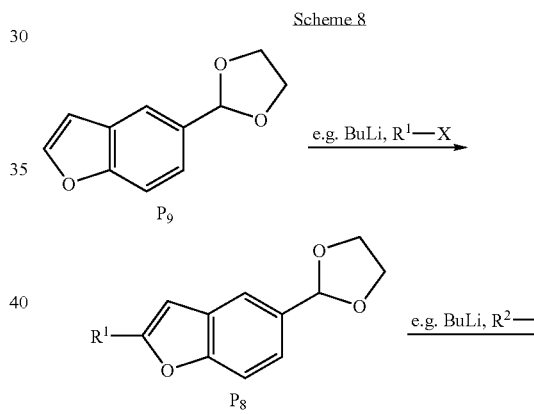

Similarly, saturated precursors P6 may be obtained in a one-pot reaction using P9 and appropriate electrophiles $R^1$—X and $R^2$—X as set out in Scheme 9.

Scheme 9

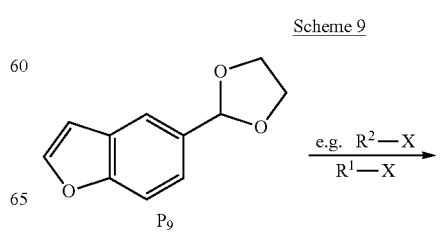

-continued

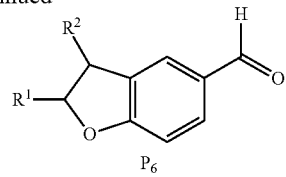

P₆

If the above set out general synthetic methods are not applicable to obtain compounds according to formula (I) and/or to necessary intermediates for the synthesis of compounds of formula (I), suitable methods of preparation known by a person skilled in the art should be used. In general, the synthesis pathways for any individual compound of formula (I) will depend on the specific substitutents of each molecule and upon the ready availability of intermediates necessary; again such factors being appreciated by those of ordinary skill in the art.

For all the protection and deprotection methods, see Philip J. Kocienski, in "*Protecting Groups*", Georg Thieme Verlag Stuttgart New York, 1994 and, Theodora W. Greene and Peter G. M. Wuts in "*Protective Groups in Organic Synthesis*", Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of the present invention which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of the present invention with a suitable base. Both types of salts may be formed or interconverted using ion-exchange resin techniques.

When employed as pharmaceuticals, azolidinedione-vinyl fused-benzene derivatives of the present invention are typically administered in the form of a pharmaceutical composition. Hence, pharmaceutical compositions comprising a compound of the present invention a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing azolidinedione-vinyl fused-benzene derivatives of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, transdermal, subcutaneous, intravenous, intramuscular and intranasal. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the thiazolidinedione-vinyl fused-benzene derivative is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the thiazolidinedione-vinyl fused-benzene derivatives of formula (I) in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein by reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention. The following abbreviations are hereinafter used in the accompanying examples: min (minute), hr (hour), g (gram), mmol (millimole), m.p. (melting point), eq (equivalents), ml (milliliter), μl (microliters), ACN (acetonitrile), Boc (butoxycarbonyl), Cbz (carboxybenzyl), CDCl₃ (deuterated chloroform), cHex (cyclohexane), dba (dibenzylideneacetone), DCM (dichloromethane), DEAD (diethylazodicarboxylate, DIC (diisopropylcarbodiimide), DIEA (diisopropylethylamine), DMAP (4-dimethylaminopyridine), DME (dimethoxyethane), DMF (dimethylformamide), DMSO (dimethylsulfoxide), DMSO-d$_6$ (deuterated dimethylsulfoxide), EDC (1-(3-dimethylaminopropyl)-3-ethylcarbodiimide hydrochloride), EtOAc (ethylacetate), Et$_2$O (diethylether), Fmoc (9-fluorenylmethoxy-carbonyl), HOBt (1-hydroxybenzotriazole), K$_2$CO$_3$ (potassium carbonate), MgSO$_4$ (magnesium sulfate), MsCl (methylsulfonylchloride), MTBE (tert-butylmethylether), NaH (sodium hydride), NaHCO$_3$ (sodium bicarbonate), nBuLi (n-butyllithium), PCC (pyridinium chlorochroinate), PE (petroleum ether), QCl (tetrabutylammonium chloride), rt (room temperature), TBTU (O-benzotriazolyl-N,N,N',N'-tetramethyluronium-tetrafluoroborate), TEA (triethylamine), TFA (trifluoroacetic acid), THF (tetrahydrofuran), TMOF (trimethylorthoformate), TMAD (N,N,N',N'-tetramethylazodicarboxamide), TosCl (toluenesulfonylchloride).

EXAMPLES

The following list of compounds were synthesized according to the below mentioned methods:

| Example | Name |
|---|---|
| 1 | 5-(1,3-benzodioxol-5-ylmethylene)-1,3-thiazolidine-2,4-dione |
| 2 | 5-(1,3-benzodioxol-5-ylmethylene)-2-thioxo-1,3-thiazolidin-4-one |
| 3 | 5-(2,3-dihydro-1,4-benzodioxin-6-ylmethylene)-1,3-thiazolidine-2,4-dione |
| 4 | 5-(2,3-dihydro-1-benzofuran-5-ylmethylene)-1,3-thiazolidine-2,4-dione |
| 5 | 5-[(7-methoxy-1,3-benzodioxol-5-yl)methylene]-1,3-thiazolidine-2,4-dione |
| 6 | 5-[(9,10-dioxo-9,10-dihydroanthracen-2-yl)methylene]-1,3-thiazolidine-2,4-dione |
| 7 | (5-[(2,2-difluoro-1,3-benzodioxol-5-yl)methylene]-1,3-thiazolidine-2,4-dione |
| 8 | (5Z)-5-(1,3-dihydro-2-benzofuran-5-ylmethylene)-1,3-thiazolidine-2,4-dione |
| 9 | 5-(1-benzofuran-5-ylmethylene)-1,3-thiazolidine-2,4-dione |
| 10 | 5-[(4-methyl-3-oxo-3,4-dihydro-2H-1,4-benzoxazin-6-yl)methylene]-1,3-thiazolidine-2,4-dione |
| 11 | 5-(1,3-benzodioxol-5-ylmethylene)-2-imino-1,3-thiazolidin-4-one |
| 12 | 5-Quinolin-6-ylmethylene-thiazolidine-2,4-dione |
| 13 | 5-Quinolin-6-ylmethylene-2-thioxo-thiazolidine-4-one |
| 14 | 2-Imino-5-quinolin-6-ylmethylene-thiazolidine-4-one |
| 15 | 5-(3-Methyl-benzo[d]isoxazol-5-ylmethylene)-thiazolidine-2,4-dione |
| 16 | 5-(4-Phenyl-quinazolin-6-ylmethylene)-thiazolidine-2,4-dione |
| 17 | 5-(4-Dimethylamino-quinazolin-6-ylmethylene)-thiazolidine-2,4-dione |
| 18 | 5-[(4-aminoquinazolin-6-yl)methylene]-1,3-thiazolidine-2,4-dione |
| 19 | 5-[(4-piperidin-1-ylquinazolin-6-yl)methylene]-1,3-thiazolidine-2,4-dione |
| 20 | 5-[(4-morpholin-4-ylquinazolin-6-yl)methylene]-1,3-thiazolidine-2,4-dione |
| 21 | 5-{[4-(benzylamino)quinazolin-6-yl]methylene}-1,3-thiazolidine-2,4-dione |
| 22 | 5-{[4-(diethylamino)quinazolin-6-yl]methylene}-1,3-thiazolidine-2,4-dione |
| 23 | 5-({4-[(pyridin-2-ylmethyl)amino]quinazolin-6-yl}methylene)-1,3-thiazolidine-2,4-dione |
| 24 | 5-({4-[(pyridin-3-ylmethyl)amino]quinazolin-6-yl}methylene)-1,3-thiazolidine-2,4-dione |
| 25 | ethyl 1-{6-[(2,4-dioxo-1,3-thiazolidin-5-ylidene)methyl]quinazolin-4-yl}piperidine-3-carboxylate |
| 26 | ethyl 1-{6-[(2,4-dioxo-1,3-thiazolidin-5-ylidene)methyl]quinazolin-4-yl}piperidine-4-carboxylate |
| 27 | tert-butyl 1-{6-[(2,4-dioxo-1,3-thiazolidin-5-ylidene)methyl]quinazolin-4-yl}-L-prolinate |
| 28 | 5-{[4-(4-methylpiperazin-1-yl)quinazolin-6-yl]methylene}-1,3-thiazolidine-2,4-dione |
| 29 | 5-{[4-(4-pyrimidin-2-ylpiperazin-1-yl)quinazolin-6-yl]methylene}-1,3-thiazolidine-2,4-dione |
| 30 | 5-({4-[4-(4-fluorophenyl)piperidin-1-yl]quinazolin-6-yl}methylene)-1,3-thiazolidine-2,4-dione |
| 31 | 5-{[4-(4-benzylpiperidin-1-yl)quinazolin-6-yl]methylene}-1,3-thiazolidine-2,4-dione |
| 32 | 5-({4-[4-(2-phenylethyl)piperidin-1-yl]quinazolin-6-yl}methylene)-1,3-thiazolidine-2,4-dione |
| 33 | 5-{[4-(4-methylpiperidin-1-yl)quinazolin-6-yl]methylene}-1,3-thiazolidine-2,4-dione |
| 34 | 5-{[4-(4-hydroxypiperidin-1-yl)quinazolin-6-yl]methylene}-1,3-thiazolidine-2,4-dione |
| 35 | 1-[6-(2,4-Dioxo-thiazolidin-5-ylidenemethyl)-quinazolin-4-yl]-piperidine-4-carboxylic acid |
| 36 | 1-[6-(2,4-Dioxo-thiazolidin-5-ylidenemethyl)-quinazolin-4-yl]-piperidine-3-carboxylic acid |
| 37 | 1-[6-(2,4-Dioxo-thiazolidin-5-ylidenemethyl)-quinazolin-4-yl]-pyrrolidine-2-carboxylic acid |
| 38 | 5-(4-Methylamino-quinazolin-6-ylmethylene)-thiazolidine-2,4-dione |
| 39 | 5-(4-Methoxy-quinazolin-6-ylmethylene)-thiazolidine-2,4-dione |
| 40 | 2-Imino-5-(4-methylamino-quinazolin-6-ylmethylene)-thiazolidin-4-one |
| 41 | 2-Imino-5-(4-piperidine-quinazolin-6-ylmethylene)-thiazolidin-4-one |
| 42 | 2-Imino-5-(4-dimethylamino-quinazolin-6-ylmethylene)-thiazolidin-4-one |
| 43 | 5-(2-Methyl-2H-benzotriazol-5-ylmethylene)-thiazolidine-2,4-dione |
| 44 | 5-(3-Methyl-3H-benzotriazol-5-ylmethylene)-thiazolidine-2,4-dione |
| 45 | 5-(3-Ethyl-3H-benzoimidazol-5-ylmethylene)-thiazolidine-2,4-dione |

-continued

| Example | Name |
|---|---|
| 46 | 5-{[1-(4-phenylbutyl)-1H-benzimidazol-6-yl]methylene}-1,3-thiazolidine-2,4-dione |
| 47 | 5-[(1-prop-2-yn-1-yl-1H-benzimidazol-6-yl)methylene]-1,3-thiazolidine-2,4-dione |
| 48 | 5-[(1-{2-[4-(trifluoromethyl)phenyl]ethyl}-1H-benzimidazol-6-yl)methylene]-1,3-thiazolidine-2,4-dione |
| 49 | 5-({1-[2-(4-hydroxyphenyl)ethyl]-1H-benzimidazol-6-yl}methylene)-1,3-thiazolidine-2,4-dione |
| 50 | methyl 4-{6-[(2,4-dioxo-1,3-thiazolidin-5-ylidene)methyl]-1H-benzimidazol-1-yl}cyclohexanecarboxylate |
| 51 | 5-({1-[2-(5-methoxy-1H-indol-3-yl)ethyl]-1H-benzimidazol-6-yl}methylene)-1,3-thiazolidine-2,4-dione |
| 52 | 5-({1-[(1-methyl-1H-pyrazol-4-yl)methyl]-1H-benzimidazol-6-yl}methylene)-1,3-thiazolidine-2,4-dione |
| 53 | 5-({1-[2-(3,4-dimethoxyphenyl)ethyl]-1H-benzimidazol-6-yl}methylene)-1,3-thiazolidine-2,4-dione |
| 54 | 5-({1-[2-(4-phenoxyphenyl)ethyl]-1H-benzimidazol-6-yl}methylene)-1,3-thiazolidine-2,4-dione |
| 55 | 5-({1-[4-(trifluoromethyl)benzyl]-1H-benzimidazol-6-yl}methylene)-1,3-thiazolidine-2,4-dione |
| 56 | 4-{6-[(2,4-dioxo-1,3-thiazolidin-5-ylidene)methyl]-1H-benzimidazol-1-yl}cyclohexanecarboxylic acid |
| 57 | 5-[(1-isobutyl-1H-benzimidazol-6-yl)methylene]-1,3-thiazolidine-2,4-dione |
| 58 | 5-({1-[2-(1,3-benzodioxol-4-yl)ethyl]-1H-benzimidazol-6-yl}methylene)-1,3-thiazolidine-2,4-dione |
| 59 | 5-({1-[2-(2-phenoxyphenyl)ethyl]-1H-benzimidazol-6-yl}methylene)-1,3-thiazolidine-2,4-dione |
| 60 | 5-{[1-(3,3-diphenylpropyl)-1H-benzimidazol-6-yl]methylene}-1,3-thiazolidine-2,4-dione |
| 61 | 5-{[1-(2-methoxybenzyl)-1H-benzimidazol-6-yl]methylene}-1,3-thiazolidine-2,4-dione |
| 62 | 5-{[1-(3-furylmethyl)-1H-benzimidazol-6-yl]methylene}-1,3-thiazolidine-2,4-dione |
| 63 | 5-[(1-propyl-1H-benzimidazol-6-yl)methylene]-1,3-thiazolidine-2,4-dione |
| 64 | 5-Quinoxalin-6-ylmethylene-thiazolidine-2,4-dione |
| 65 | 5-Quinoxalin-6-ylmethylene-2-thioxo-thiazolidin-4-one |
| 66 | 2-Imino-5-quinoxalin-6-ylmethylene-thiazolidin-4-one |
| 67 | 5-Benzothiazol-6-ylmethylene-thiazolidine-2,4-dione |
| 68 | 5-(3-Methyl-benzofuran-5-ylmethylene)-thiazolidine-2,4-dione |
| 69 | 5-(2-Bromo-3-methyl-benzofuran-5-ylmethylene)-thiazolidine-2,4-dione |
| 70 | 5-(3-bromo-benzofuran-5-ylmethylene)-thiazolidine-2,4-dione |
| 71 | 3-[5-(2,4-Dioxo-thiazolidin-5-ylidenemethyl)-benzofuran-3-yl]-acrylic acid ethyl ester |
| 72 | 3-[5-(2,4-Dioxo-thiazolidin-5-ylidenemethyl)-benzofuran-3-yl]-acrylic acid |
| 73 | 5-[3-(3-Oxo-3-piperidin-1-yl-propenyl)-benzofuran-5-ylmethylene]-thiazoli-dine-2,4-dione |
| 74 | Methyl 1-((3-{5-[(2,4-dioxo-1,3-thiazolidin-5-ylidene)methyl]-1-benzofuran-3-yl}prop-2-enoyl)prolinate |
| 75 | Methyl 1-((3-{5-[(2,4-dioxo-1,3-thiazolidin-5-ylidene)methyl]-1-benzofuran-3-yl}prop-2-enoyl)-D-prolinate |
| 76 | (5-({3-[(3-oxo-3-pyrrolidin-1-ylprop-1-en-1-yl]-1-benzofuran-5-yl}methylene)-1,3-thiazolidine-2,4-dione |
| 77 | 5-({3-[3-morpholin-4-yl-3-oxoprop-1-en-1-yl]-1-benzofuran-5-yl}methylene)-1,3-thiazolidine-2,4-dione |
| 78 | Methyl 1-(3-{5-[(2,4-dioxo-1,3-thiazolidin-5-ylidene)methyl]-1-benzofuran-3-yl}prop-2-enoyl)-L-prolinate |
| 79 | N-cyclohexyl-3-{5-[(2,4-dioxo-1,3-thiazolidin-5-ylidene)methyl]-1-benzofuran-3-yl}-N-methylacrylamide |
| 80 | 3-{5-[(2,4-dioxo-1,3-thiazolidin-5-ylidene)methyl]-1-benzofuran-3-yl}-N-ethyl-N-(2-hydroxyethyl)acrylamide |
| 81 | N-cyclobutyl-3-{5-[(2,4-dioxo-1,3-thiazolidin-5-ylidene)methyl]-1-benzofuran-3-yl}acrylamide |
| 82 | 5-({3-[3-azetidin-1-yl-3-oxoprop-1-en-1-yl]-1-benzofuran-5-yl}methylene)-1,3-thiazolidine-2,4-dione |
| 83 | 5-({3-[3-(1,3-dihydro-2H-isoindol-2-yl)-3-oxoprop-1-en-1-yl]-1-benzofuran-5-yl}methylene)-1,3-thiazolidine-2,4-dione |
| 84 | 5-({3-[3-azepan-1-yl-3-oxoprop-1-en-1-yl]-1-benzofuran-5-yl}methylene)-1,3-thiazolidine-2,4-dione |
| 85 | 3-{5-[(2,4-dioxo-1,3-thiazolidin-5-ylidene)methyl]-1-benzofuran-3-yl}-N-piperidin-1-ylacrylamide |
| 86 | 3-{5-[(2,4-dioxo-1,3-thiazolidin-5-ylidene)methyl]-1-benzofuran-3-yl}-N-(pyridin-3-ylmethyl)acrylamide |
| 87 | N-cyclohexyl-3-{5-[(2,4-dioxo-1,3-thiazolidin-5-ylidene)methyl]-1-benzofuran-3-yl}acrylamide |
| 88 | 5-({3-[3-(4-methylpiperazin-1-yl)-3-oxoprop-1-en-1-yl]-1-benzofuran-5-yl}methylene)-1,3-thiazolidine-2,4-dione |
| 89 | N-cycloheptyl-3-{5-[(2,4-dioxo-1,3-thiazolidin-5-ylidene)methyl]-1-benzofuran-3-yl}acrylamide |

| Example | Name |
|---|---|
| 90 | 5-({3-[3-(2,5-dihydro-1H-pyrrol-1-yl)-3-oxoprop-1-en-1-yl]-1-benzofuran-5-yl}methylene)-1,3-thiazolidine-2,4-dione |
| 91 | N-cyclopentyl-3-{5-[(2,4-dioxo-1,3-thiazolidin-5-ylidene)methyl]-1-benzofuran-3-yl}acrylamide |
| 92 | 3-[5-(2,4-Dioxo-thiazolidin-5-ylidenemethyl)-benzofuran-3-yl]-propionic acid ethyl ester |
| 93 | 3-[5-(2,4-Dioxo-thiazolidin-5-ylidenemethyl)-benzofuran-3-yl]-propionic acid |
| 94 | 5-[3-(3-Oxo-3-piperidin-1-yl-propyl)-benzofuran-5-ylmethylene]-thiazol-idine-2,4-dione |
| 95 | 6-(2,4-Dioxo-thiazolidin-5-ylidenemethyl)-2,3-dihydro-benzo[1,4]oxazine-4-carboxylic acid tert-butyl ester |
| 96 | 5-(3,4-Dihydro-2H-benzo[1,4]oxazin-6-ylmethylene)-thiazolidine-2,4-dione |
| 97 | 5-(4-Benzoyl-3,4-dihydro-2H-benzo[1,4]oxazin-6-ylmethylene)-thiazolidine-2,4-dione |
| 98 | 5-(4-Acetyl-3,4-dihydro-2H-benzo[1,4]oxazin-6-ylmethylene)-thiazolidine-2,4-dione |
| 99 | 6-(2,4-Dioxo-thiazolidin-5-ylidenemethyl)-benzo[1,4]oxazine-4-carboxylic acid tert-butyl ester |
| 100 | [6-(2,4-Dioxo-thiazolidin-5-ylidenemethyl)-3-oxo-2,3-dihydro-benzo[1,4]-oxazin-4-yl]-acetic acid methyl ester |
| 101 | N-Benzyl-2-[6-(2,4-dioxo-thiazolidin-5-ylidenemethyl)-3-oxo-2,3-dihydro-benzo[1,4]oxazin-4-yl]-acetamide |
| 102 | 5-(4-Butyl-3-oxo-3,4-dihydro-2H-benzo[1,4]oxazin-6-ylmethylene)-thiazolidine-2,4-dione |
| 103 | 5-(4-Benzyl-3-oxo-3,4-dihydro-2H-benzo[1,4]oxazin-6-ylmethylene)-thiazolidine-2,4-dione |
| 104 | 5-(2-Chloro-benzofuran-5-ylmethylene)-thiazolidine-2,4-dione |
| 105 | 5-(3-Amino-benzo[d]isoxazol-5-ylmethylene)-thiazolidine-2,4-dione |
| 106 | 5-(3-Phenylethynyl-benzofuran-5-ylmethylene)-thiazolidine-2,4-dione |
| 107 | 5-Benzo[1,2,5]thiadiazol-5-ylmethylene-thiazolidine-2,4-ione |
| 108 | 5-Benzo[1,2,5]oxadiazol-5-ylmethylene-thiazolidine-2,4-ione |
| 109 | 5-(2-Methyl-benzofuran-6-ylmethylene)-thiazolidine-2,4-dione |
| 110 | 5-(2-Carboxymethyl-benzofuran-6-ylmethylene)-thiazolidine-2,4-dione |
| 111 | 5-(3-Bromo-2-fluoro-2,3-dihydro-benzofuran-6-ylmethylene)-thiazolidine-2,4-dione |
| 112 | 5-(2-Fluoro-benzofuran-6-ylmethylene)-thiazolidine-2,4-dione |

The following intermediate aldehydes are commercially available: 2,2-Difluoro-1,3-benzodioxole-5-carboxaldehyde, 1,3-Benzodioxole-5-carboxaldehyde, 1,4-Benzodioxan-6-carboxaldehyde, 9,10-Dioxo-9,10-dihydro-anthracene-2-carbaldehyde, 2,3-Dihydro-benzo[b]furan-5-carboxaldehyde, 3-Methoxy-4,5-methylenedioxybenzaldehyde.

Thiazolidinedione and Rhodanine are commercially available. Intermediate aldehydes were synthesized according to the protocols as mentioned below.

The HPLC, NMR and MS data provided in the examples described below were obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The purifications were obtained as followed: Preparative HPLC Waters Prep LC 4000 System equipped with columns Prep Nova-Pak™HR C186 µm 60 Å, 40×30 mm (up to 100 mg) or 40×300 mm (up to 1 g). All the purifications were performed with a gradient of MeCN/H$_2$O 0.09% TFA.

Intermediate 1: Preparation of 5-formyl-1-benzofuran

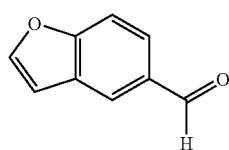

Step I Ethyl-2-formyl-4-bromophenoxy acetate

A mixture of 5-bromosalicylaldehyde (50 g, 0.248 mol), ethylbromoacetate (42 g, 0.248 mol) and K$_2$CO$_3$ (68 g, 0.49 mol) in dry DM (200 mL) was stirred at RT for 12 h. The reaction mixture was filtered and filtrate diluted with water. The mixture was extracted with diethylether (4×200 mL), washed with brine and concentrated to give crude ethyl-2-formyl-4-bromophenoxy acetate (64 g, 90%) as a solid.

Step II: 4-Bromo-2-formylphenoxy acetic acid

A mixture of ethyl-2-formyl-4-bromophenoxy acetate (60 g, 0.209 mol), LiOH (7.5 g, 0.31 mol), THF (250 mL) and water (100 mL) was stirred at RT for 24 h. The reaction mixture was concentrated under reduce pressure and residue acidified with 1.5N HCl to pH=2. The solid precipitate obtained was filtered and dried to give 4-bromo-2-formylphenoxy acetic acid (50 g, 94%).

Step III: 5-Bromo-1-benzofuran

To a mixture of 2-formyl-4-bromophenoxy acetic acid (50 g, 0.192 mol), sodium acetate (100 g, 1.21 mol) in acetic acid (250 mL) at 100° C. was added acetic anhydride (100 mL) portions during a period of 3 h. The reaction mixture was then refluxed for 20 h. The solvent was removed by distillation and residue diluted with 3N HCl (500 mL) and refluxed for 2 h. The reaction mixture was then concentrated under vacuum and product extracted with pet. ether (3×200 mL). The organic layer was washed with 10% NaHCO$_3$ solution and evaporated to give 5-bromo-1-benzofuran (15 g, 40%) as a pale yellow liquid.

Step IV: 5-Formyl-1-benzofuran (P1a in scheme 2 for example 9)

A mixture of 5-bromo-1-benzofuran (0.5 g), Mg (0.92 g, 0.038 mol), I$_2$ (1 crystal) in dry THF (2.5 mL) under N$_2$ atmosphere was refluxed for 30 min. To this was added a solution of 5-bromo-1-benzofuran (4.5 g) in 25 mL of dry THF) as soon as the 12 color disappear and refluxed for another 2 h. The reaction mixture was then cooled to −40° C. and added dry DMF (3.6 g) drop-wise and slowly warmed to RT for a period of 12 h. The reaction mixture was then cooled to 0° C. and acidified with 3N HCl to pH=2 and stirred for 30 min. The reaction mixture was then diluted with water (500 mL), extracted with ethylacetate (2×200 mL), washed with brine and dried. The solvent was removed under vacuum and purified by column chromatography over silica gel (pet. ether/CH$_2$Cl$_2$) to give 5-formyl-1-benzofuran (2 g, 54%) as a liquid. LC-MS: M/Z ESI: 1.47 min, 147.34 (M+1).

Intermediate 2: Preparation of 4-Methyl-3-oxo-3,4-dihydro-2H-benzo[1,4]oxazine-6-carbaldehyde

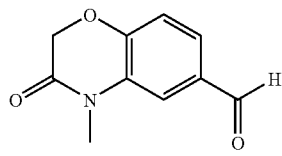

Step I: 2-(N-methylamino)-phenol 1 g of benzoxazole was dissolved in 20 ml of THF. 0.9 g of NaBH$_4$ were added under nitrogen and stirring. The suspension was cooled to 0° C. and 0.86 ml of acetic acid dissolved in 5 ml THF were slowly added, keeping the reaction temperature below 5° C. The reaction was stirred at 0° C. for 30 minutes and for further 12 hours at room temperature. The reaction mixture was again cooled to 0° C. and 50 ml of sat. NH$_4$Cl solution were added carefully. The phases were separated and the aqueous layer extracted twice with EtOAc. The combined organic layers were washed with brine, dried over MgSO$_4$ and filtered. Removal of the solvent afforded 0.97 g (of pure 2-(N-methylamino)-phenol.

Step II: 4-Methyl-4H-benzo[1,4]oxazin-3-one 1 g of 2-(N-methylamino)-phenol were dissolved in chloroform, followed by the addition of 10 ml of sat. NaHCO$_3$ in water. To this suspension was added slowly under vigorous stirring a solution of 1 g of 2-chloroacetylchloride in acetone. The reaction mixture was stirred for 2 hours at room temperature. The layers were separated. The organic layer was washed with water and dried over Na$_2$SO$_4$. After evaporating the solvent, the red oil was taken up in 30 ml DMF and 1 g of K$_2$CO$_3$ were added and the slurry was heated at 70° C. for additional 2 hours. The cyclization was followed by TLC. 200 ml of EtOAc were added and the organic layer was washed 3× with 0.1N HCl and 5× with brine. The remaining organic layer was dried over MgSO4 and filtrated. EtOAc was removed under reduced pressure affording 1.45 g of pure 4-methyl-4H-benzo[1,4]oxazin-3-one.

Step III: 4-Methyl-3-oxo-3,4-dihydro-2H-benzo[1,4]oxazine-6

1 g of AlCl$_3$ were suspended in 10 ml DCM, 0.5 ml of nitromethane were added to dissolve AlCl$_3$, and the solution was cooled to 0° C. 4-Methyl-4H-benzo[1,4]oxazin-3-one (0.5 g, 3.06 mmol) dissolved in DCM was added to the above solution and stirred for 15 minutes at 0° C. To this solution was further added 0.36 ml of bis-chloromethyl-methylether in DCM. The reaction was stirred at 0° C. for 15 minutes and at room temperature for 3 h. The crude reaction mixture was then poured onto ice, the layers were separated and the organic phase was washed with NaHCO$_3$ and brine. After drying over MgSO$_4$ and filtration the solvent was evaporated, which afforded 0.43 g of crude product. The dark oil was purified by flash chromatography using EtOAc and cyclohexane as eluents, affording 0.2 g (37%) of 4-methyl-3-oxo-3,4-dihydro-2H-benzo[1,4]oxazine-6-carbaldehyde as colourless solid.

HPLC: 2.07 min. LC-MS: M/Z ESI: 1.31 min, 192.28 (M+1).

Intermediate 3: Preparation of 4-methyl-3,4-dihydro-2H-benzo[1,4]oxazine-7-carbaldehyde

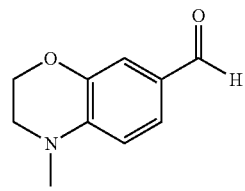

Step I: 4-Methyl-3,4-dihydro-2H-benzo[1,4]oxazine 0.97 g of 2-(N-methylamino)-phenol were dissolved in 50 ml acetone, followed by the addition of 2 g of K$_2$CO$_3$ dissolved in water. To this suspension was added slowly a solution of 2.66 g of dibromoethane in acetone. The reaction mixture was stirred for 22 hours under reflux. Acetone was evaporated and 200 ml of EtOAc were added and the organic layer was washed 3× with 0.1N HCl and 3× with brine. The remaining organic layer was dried over MgSO4 and filtrated. EtOAc was removed under reduced pressure affording 1 g of pure 4-methyl-3,4-dihydro-2H-benzo[1,4]oxazine.

Step II: 4-Methyl-3,4-dihydro-2H-benzo[1,4]oxazine-7-carbaldehyde

4-Methyl-3,4-dihydro-2H-benzo[1,4]oxazine dissolved in 200 ul DMF under Argon. POCl$_3$ was added under Argon. The reaction was heated and a closed vial at 90° C. for 75 min. 1 ml of NaAc in water was added and stirred while a brown oil was formed. The oil was extracted with DCM. The organic layer was washed with brine, dried and evaporated to dryness, affording 0.18 g (76%) of 4-methyl-3,4-dihydro-2H-benzo[1,4]oxazine-7-carbaldehyde as colourless solid.

LC-MS: M/Z ESI: 1.37 min, 178.35 (M+1).

Intermediate 4: Preparation of 1,3-Dihydroisobenzofuran-5-carbaldehyde

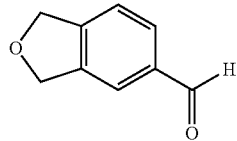

Step I (1,3-Dihydro-isobenzofuran-5-yl)-methanol

In a round bottom flask with reflux condenser were placed 1.0 g of 3-Prop-2-ynyloxy-propyne and 2.08 g of propargylic alcohol in 10 ml ethanol, followed by the addition of 9.8 mg of tris(triphenylphosphine)rhodium chloride (Wilkinson catalyst) at room temperature. The reaction was heated up to 70° C., while the reaction colour turned yellow rapidly. After 1 day stirring at r.t., TLC analysis showed complete conversion of the starting material. The solvent was evaporated, diluted with DCM and extracted with $H_2O$, dried over MgSO4. The brown mixture was purified by flash chromatography using 8/2 cyclohexane/AcOEt as mobile phase affording (1,3-Dihydro-isobenzofuran-5-yl)-methanol as a colourless pure solid (0.92 g, 60%).

Step II: 1,3-Dihydroisobenzofuran-5-carbaldehyde (1,3-Dihydro-isobenzofuran-5-yl)-methanol (440 mg, 2.9 mmol) was dissolved in 20 ml of DCM. 1,1,1-Triacetoxy-1,1-dihydro-1,2-benziodoxol-3(1H)-one (Dess-Martin reagent) (1.3 g, 3.2 mmol) was added and the reaction was stirred at r.t. for 4 h. The reaction mixture was diluted with ether and extracted 2× with NaOH 1N, 2× with $H_2O$ and dried over $MgSO_4$. The crude product was sufficiently pure and used without any further purification.

HPLC: 2.00 min. LC-MS: M/Z ESI: 1.50 min, 149.18 (M+1).

Intermediate 5: Preparation of Quinoline-6-carbaldehyde

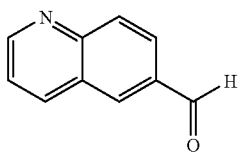

Step I: Quinolin-6-yl-methanol 5 g of methyl quinoline-6-carboxylate was dissolved in dry THF. Under Argon was added $LiAlH_4$ 1M in THF (2 eq.) at −20° C. The solution was stirred at that temperature for 1 h. Isopropanol was slowly added and the crude filtered through celite and washed with DCM. Concentration gave 3.6 g (85%) of pure alcohol.

HPLC: 1.10 min. LC-MS: M/Z ESI: 0.91 min, 160.43 (M+1).

Step II: Quinoline-6-carbaldehyde 2 g of quinolin-6-yl-methanol was dissolved in DCM. 15 g of MnO2 was added and the reaction mixture was stirred for 5 h. The crude filtered through celite and washed extensively with DCM. Concentration gave 1.85 g (93%) of pure aldehyde.

HPLC: 0.8 min. LC-MS: M/Z ESI: 1.07 min, 158.37 (M+1). $^1H$ NMR (DMSO-d6) δ 10.19 (s, 1H), 9.06 (t, J=3 Hz, 1H), 8.6-8.66 (m, 2H), 8.15 (s, 2H), 7.68 (dd, J=3 Hz, 9 Hz, 1H).

The following intermediate was synthesized accordingly using the suitable starting materials:

Intermediate 6: Preparation of 3-Methyl-benzo[d]isoxazole-5-carbaldehyde

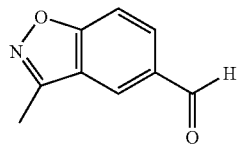

HPLC: 2.06 min. LC-MS: M/Z ESI: 1.26 min, 162.31 (M+1). $^1H$ NMR (DMSO-d6) δ 10.10 (s, 1H), 8.52 (s, 1H), 8.16 (d, J=12 Hz, 1H), 8.15 (s, 2H), 7.90 (d, J=9 Hz, 1H), 2.63 (s, 3H).

Intermediate 7: Preparation of 4-Chloro-quinazoline-6-carboxylic acid methyl ester

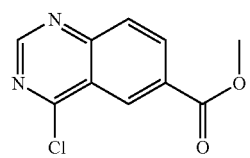

Step I: 4-Nitro isophthalic acid

A mixture of 3-methyl-4-nitrobenzoic acid (150 g, 0.825 mol), pyridine (1.5 L) and water (1.5 L) was heated to reflux. To the hot reaction mixture was added $KMnO_4$ (10 mol) portion wise and reflux for 72 h. The hot reaction mixture was filtered through celite and washed with hot water. The filtrate was concentrated under vacuum, residue diluted with water (750 mL) and acidified with con. HCl at 0° C. The solid obtained was filtered, washed with water and dried under vacuum to give 4-nitro isophthalic acid (98 g, 56%).

TLC, Chloroform/Methanol, 7:3, $R_f$=0.2

Step II: 4-Amino isophthalic acid

To a solution of 4-nitro isophthalic acid (98 g, 0.457 mol) in methanol (5 L) was added Pd/C (20%) and hydrogenated at RT for 4 h. The reaction mixture was filtered through celite and filtrate concentrated under vacuum to give 4-amino isophthalic acid (72 g, 87%) as a solid.

TLC, Chloroform/Methanol, 7:3, $R_f$=0.4

Step III: 4-Oxo-3,4-dihydroquinazoline-6-carboxylic acid

A mixture of 4-amino isophthalic acid (17 g, 0.093 mol) and formamide (85 mL) was heated at 180° C. for 5 h. The reaction mixture was cooled to RT and added acetone. The solid precipitate thus obtained was stirred for 2 h, filtered and dried to give 4-oxo-3,4-dihydroquinazoline-6-carboxylic acid (11 g, 61%).

TLC, Chloroform/Methanol, 8:2, $R_f$=0.25

Step IV: 4-Oxo-3,4-dihydroquinazoline-6-methyl carboxylate

To a solution of 4-oxo-3,4-dihydroquinazoline-6-carboxylic acid (24 g, 0.126 mol) in dry methanol (800 mL) was added thionylchloride (37 g) at 5° C. and then refluxed at 80° C. for 5 h. The reaction mixture was concentrated under vacuum and crude taken in ethylacetate (250 mL). The organic layer was washed with 10% aqueous $NaHCO_3$, water, brine and dried. The solvent was removed under vacuum to give 4-oxo-3,4-dihydroquinazoline-6-methyl carboxylate (24 g, 92%) as a solid.

TLC, Chloroform/Methanol, 8:2, R=0.6

Step V: Methyl-4-chloroquinazoline-6-carboxylate

A mixture of 4-oxo-3,4-dihydroquinolin-6-methyl carboxylate (12 g, 0.058 mol) and phosphorylchloride (180 mL) was heated to reflux for 7 h. Excess phosphorylchloride was distilled off and crude taken in ethylacetate (250 mL). The organic layer was washed with 10% aqueous $NaHCO_3$ solution, water, brine and dried. The solvent was removed under vacuum and crude purified by column chromatography over silica gel (30% ethylacetate in pet. ether) to give methyl-4-chloroquinazoline-6-carboxylate (4.5 g, 34%) as a solid.

TLC, pet. ether/EtOAc, 1:1, $R_f$=0.65

LC-MS: M/Z ESI: 1.50 min, 223.19 (M+1). $^1$H NMR (DMSO-d6) δ 8.66 (d, J=1.9 Hz, 1H), 8.39 (s, 1H), 8.30 (dd, J=0.6 Hz, 8.5 Hz, 1H), 7.79 (d, J=8.5 Hz, 1H), 3.90 (s, 3H).

Intermediate 8: Preparation of 4-Methoxy-quinazoline-6-carboxylic acid methyl ester

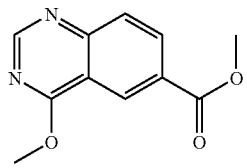

200 mg of methyl-4-chloroquinoline-6-carboxylate were stirred in 5 ml MeOH in the presence of 1 eq. of DIEA at 60° C. for 24 h. MeOH was evaporated and the crude residue was taken up in EtOAc and washed with $NH_4Cl$ affording a white solid sufficiently pure for the next step.

HPLC: 2.3 min. LC-MS: M/Z ESI: 1.19 min, 219.17 (M+1).

The following intermediate was synthesized according to the synthesis of intermediate 8:

Intermediate 9: Preparation of 4-Methylamino-quinazoline-6-carboxylic acid methyl ester

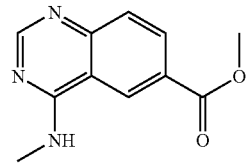

HPLC: 1.12 min. LC-MS: M/Z ESI: 1.06 min, 218.31 (M+1).

Intermediate 10: Preparation of 4-Methoxy-quinazoline-6-carbaldehyde

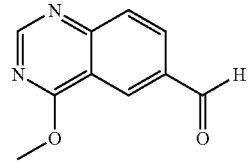

This intermediate was prepared according to the synthesis of intermediate 5 starting from 4-Methoxy-quinazoline-6-carboxylic acid methyl ester.

HPLC: 1.41 min. LC-MS: M/Z ESI: 1.24 min, 189.31 (M+1).

Intermediate 11: Preparation of 4-Methylamino-quinazoline-6-carbaldehyde

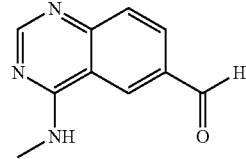

This intermediate was prepared according to the synthesis of intermediate 5 starting from 4-Methylamino-quinazoline-6-carboxylic acid methyl ester.

HPLC: 1.3 min. LC-MS: M/Z ESI: 0.90 min, 188.34 (M+1).

Intermediate 12: Preparation of 4-Chloro-quinazoline-6-carbaldehyde

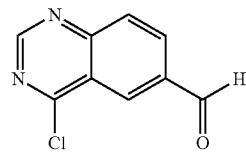

Step I: 4-Chloroquinazoline-6-yl methanol

To a solution of methyl-4-chloroquinazoline-6-carboxylate (3.5 g, 0015 mol) in dry THF (35 mL) at −25° C. was added DIBAL-H (4.4 g, 0.031 mol) and stirred at −25° C. to RT for 2 h. The reaction mixture was cooled to −10° C. and quenched with 10% aqueous NaHCO₃ (9 mL). The reaction mixture was extracted with ethylacetate (100 mL), washed with water, brine and dried. The solvent was removed under vacuum to give 4-chloroquinoline-6-yl methanol (2 g, 66%).

TLC, Chloroform/Methanol, 8:2, $R_f$=0.35

Step II: 4-Chloroquinazoline-6-carboxaldehyde

To a solution of 4-chloroquinazoline-6-yl-methanol (3.5 g, 0.018 mol) in dry CH₂Cl₂ (100 mL) was added Dess-Martin periodinane (8.4 g, 0.019 mol) and stirred at RT for 30 min. The reaction mixture was washed with 10% aqueous NaHCO₃ (75 mL), water, brine and dried. The solvent was removed under vacuum to give 4-chloroquinazoline-6-carboxaldehyde (3 g, 88%) as pale yellow solid.

TLC, Chloroform/Methanol, 9:1, $R_f$=0.6

Intermediate 13: Preparation of
4-Phenyl-quinazoline-6-carbaldehyde

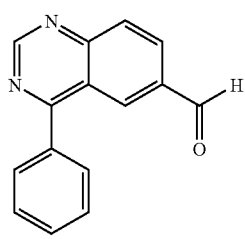

4-Chloro-quinazoline-6-carbaldehyde (50 mg, 0.26 mmol), Pd(PPh₃)₄ (13 mg, 0.01 mmol), phenylboronic acid (63 mg, 0.52 mmol) and sodium carbonate (sat. sol: 50 ul) were heated up in toluene at 100° C. for 12 h. After evaporation of the solvents, the residue was taken up in ethyl acetate and washed with brine twice. Organic phases were then concentrated and raw materiel was purified on silica gel using DCM/EtOH 95:5 as eluents to give 50 mgs (82%) of the desired cpd with a 85% purity.

HPLC: 2.68 min. LC-MS: M/Z ESI: 1.25 min, 235.30 (M+1).

Intermediate 14: Preparation of
4-Dimethylamino-quinazoline-6-carbaldehyde

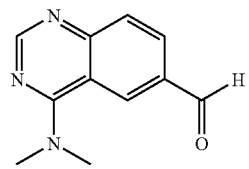

4-Chloro-quinazoline-6-carbaldehyde (200 mg, 1 mmol) was dissolved in 10 ml dioxane. To this solution was added a solution of dimethylamine in water (Seq.). The mixture was stirred during 2 h at r.t. Evaporation of the solvents and remaining amine under high vacuum afforded pure 4-Dimethylamino-quinazoline-6-carbaldehyde as a yellow solid, which was used for the next step without further purification (190 mg=91%).

HPLC: 0.91 min. LC-MS: M/Z ESI: 1.23 min, 202.33 (M+1). ¹H NMR (CDCl₃): δ 10.19 (s, 1H), 8.70 (s, 1H), 8.50 (d, J=3 Hz, 1H), 8.15 (dd, J=3 Hz, 9 Hz, 1H), 7.88 (d, J=9 Hz, 1H).

The following intermediates were synthesized in a similar way using the suitable amines as nucleophiles.

| N°. | Intermediate | M/Z ESI:(M + 1). |
|---|---|---|
| 15 | 4-Piperidin-1-yl-quinazoline-6-carbaldehyde | 242.27 |
| 16 | 4-Amino-quinazoline-6-carbaldehyde | 174.18 |
| 17 | 4-Benzylamino-quinazoline-6-carbaldehyde | 264.30 |
| 18 | 4-[(Pyridin-2-ylmethyl)-amino]-quinazoline-6-carbaldehyde | 265.33 |
| 19 | 4-[(Pyridin-3-ylmethyl)-amino]-quinazoline-6-carbaldehyde | 265.33 |
| 20 | 4-(4-Methyl-piperazin-1-yl)-quinazoline-6-carbaldehyde | 257.31 |
| 21 | 4-Diethylamino-quinazoline-6-carbaldehyde | 230.28 |
| 22 | 4-Morpholin-4-yl-quinazoline-6-carbaldehyde | 244.26 |
| 23 | 1-(6-Formyl-quinazolin-4-yl)-piperidine-3-carboxylic acid ethyl ester | 314.36 |
| 24 | 1-(6-Formyl-quinazolin-4-yl)-pyrrolidine-2-carboxylic acid tert-butylester | 328.39 |
| 25 | 1-(6-Formyl-quinazolin-4-yl)-piperidine-4-carboxylic acid ethyl ester | 314.36 |
| 26 | 4-(4-Hydroxy-piperidin-1-yl)-quinazoline-6-carbaldehyde | 258.30 |
| 27 | 4-(4-Methyl-piperidin-1-yl)-quinazoline-6-carbaldehyde | 256.32 |
| 28 | 4-(4-Phenethyl-piperidin-1-yl)-quinazoline-6-carbaldehyde | 346.42 |
| 29 | 4-(4-Benzyl-piperidin-1-yl)-quinazoline-6-carbaldehyde | 332.40 |
| 30 | 4-[4-(4-Fluoro-phenyl)-piperidin-1-yl]-quinazoline-6-carbaldehyde | 336.38 |
| 31 | 4-(4-Pyrimidin-2-yl-piperazin-1-yl)-quinazoline-6-carbaldehyde | 321.36 |

Intermediates 32: Preparation of
Methyl-benzotriazole-5-carboxylic acid methyl ester 1 g of Benzotriazole-5-carboxylic acid methyl ester (5.64 mmol) was dissolved in 20 ml DMF at 0° C. To this solution was added 1 eq. of NaH (60%) at 0° C. The mixture was stirred for 30 min at 0° C., 801 mg (1 eq.) of Methyliodide were slowly added, and the resulting reaction mixture was stirred for 2 h at rt. EtOAc was added and the organic layer was washed extensively with brine and water, dried over MgSO4 and filtered to afford 1 g of crude Methyl-benzotriazole-5-carboxylic acid methyl ester as three different regioisomers. The separation was performed on silica gel using EtOAc/CH 3:7 as eluents.

Intermediate 32a: 2-Methyl-2H-benzotriazole-5-carboxylic acid methyl ester

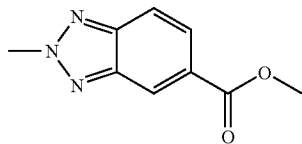

2-Methyl-2H-benzotriazole-5-carboxylic acid methyl ester eluted as first fraction (250 mg, 22%). HPLC: 2.32 min. $^1$H NMR (DMSO-d6) δ 8.56 (s, 1H), 8.02 (d, J=9 Hz, 1H), 7.93 (d, J=9 Hz, 1H), 4.55 (s, 3H), 3.90 (s, 1H).

Intermediate 32b: 3-Methyl-3H-benzotriazole-5-carboxylic acid methyl ester

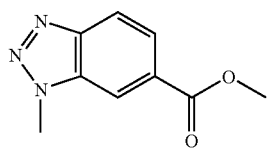

3-Methyl-3H-benzotriazole-5-carboxylic acid methyl ester eluted as $2^{nd}$ fraction (130 mg, 12%). HPLC: 2.03 min. $^1$H NMR (DMSO-d6) δ 8.56 (s, 1H), 8.13 (d, J=6 Hz, 1H), 7.93 (d, J=9 Hz, 1H), 4.39 (s, 3H), 3.92 (s, 3H).

Intermediate 32c: 1-Methyl-1H-benzotriazole-5-carboxylic acid methyl ester

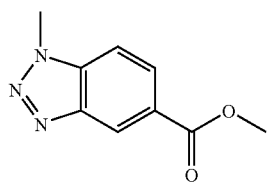

1-Methyl-1H-benzotriazole-5-carboxylic acid methyl ester eluted as $3^{rd}$ fraction (135 mg, 12%). HPLC: 2.03 min. $^1$H NMR (DMSO-d6) δ 8.62 (s, 1H), 8.11 (d, J=9 Hz, 1H), 7.97 (d, 9 Hz, 1H), 4.35 (s, 3H), 3.90 (s, 3H).

Intermediate 33: 2-Methyl-2H-benzotriazole-5-carbaldehyde

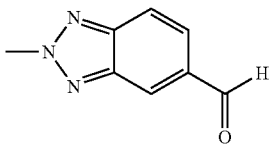

This intermediate has been synthesized according to the synthesis of intermediate 5 using 2-Methyl-2H-benzotriazole-5-carboxylic acid methyl (intermediate 32a) ester as starting point.

HPLC: 1.88 min. $^1$H NMR (DMSO-d6) δ 10.12 (s, 1H), 8.65 (s, 1H), 8.06 (d, J=9 Hz, 1H), 7.85 (d, J=9 Hz, 1H), 4.57 (s, 3H).

Intermediate 34: 3-Methyl-3H-benzotriazole-5-carbaldehyde

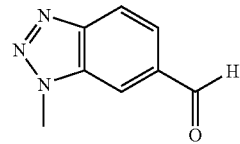

This intermediate has been synthesized according to the synthesis of intermediate 5 using 3-Methyl-3H-benzotriazole-5-carboxylic acid methyl ester (intermediate 32b) as starting point.

HPLC: 1.49 min. $^1$H NMR (DMSO-d6) δ 10.18 (s, 1H), 8.54 (s, 1H), 8.20 (d, J=9 Hz, 1H), 7.88 (d, J=9 Hz, 1H), 4.41 (s, 3H).

Intermediate 35: 1-Methyl-1H-benzotriazole-5-carbaldehyde

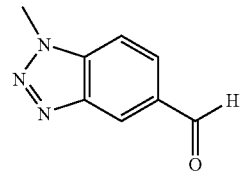

This intermediate has been synthesized according to the synthesis of intermediate 5 using 1-Methyl-1H-benzotriazole-5-carboxylic acid methyl ester as starting point (intermediate 32c).

HPLC: 1.49 min. LC-MS: M/Z ESI: 1.07 min, 162.32 (M+1). $^1$H NMR (DMSO-d6) δ 10.13 (s, 1H), 8.70 (s, 1H), 8.05 (s, 2H), 4.36 (s, 3H).

Intermediate 36: 5-(4-Amino-3-ethylamino-benzylidene)-thiazolidine-2,4-dione

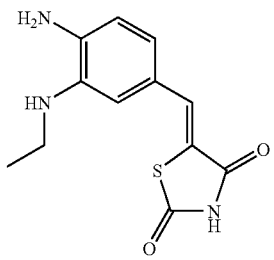

Step 1: 3-Fluoro 4-nitro benzyl alcohol (*Bioorg. Med. Chem.* 7, 1999, 2647)

To an ice-cooled suspension of NaBH$_4$ (204 mg, 5.4 mmol, 2 eq.) in THF (10 mL) was added dropwise 3-fluoro 4-nitro benzoic acid (500 mg, 2.7 mmol, 1 eq.) in THF (10 mL) over 30 minutes. BF$_3$-Et$_2$O (7.3 mmol, 2.7 eq.) was then added dropwise over 30 minutes. The solution was stirred at room temperature over night. 1N HCl was added dropwise to quench NaBH$_4$ excess. The solvent was removed in vacuo, the residue dissolved in DCM, washed with water, brine. The organic layer was then dried over MgSO$_4$ and the solvent removed in vacuo to give 425 mg of 3-fluoro 4-nitro benzyl alcohol (92% yield). The compound was used in the following step with no further purification.

$^1$H NMR: δ=(400 MHz, CDCl$_3$): 7.97 (m, 1H), 7.28 (m, 1H), 7.18 (m, 1H), 4.75 (m, 2H).

Step II: 3-Fluoro 4-nitro benzyl aldehyde 3-fluoro 4-nitro benzyl alcohol (116 mg, 0.68 mmol, 1 eq.) was dissolved in DCM (10 ml) and treated with MnO$_2$ (580 mg, 6.73 mmol, 10 eq.) and the suspension stirred at room temperature over night. MnO$_2$ was filtered off the suspension using celite and the solvent evaporated to give the corresponding aldehyde as a white solid (66% yield).

$^1$H NMR: δ=(400 MHz, CDCl$_3$): 9.98 (s, 1H, CHO), 8.08 (m, 1H, ArH), 7.78 (m, 2H, ArH).

Step III: 5-(3-Fluoro-4-nitro-benzylidene)-thiazolidine-2,4-dione (*J. Med. Chem.* 37, 2, 1994, 322)

A mixture of 3-fluoro 4-nitro benzyl aldehyde (280 mg, 1.65 mmol, 1 eq.), thiazolidine-dione (193 mg, 1.65 mmol, 1 eq.) and β-alanine (95 mg, 1.1 mmol, 0.65 eq.) in acetic acid (5 mL) was stirred over night at 100° C. The cooled reaction mixture was added to water and stirred for 1 hour. The precipitated product was filtered and washed with water and dried to yield the final product as a yellow/orange solid (77% yield).

$^1$H NMR: δ=(400 MHz, (CD$_3$)$_2$CO): 8.0 (m, 1H, ArH), 7.68 (m, 2H, ArH), 7.53 (s, 1H, CH=C).

Step IV: 5-(3-Ethylamino-4-nitro-benzylidene)-thiazolidine-2,4-dione 5-(3-Fluoro-4-nitro-benzylidene)-thiazolidine-2,4-dione (200 mg, 0.75 mmol, 1 eq.), was dissolved in DME (6 mL) and TEA (208 μL, 1.5 mmol, 2 eq.) and a solution of ethylamine (2 eq.) was added. The reaction mixture was shaken at 60° C. over night. The solvent was removed in vacuo and residue dissolved in ethyl acetate and washed with 10% ammonium chloride aqueous solution. The organic layer was dried on Na$_2$SO$_4$ and the solvent evaporated to give the corresponding aniline derivative as either red oil, which was used for the next step without further purification.

Step V: 5-(3-Ethylamino-4-amino-benzylidene)-thiazolidine-2,4-dione

To a stirred solution of 5-(3-Ethylamino-4-nitro-benzylidene)-thiazolidine-2,4-dione in THF, a solution of sodium hydrosulfite (3 eq.) in water was slowly added followed by an aqueous solution of K$_2$CO$_3$. The reaction mixture was refluxed over night. THF was removed in vacuo and residue extracted with ethyl acetate The organic layer was dried on Na$_2$SO$_4$ and the solvent evaporated to give the corresponding aniline derivative, which was used without any further purification.

The following intermediates were synthesized in a similar way using the suitable amines as nucleophiles as described in step IV of intermediate 36. The so-obtained 3-alkylamino-4-nitro-benzylidene)-thiazolidine-2,4-diones were reduced as described in step V of intermediate 36 affording 3-alkylamino-4-amino-benzylidene)-thiazolidine-2,4-diones.

| N°. | Intermediate | M/Z ESI:(M + 1) |
|---|---|---|
| 37 | 5-[4-Amino-3-(4-phenyl-butylamino)-benzylidene]-thiazolidine-2,4-dione | 368.2 |
| 38 | 5-{4-Amino-3-[2-(4-trifluoromethyl-phenyl)-ethylamino]-benzylidene}-thiazolidine-2,4-dione | 408.12 |
| 39 | 5-{4-Amino-3-[2-(4-hydroxy-phenyl)-ethylamino]-benzylidene}-thiazolidine-2,4-dione | 356.13 |
| 40 | 4-[2-Amino-5-(2,4-dioxo-thiazolidin-5-ylidenemethyl)-phenylamino]-cyclohexanecarboxylic acid methyl ester | 376.35 |
| 41 | 5-{4-Amino-3-[2-(1H-indol-3-yl)-ethylamino]-benzylidene}-thiazolidine-2,4-dione | 409.21 |
| 42 | 5-{4-Amino-3-[(1-methyl-1H-pyrazol-4-ylmethyl)-amino]-benzylidene}-thiazolidine-2,4-dione | 331.1 |
| 43 | 5-{4-Amino-3-[2-(3,4-dimethoxy-phenyl)-ethylamino]-benzylidene}-thiazolidine-2,4-dione | 400.21 |
| 44 | 5-[4-Amino-3-(4-trifluoromethyl-benzylamino)-benzylidene]-thiazolidine-2,4-dione | 394.15 |
| 45 | 4-[2-Amino-5-(2,4-dioxo-thiazolidin-5-ylidenemethyl)-phenylamino]-cyclohexanecarboxylic acid | 362.17 |
| 46 | 5-(4-Amino-3-isobutylamino-benzylidene)-thiazolidine-2,4-dione | 292.22 |
| 47 | 5-[4-Amino-3-(2-benzo[1,3]dioxol-4-yl-ethylamino)-benzylidene]-thiazolidine-2,4-dione | 384.26 |
| 48 | 5-{4-Amino-3-[2-(2-phenoxy-phenyl)-ethylamino]-benzylidene}-thiazolidine-2,4-dione | 432.28 |
| 49 | 5-[4-Amino-3-(3,3-diphenyl-propylamino)-benzylidene]-thiazolidine-2,4-dione | 430.27 |
| 50 | 5-(4-Amino-3-prop-2-ynylamino-benzylidene)-thiazolidine-2,4-dione | 274.21 |
| 51 | 5-[4-Amino-3-(2-methoxy-benzylamino)-benzylidene]-thiazolidine-2,4-dione | 356.23 |
| 52 | 5-{4-Amino-3-[(furan-3-ylmethyl)-amino]-benzylidene}-thiazolidine-2,4-dione | 316.21 |
| 53 | 5-(4-Amino-3-propylamino-benzylidene)-thiazolidine-2,4-dione | 278.16 |
| 54 | 5-{4-Amino-3-[2-(4-phenoxy-phenyl)-ethylamino]-benzylidene}-thiazolidine-2,4-dione | 432.23 |

Intermediate 55: Quinoxaline-6-carbaldehyde

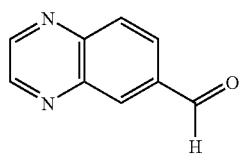

Step I: Quinoxaline-6-carbonyl chloride

In a 1 l 3 neck flask was placed Quinoxaline-6-carboxylic acid (20.2 g) in 500 ml of THF. To this solution was slowly added thionylchloride (42 ml, Seq.). The reaction mechanically stirred was warmed up to reflux and followed by HPLC quenching the sample with NH$_4$OH. After 3 h at reflux no more starting material was present, the solvent was removed under reduced pressure and SOCl$_2$ was chased with toluene 3 times. The solid was suspended in 100 ml EtOAc and filtered to obtain 23.47 g of a beige solid.

HPLC: 1.114 min. $^1$H NMR (DMSO-d6) δ 9.01-7.40 (m, 5H).

Step I: Quinoxaline-6-carbaldehyde

In a 1 l 3-neck flask under argon was placed Quinoxaline-6-carbonyl chloride in 600 ml of DME. To this solution was added lithium tri-tert-butoxyaluminohydride (1 eq.) at −78° C. over 1.5 h. The reaction was kept at that temperature for 5 h. Then ice was added, and the reaction was diluted with AcOEt and filtrated over celite. The two layers were separated and the organic phase was washed with NaHCO$_3$ sat. Quinoxaline-6-carbaldehyde was obtained upon evaporating the solvent in 73% yield as yellowish solid.

HPLC: 1.49 min. LC-MS: M/Z ESI: 0.81 min, 159.37 (M+1). $^1$H NMR (CDCl3) δ 10.28 (s, 1H), 8.97 (s, 2H), 8.61 (s, 1H), 8.27 (q, 6 Hz, 9 Hz, 2H).

Intermediate 56: Benzothiazole-6-carbaldehyde

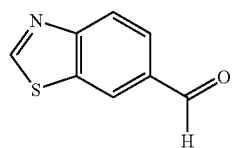

This intermediate was synthesized as seen in the synthesis of intermediate 55 starting from Benzothiazole-6-carboxylic acid. The overall yield was 38%.

HPLC: 1.92 min. LC-MS: M/Z ESI: 0.97 min, 164.27 (M+1). $^1$H NMR (DMSO-d6) δ 10.1 (s, 1H), 9.60 (s, 1H), 8.60 (s, 1H), 8.20 (m, 1H), 8.10 (d, 1H).

Intermediate 57: 3-Methyl-benzofuran-5-carbaldehyde

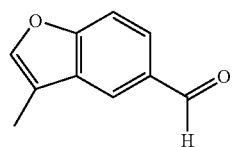

This intermediate was accessed through the same route as intermediate 1 using Ethyl-2-acetyl-4-bromophenoxy acetate as starting material. Overall yield 50%.

LC-MS: M/Z ESI: 1.55 min, 161.34 (M+1). $^1$H NMR (DMSO-d6) δ 10.1 (s, 1H), 8.21 (d, J=1.5 Hz 1H), 7.92 (d, J=1.3 Hz, 1H), 7.88-7.84 (dd, J=1.6 Hz, 1H), 7.73-7.71 (d, J=8.5 Hz, 1H), 2.25 (s, 3H).

Intermediate 58: 3-Bromo-benzofuran-5-carbaldehyde

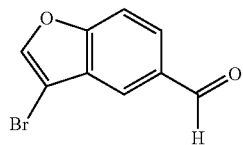

Step I: 2,3-Dibromo-2,3-dihydro-benzofuran-5-carbaldehyde

Intermediate 1 (2 g, 13.7 mmol) was dissolved in 10 ml CHCl3 and cooled to −10° C. To this was added a solution of Br$_2$ in CHCl$_3$ (1.55 eq., c=4.162 mol/l). The reaction mixture turned dark and was allowed to reach r.t. during 1 h. HPLC indicated complete addition of bromine. The solvent and remaining bromine were evaporated under reduced pressure affording a reddish oil (4.1 g=90%), which was used for the next step without further purification.

HPLC: 3.43 min

Step II: 3-Bromo-1-benzofuran-5-carbaldehyde

To a solution of 2,3-dibromo-2,3-dihydro-1-benzofuran-5-carbaldehyde (4.1 g) in dry ethanol (15 mL) was added a solution of KOH (2.2 eq.) in dry ethanol (14 mL) and refluxed at 70° C. for 1 h. The reaction mixture was cooled, diluted with water and extracted with EtOAc (3×50 mL). The organic layer was washed with water, brine and dried. The solvent was removed under vacuum and the residue was purified by flash chromatography (pet. ether/EtOAc 99.5:0.5) to give the title compound as a pale yellow solid (2.91 g (80% pure), yield=78%).

HPLC: 3.35 min. $^1$H NMR (DMSO-d$_6$, 300 MHz) δ 10.12 (s, 1H), 8.47 (s, 1H), 8.14 (d, J=1.5 Hz, 1H), 7.97 (dd, J=8.6, 1.5 Hz, 1H), 7.87 (d, J=8.6 Hz, 1H).

Intermediate 59: 3-Phenylethynyl-benzofuran-5-carbaldehyde

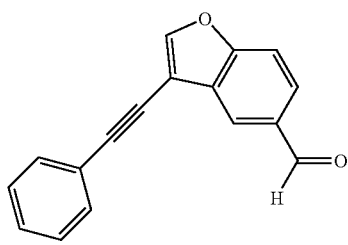

In a dry flask 3-Bromo-1-benzofuran-5-carbaldehyde (1 g, 4.4 mmol) were dissolved in anhydrous THF (50 ml). To this was added under Argon Bis (triphenylphosphine) palladium (II) chloride (160 mg, 0.2 mmol), TEA (2.81 mL, 5 eq.), CuI (40 mg, 0.2 mmol) and Phenylacetylene (897 mg, 8.8 mmol). The reaction was heated at 55° C. for 2 days. The crude was filtered through celite and purified on silicagel using as eluent cyclohexan-ethyl acetate (7-3) affording 680 mg (yield: 56%)

HPLC: 4.71 min. $^1$H NMR (DMSO-d6) δ 10.14 (s, 1H), 8.64 (s, 1H), 8.38 (s, 1H), 7.97 (dd, J=1.5 Hz, 8.3 Hz, 1H), 7.90 (d, J=8.6 Hz, 1H), 7.65 (m, 2H), 7.46 (m, 3H).

Intermediate 60:
3-(5-Formyl-benzofuran-3-yl)-acrylic acid ethyl ester

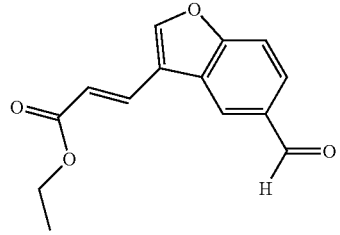

In a sealed tube 3-Bromo-1-benzofuran-5-carbaldehyde (500 mg, 2.22 mmol) was dissolved in 7 ml of ACN. To this solution was added PPh$_3$ (1.16 g, 4.44 mmol), Pd(II)acetate (500 mg, 2.2 mmol), Et3N (073 mL, 5.55 mmol) and finally acrylic acid ethyl ester (2.41 ml, 22 mmol). The tube was sealed and the reaction was heated at 120° C. for one hour. The crude was filtered on celite to eliminate inorganic contaminations. The solvents were evaporated and the crude was purified by silicagel chromatography using cyclohexane-AcOEt 95-5 to 50-50. A pale yellow solid was obtained (400 mg, yield:42%).

HPLC: 3.69 min. $^1$H NMR (DMSO-d6) δ 10.15 (s, 1H), 8.70 (s, 2H), 7.97 (d, J=9 Hz 1H), 7.88 (s, 1H), 7.82 (s, 1H), 6.76 (d, J=15 Hz, 1H), 4.23 (q, J=6 Hz, 12 Hz, 2H), 1.28 (t, J=9 Hz, 3H).

Intermediate 61:
2,3-Dihydro-benzo[1,4]oxazine-4,6-dicarboxylic acid 4-tert-butyl ester 6-methyl ester

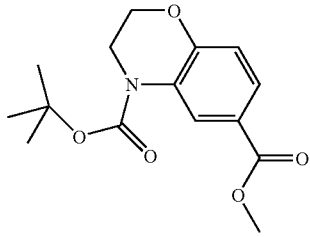

Step I: 3-Amino-4-hydroxy-benzoic acid methyl ester

To a 2000 ml three-necked flask containing 3-Nitro-4-hydroxy-benzoic acid methyl ester (43 g, 2188 mmol) in MeOH (860 ml; 20 vols) was added palladium on carbon in water (2 g in 10 ml of water). Ammonium formiate (68.76 g, 5 eq.) was added in a single portion under stirring. After 2 to 3 minutes a suspension was observed, and temperature raised from 20° C. to 30° C. Ice bath was used to cool reaction mixture to 20° C. and the reaction was stirred at 20° C. for 40 minutes until completion (no more yellow color). Reaction mixture was filtered on silica plug, rinsed with MeOH, and the filtrate was concentrated under vacuum to give a green oil which was taken up in ethyl acetate (400 ml). The organic phase was washed twice with water, dried over MgSO$_4$, filtered and concentrated to give a cream solid m=31.35 g (86%).

LC-MS: M/Z ESI: 0.81 min, 168.37 (M+1)

Step II:
3,4-Dihydro-2H-benzo[1,4]oxazine-6-carboxylic acid methyl ester*hydrochloride To a 2000 ml three-necked flask under N$_2$ containing 3-Amino-4-hydroxy-benzoic acid methyl ester (31.35 g, 187 mmol) in anhydrous DMF (630 ml; 20 vols) at RT, was added K$_2$CO$_3$ (103 g, 4 eq.) in one portion followed by 1,2dibromo-ethane (65 ml, 4 eq.) in one portion. The reaction mixture was stirred at 70° C. for 12 h. Temperature was allowed to cool down to RT, and HCl1N was added until pH=8, and extraction was performed using diethyl ether (3*200 ml). The organic phase was washed with water (2*200 ml) and dried over MgSO$_4$ and concentrated to afford a brown red oil with solid, which was taken up again in diethyl ether (450 ml) and THF (50 ml) and filtered to remove a white solid. To the filtrate was added HCl1N, and diethyl ether (130 ml) was added, suspension was stirred at RT for 5 minutes and filtered to give 27.6 g of crude product. The aqueous phases were again extracted with ethyl acetate to afford additional 6.23 g of product. The combined fractions (32 g) were recrystallised from EtOH (420 ml; 13 vols) to give after filtration and drying a white powder (19.47 g (16.37 g free base)), yield=40%.

HPLC: 1.954 min. LC-MS: M/Z ESI: 1.27 min, 194.45 (M+1).

Step III:
2,3-Dihydro-benzo[1,4]oxazine-4,6-dicarboxylic acid 4-tert-butyl ester 6-methyl ester To a 500 ml three-necked flask containing 3,4-Dihydro-2H-benzo[1,4]oxazine-6-carboxylic acid methyl ester*hydrochloride in suspension in THF (145 ml; 10 vols) under N$_2$, DIEA (27 ml, 2.5 eq.) was added in one portion at RT and partial solubilisation was observed. Boc anhydride/ (16.4 g, 1.2 eq.) was added in one portion and the reaction was stirred at 65° C. for 5 days. During that time several small portions of 0.2 eq. of Boc$_2$O and DIEA were added. THF was removed under vacuum and the residue was taken up in DCM 150 ml The organic phase was washed with a saturated solution of NaHCO$_3$ and then with brine. After drying over MgSO$_4$ and filtration, volatiles were removed under vacuum and the residue was recrystallised from EtOH (80 ml) to give cream crystals (14.8 g, 76%).

HPLC: 4.038 min. $^1$H NMR (CDCl3) δ8.49 (s, 1H), 7.68 (dd, J=3 Hz, 9 Hz, 1H), 6.89 (d, J=9 Hz, 1H), 4.30 (q, J=3 Hz, 9 Hz, 2H), 3.89 (m, 5H), 1.62 (s, 9H).

Intermediate 62: 6-Formyl-2,3-dihydro-benzo[1,4]oxazine-4-carboxylic acid tert-butyl ester

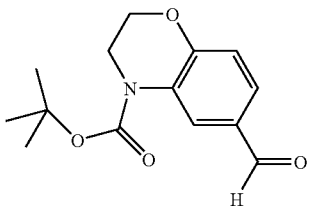

This intermediate was accessed through oxido-reduction as described for intermediate 5.

HPLC: 3.727 min. LC-MS: M/Z ESI: 1.81 min, 264.34 (M+1). ¹H NMR (DMSO-d6) δ 9.83 (s, 1H), 8.35 (s, 1H), 7.53 (d, J=6 Hz, 1H), 7.05 (d, J=9 Hz, 1H), 4.31 (t, J=3 Hz, 2H), 3.83 (t, J=6 Hz, 2H), 1.50 (s, 9H).

Intermediate 63: 6-Formyl-benzo[1,4]oxazine-4-carboxylic acid tert-butyl ester

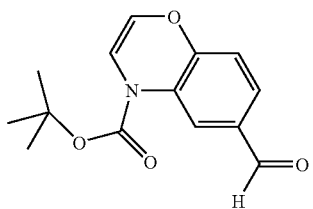

Step I: 2,3-Dibromo-2,3-dihydro-benzo[1,4]oxazine-4,6-dicarboxylic acid 4-tert-butyl ester 6-methyl ester To a solution of 2,3-Dihydro-benzo[1,4]oxazine-4,6-dicarboxylic acid 4-tert-butyl ester 6-methyl ester (500 mg, 1.7 mmol) in dry carbon tetrachloride (20 ml) was added N-Bromosuccinimide (667 mg, 3.75 mmol) and a catalytic amount of benzoylperoxide. The resulting mixture was stirred and heated with a bulp lamp (100 W) at reflux for 45 min. The mixture was allowed to cool and the succinimide was filtered off. The filtrate was evaporated to yield an oil (767 mg, 99%) sufficiently pure to be used for the next step.

HPLC: 3.978 min

Step II: Benzo[1,4]oxazine-4,6-dicarboxylicacid 4-tert-butyl ester 6-methyl ester 2,3-Dibromo-2,3-dihydro-benzo[1,4]oxazine-4,6-dicarboxylic acid 4-tert-butyl ester 6-methyl ester (767 mg, 1.7 mmol) from proceeding step was stirred in acetone (14 ml) at RT for 2 h with NaI (1.27 g, 8.5 mmol). The solvent was removed, EtOAc, water and 1 M sodium thiosulfate were added. After separating phases the organic layer was washed with brine. The solvent was concentrated and the crude was purified on silica gel using CH/EtOAc 7:3 to obtain a colorless oil (456 mg, 92%).

HPLC: 4.386 min.

Step III: 6-Hydroxymethyl-benzo[1,4]oxazine-4-carboxylic acid tert-butyl ester

Step IV: 6-Formyl-benzo[1,4]oxazine-4-carboxylic acid tert-butyl ester

Step III and IV were carried out according to the synthesis of intermediate 5.

HPLC: 3.388 min.

Intermediate 64: (6-Formyl-3-oxo-2,3-dihydro-benzo[14]oxazin-4-yl)-acetic acid methyl ester

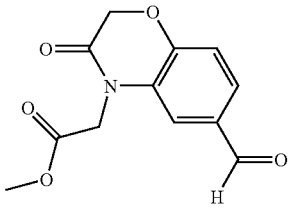

Step I: Methyl-3-amino-4-hydroxybenzoate

To a solution of 3-amino-4-hydroxybenzoic acid (10 g, 0.65 mol) in methanol (1.5 L) was added thionylchloride (233 g, 1.96 mol) drop-wise at 5-10° C. with stirring and allowed to reflux at 65° C. for 16 h. Excess methanol and thionylchloride was distilled off and crude dissolved in ethylacetate (500 mL). The organic layer was washed with 5% aqueous NaHCO₃ solution, water, brine and dried. The solvent was removed under vacuum to give methyl-3-amino-4-hydroxybenzoate (105 g, 95%).

Step II: Methyl-3-oxo-3,4-dihydro-2H-1,4-benzoxazin-6-carboxylate

To a mixture of methyl-3-amino-4-hydroxybenzoate (105 g, 0.62 mol) and benzyltriethylammonium chloride (142 g, 0.62 mol) in dry CHCl₃ (1.5 L) was added NaHCO₃ (211 g, 2.5 mol) with stirring. The reaction mixture was cooled to -5° C., added chloroacetylchloride (85 g, 0.75 mol) in dry CHCl₃ (350 mL) over a period of 1.5 h at the same temperature. The reaction mixture was then heated to 55° C. for 16 h. The solvent was removed under vacuum, added water (3 L) and filtered off the solid. The solid product was dried and recrystallised from ethanol to give methyl-3-oxo-3,4-dihydro-2H-1,4-benzoxazin-6-carboxylate (108 g, 83%).

Step III: 6-(Hydroxymethyl)-2H-1,4-benzoxazin-3(4H)-one

A solution of methyl-3-oxo-3,4-dihydro-2H-1,4-benzoxazin-6-carboxylate (30 g, 0.145 mol) in dry CH₂Cl₂ (500 mL) was cooled to -78° C. and added DIBAL-H (51 g, 0.36 mol) over a period of 45 min and then stirred at the same temperature for 14 h. The reaction mixture was quenched with 1.5N HCl and filtered off the solid product. The solid compound was dried under vacuum to give 6-(hydroxymethyl)-2H-1,4-benzoxazin-3(4H)-one (18 g, 69%).

Step IV: TBDMS-6-(hydroxymethyl)-2H-1,4-benzoxazin-3(4H)-one

To a solution of 6-(hydroxymethyl)-2H-1,4-benzoxazin-3 (4H)-one (18 g, 0.1 mol) in dry DMF (250 mL) was added imidazole (13.7 g, 0.2 mol) and stirred at 0° C. for 30 min. To the above reaction mixture was added TBDMSiCl (23 g, 0.15 mol) in portions and stirred at RT for 4 h. The reaction mixture was diluted with water and filtered off the solid obtained. The solid was dried under vacuum to give TBDMS-6-(hydroxymethyl)2H-1,4-benzoxazin-3(4H)-one (24.5 g, 83%).

Step V: Methyl-[6-(hydroxymethyl)-3-oxo-2,3-dihydro-4H-1,4-benzoxazin-4-yl]acetate To a suspension of NaH (0.3 g, 0.01 mol) in dry DMF (15 mL) was added TBDMS-6-(hydroxymethyl)$_2$H-1,4-benzoxazin-3(4H)-one (2 g, 0.0068 mol) at 0° C. with stirring and allowed to stir at RT for 2 h. The reaction mixture was cooled to 0° C., added methylchloroacetate (1 g, 0.0088 mol) and stirred at RT for 12 h. The reaction mixture was further cooled to 0° C., added 50 mL of 1.5N HCl solution and stirred at RT for 12 h. The reaction mixture was diluted with water (200 mL), extracted with ethylacetate (3×150 mL). The combined organic layer was washed with 10% aqueous NaHCO$_3$ solution, brine and dried. The solvent was removed under vacuum and crude purified by column chromatography over silica gel (CHCl$_3$/Methanol, 99.5:0.5) to give methyl-[6-(hydroxymethyl)-3-oxo-2,3-dihydro-4H-1,4-benzoxazin-4-yl]acetate (1.2 g, 70%).

Step VI: Methyl-[6-(Formyl)-3-oxo-2,3-dihydro-4H-1,4-benzoxazin-4-yl]acetate A mixture of PCC (4.2 g, 0.019 mol) and celite (4 g) in dry CH$_2$Cl$_2$ (100 mL) was cooled to 0° C. and slowly added a solution of methyl-[6-(hydroxymethyl)-3-oxo-2,3-dihydro-4H-1,4-benzoxazin-4-yl]acetate (1.2 g, 0.0048 mol) in CH$_2$Cl$_2$ (30 mL) under N$_2$. The reaction mixture was stirred at RT for 2 h, passed through celite, washed with CH$_2$Cl$_2$ (50 mL) and concentrated to give crude product, which was purified on silica gel affording 1.05 g (87%).

LC-MS: M/Z ESI: 1.15 min, 250.41 (M+1). $^1$H NMR (DMSO-d6) δ 9.88 (s, 1H), 7.65-7.60 (m, 2H), 7.24 (d, J=8.1 Hz, 1H), 4.85 (d, J=9.9 Hz, 4H), 3.71 (s, 3H).

Intermediate 65: 4-Butyl-3-oxo-3,4-dihydro-2H-benzo[1,4]oxazine-6-carbaldehyde

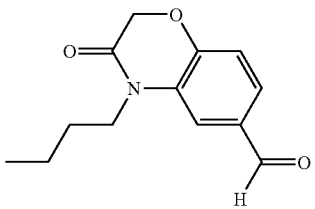

This intermediate was synthesized according to the synthesis of intermediate 2. Overall yield 33%.

LC-MS: M/Z ESI: 1.60 min, 234.35 (M+1). $^1$H NMR (DMSO-d6) δ 7.66 (d, J=0.7 Hz, 1H), 7.58 (dd, J=1.7 Hz, 8.1 Hz, 1H), 7.18 (d, J=8.2 Hz, 1H), 4.77 (s, 2H), 3.96 (t, J=7.3 Hz, 1H), 1.61-1.51 (m, 3H), 1.97-1.27 (m, 3H), 0.91 (t, J=7.3 Hz, 3H).

Intermediate 66: 4-Benzyl-3-oxo-3,4-dihydro-2H-benzo[1,4]oxazine-6-carbaldehyde

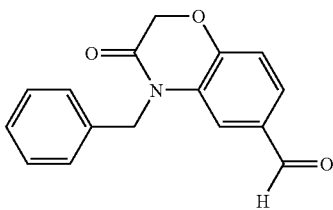

This intermediate was synthesized according to the synthesis of intermediate 2. Overall yield 29%.

$^1$H NMR (DMSO-d6) δ 9.78 (s, 1H), 7.58 (dd, J=1.5 Hz, 7.9 Hz, 1H), 7.47 (d, J=1.9 Hz, 7.40-7.18 (m, 6H), 5.22 (s, 2H), 4.95 (s, 2H), 3.3 (d, J=7.2 Hz, 1H).

Intermediate 67: 2-Chloro-5-[1,3]dioxolan-2-yl-benzofuran

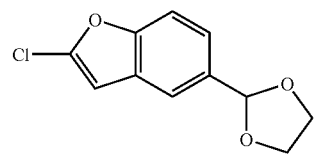

Step I: 5-[1,3]Dioxolan-2-yl-benzofuran

A mixture of benzofuran-5-carbaldehyde (150 mg, 1.03 mmol), ethylene glycol (230 ul, 4 eq), trimethyl orthoformate (123 ul, 1.1 eq) and tetrabutylammonium tribromide (49 mg, 0.1 eq) was stirred at room temperature for one night. Some starting material could be detected by TLC. However, the reaction mixture was poured into saturated NaHCO$_3$ solution and the product was extracted with ethyl acetate. Combined organic layers were dried over anhydrous sodium sulfate, filtrated and concentrated to give a crude product, which was purified by flash chromatography using cyclohexane/ethyl acetate 20:0.75 as solvents. The title compounds was obtained in 36% yield (70 mg).

LC-MS: M/Z ESI: 1.51 min, 191.30 (M+1).

Step II: 2-Chloro-5-[1,3]dioxolan-2-yl-benzofuran

5-[1,3]Dioxolan-2-yl-benzofuran (50 mg, 0.26 mmol) was dissolved in TIE (2 mL) and the solution was cooled down to −78° C. Butyl lithium (180 uL, 1.1 eq.) was added dropwise. This mixture was stirred 30 min at 25° C. Then the reaction mixture was cooled down to −78° C. and NCS (39 mg, 1.1 eq.) dissolved in 1 mL THF was added dropwise to the reaction mixture. After 1 h30 at −78° C. only small amount of starting material could be detected. The temperature was increased slowly to room temperature overnight. Water and ethyl acetate were added to the mixture and the aqueous layer was extracted 3 times. Combined organic phases was dried over MgSO$_4$, filtrated and evaporated to give 2-Chloro-5-[1,3] dioxolan-2-yl-benzofuran (48.1 mg, 81%) sufficiently pure to be used in the next step.

LC-MS: M/Z ESI: 1.77 min, 225.23 (M+1).

Intermediate 68: 3-Amino-benzo[d]isoxazole-5-carbaldehyde

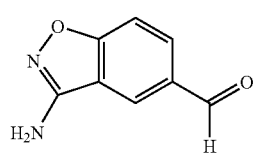

Kaiser oxime resin (Novabiochem 01-64-0188) (250 mg) was washed with DCM and THF (3 times 5 min), 2 ml of THF was added followed by the addition of 300 ul of potassium-tert.butoxide (1M in THF, 1.2 eq.) at r.t. The resin turned orange and was shaken in the Quest210™ for 15'. 2-Fluoro-5-formyl-benzonitrile (75 mg, 2 eq.) in 1 ml THF was added and the reaction was heated at 55° C. for 12 h. The resin was washed with DCM, MeOH, water (each 2×5 minutes) and MeOH (4×5 min). The resin was dried at 40° C. with a flow of Argon for 30' before cleaving.

The so dried resin was treated with TFA/5N HCl 4:1 (2.5 ml) for 2 h at 55° C. The solution was collected in 20 ml vials and the resin was washed twice with 4 ml of DCM. The collected fractions were evaporated with the Genevac HT4 to dryness affording: 37 mg (92%) of pure 3-Amino-benzo[d]isoxazole-5-carbaldehyde.

HPLC: 1.47 min. LC-MS: M/Z ESI: 0.82 min, 163.26 (M+1).

Intermediate 69:
4-Piperidin-1-yl-quinazoline-6-carboxylic acid methyl ester

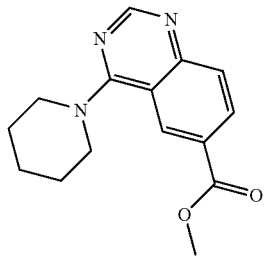

This intermediate was prepared according to the synthesis of intermediate 8 starting from 4-Chloro-quinazoline-6-carboxylic acid methyl ester (intermediate 7).

HPLC: 1.81 min. LC-MS: M/Z ESI: 1.78 min, 272.32 (M+1).

Intermediate 70:
4-Piperidin-1-yl-quinazoline-6-carbaldehyde

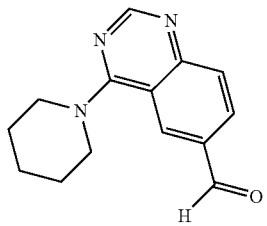

This intermediate was prepared according to the synthesis of intermediate 5 starting from 4-Piperidine-quinazoline-6-carboxylic acid methyl ester (intermediate 71).

HPLC: 1.36 min. LC-MS: M/Z ESI: 1.40 min, 242.32 (M+1).

Intermediate 71:
3-(5-Formyl-benzofuran-3-yl)-propionic acid ethyl ester

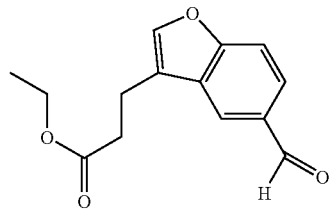

100 mg of 3-(5-Formyl-benzofuran-3-yl)-acrylic acid ethyl ester (intermediate 62) were dissolved in EtOAc in the presence of Palladium on charcoal and Argon. To this was connected a $H_2$-balloon and hydrogenation was carried out for 12 h. The palladium was filtered off and the solvents were evaporated affording pure title compound (80 mg, 80%).

HPLC: 3.53 min. LC-MS: M/Z ESI: 1.68 min, 247.25 (M+1).

Intermediate 72:
2-Methyl-5-[1,3]dioxolan-2-yl-benzofuran

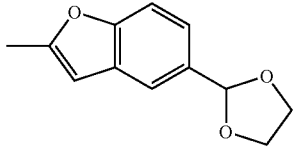

5-[1,3]Dioxolan-2-yl-benzofuran (50 mg, 0.26 mmol) was dissolved in THF (2 mL) and the solution was cooled down to −78° C. Butyl lithium (180 uL, 1.1 eq.) was added dropwise. This mixture was stirred 30 min at 25° C. Then the reaction mixture was cooled down to −78° C. and iodomethane (18.1 uL, 1.1 eq.) dissolved in 1 mL THF was added dropwise to the reaction mixture. The temperature was increased slowly to room temperature overnight. Despite some starting material was detected, water and ethyl acetate were added to the mixture and the aqueous layer was extracted 3 times. Combined organic phases was dried over $MgSO_4$, filtrated and evaporated to give 2-methyl-5-[1,3]dioxolan-2-yl-benzofuran (41.2 mg, 70%) sufficiently pure to be used in the next step.

LC-MS: M/Z ESI: 1.71 min, 205.34 (M+1).

Intermediate 73:
5-[1,3]Dioxolan-2-yl-benzofuran-2-carboxylic acid methyl ester

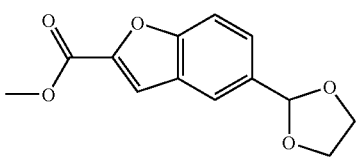

5-[1,3]Dioxolan-2-yl-benzofuran (50 mg, 0.26 mmol) was dissolved in THF (2 mL) and the solution was cooled down to −78° C. Butyl lithium (180 uL, 1.1 eq.) was added dropwise. This mixture was stirred 30 min at 25° C. Then the reaction mixture was cooled down to −78° C. and methyl cyanoformate (23 uL, 1.1 eq.) dissolved in 1 mL THF was added dropwise to the reaction mixture. After 1 h30 only small amount of starting material was detected and two major compounds were formed (expected product/dimer 73:27). The temperature was increased slowly to room temperature overnight. Water and ethyl acetate were added to the mixture and the aqueous layer was extracted 3 times. Combined organic phases was dried over MgSO₄, filtrated and evaporated to give the 5-[1,3]Dioxolan-2-yl-benzofuran-2-carboxylic acid methyl ester (31.9 mg, 44%) mixed with the dimer (expected product/dimer 46:54). The mixture was used directly in the next step.

LC-MS: M/Z ESI: 1.54 min, 249.26 (M+1) and 1.88 min, 407.20 (M+1, Dimer).

Intermediate 74:
3-Bromo-2-fluoro-benzofuran-5-carbaldehyde

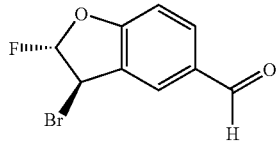

Benzofuran-5-carbaldehyde (100 mg, 0.68 mmol) in ether (1 mL) was added to a cold solution (−78° C.) of NBS (158 mg, 1.3 eq) and pyridinium poly(hydrogen fluoride) 70% (0.850 mL) in ether (4 mL) in a polypropylene tube. The reaction was allowed to warm up to room temperature overnight. The reaction mixture was poured into ice water and extracted with ether. The ether phase was washed with aqueous bicarbonate, dried over sodium sulfate, filtrated and evaporated to give 3-bromo-2-fluoro-benzofuran-5-carbaldehyde (141.6 mg). It was purified on reverse phase HPLC (solvents gradient H₂O/CH₃CN 0.1% TFA) affording the title compound (62 mg, 37%), which was used in the next step.

LC-MS: M/Z ESI: 1.56 min. HPLC=3.11 min (99.34%). ¹H NMR: (DMSO-d6) δ 9.94 (s, 1H), 8.09 (d, 1H, ³J=1.8 Hz), 7.99 (dd, 1H, ³J=8.4, 1.8 Hz), 7.38 (d, 1H, ³J=8.4 Hz), 6.87 (d, 1H, ²J$_{H-F}$=59 Hz), 6.01 (d, 1H, ³J$_{H-F}$=15.1 Hz). ¹⁹F NMR: (DMSO-d6) δ-114.80, −114.88.

Intermediate 75:
2-Fluoro-5-[1,3]dioxolan-2-yl-benzofuran

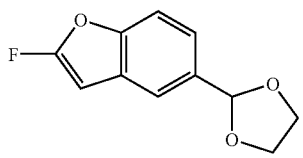

5-[1,3]Dioxolan-2-yl-benzofuran (50 mg, 0.26 mmol) was dissolved in THF (2 mL) and the solution was cooled down to −78° C. Butyl lithium (180 uL, 1.1 eq.) was added dropwise. This mixture was stirred 30 min at 25° C. Then the reaction mixture was cooled down to −78° C. and N-fluorodibenzenesulfonamide (91 mg, 1.1 eq.), dissolved in 1 mL THF, was added dropwise to the reaction mixture. The mixture was stirred overnight between −78° C. and room temperature. Water and ethyl acetate were added to the mixture and the aqueous layer was extracted 3 times. Combined organic phases was dried over MgSO₄, filtrated and evaporated, to give the 2-Fluoro-5-[1,3]dioxolan-2-yl-benzofuran (75 mg) mixed with side products. However it was sufficiently pure to be used for the next step.

The following examples have been synthesized:

Example 1

Preparation of 5-(1,3-benzodioxol-5-ylmethylene)-1,3-thiazolidine-2,4-dione

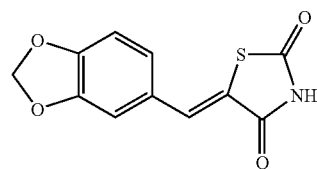

In a 100 ml round bottom flask were placed 20 g of thiazolidine, 15.6 g of piperonal and 7.7 g of beta-alanine in 80 ml of acetic acid. The reaction was stirred for 3 h at 100° C. and then slowly cooled to room temperature, while the desired condensation product crystallized. The crystals were filtered, washed with acetic acid (rt.) and water than recrystallized from DME (25 ml), affording 28 g (84%) of pure 5-(1,3-benzodioxol-5-ylmethylene)-1,3-thiazolidine-2,4-dione.

The corresponding potassium salt was obtained via the following route: 5-(1,3-benzodioxol-5-ylmethylene)-1,3-thiazolidine-2,4-dione was suspended in THF, followed by the addition of 1N solution of KOH in water (1.0 eq.). A clear solution has been obtained, which upon lyophilization gave pure potassium salt of 5-(1,3-benzodioxol-5-ylmethylene)-1,3-thiazolidine-2,4-dione.

HPLC: 3.48 min. LC-MS: M/Z ESI: 1.31 min, 248.12 (M−1). NMR (parent): ¹H NMR (DMSO-d6) δ 12.5 (br. s, 1H), 7.71 (s, 1H), 7.06-7.16 (m, 3H), 6.12 (s, 2H).

In cases were the final compounds did not crystallize from the reaction solutions, small quantities of water were added, leading to the precipitation of the desired condensation product.

The crude either precipitated pure enough from the reaction mixture, or was recrystallized from an appropriate solvent like DME, methanol, EtOAc or purified by flash-chromatography using EtOAc, cyclohexane mixtures as eluents.

Alternatively the final compounds could be synthesized in a parallel manner according to the following protocol:

In a parallel synthesizer Quest 210™ was placed the corresponding aldehyde, to which was added a mixture of piperidine (17.9 mg/tube) and 2,4-thiazolidinedione (49.2 mg/tube) in DME (2 ml/tube). The reactions were stirred for 3 h at 120° C. and then cooled to room temperature under agitation. 2 ml of H₂O were added. Those compounds, which precipitated were filtered off via the lower manifold. The remaining clear solutions were reduced in volume, followed by the addition of water. The so formed solids were filtered and washed with little amount of DME, affording pure condensation products.

Example 2

Preparation of 5-(1,3-benzodioxol-5-ylmethylene)-2-thioxo-1,3-thiazolidin-4-one

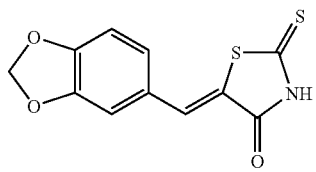

In a 24 ml vial was placed 1 g of commercially available rhodanine, 1.3 g of piperonal and 0.5 ml of TEA in 10 ml of DME. The reaction was stirred for 5 h at 120° C. and then cooled to room temperature upon which the final product precipitated. The solid was filtered and washed with DME affording 1.6 g (80%) of orange powder.

LC-MS: M/Z ESI: 1.46 min, 266.00 (M+1), 264.08 (M−1). NMR (parent): $^1$H NMR (DMSO-d6) δ 13.75 (br. s, 1H), 7.58 (s, 1H), 7.08-7.18 (m, 3H), 6.14 (s, 2H).

Example 3

Preparation of 5-(2,3-dihydro-1,4-benzodioxin-6-ylmethylene)-1,3-thiazolidine-2,4-dione

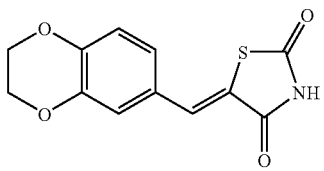

Following the general method as outlined in Example 1, starting from 2,3-dihydro-1,4-benzodioxin-6-carbaldehyde and 1,3-thiazolidine-2,4-dione, the title compound was obtained.

HPLC: 2.58 min. LC-MS: M/Z ESI: 1.32 min, 262.16 (M−1). $^1$H NMR (DMSO-d6) δ 12.52 (br. s, 1H), 7.68 (s, 1H,), 7.09 (dd, 2H, J=1.9, 7.1), 7.00 (d, 1H, J=9.0 Hz), 4.36-4.22 (m, 4H).

Example 4

Preparation of 5-(2,3-dihydro-1-benzofuran-5-ylmethylene-1,3-thiazolidine-2,4-dione

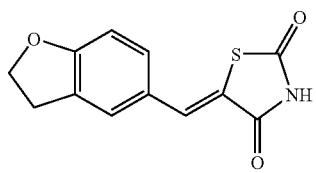

Following the general method as outlined in Example 1, starting from 2,3-dihydro-1-benzofuran-5-carbaldehyde and 1,3-thiazolidine-2,4-dione, the title compound was obtained.

HPLC: 3.27 min. LC-MS: M/Z ESI: 1.37 min, 246.18 (M−1). $^1$H NMR: (DMSO-d6) δ 9.80 (br. s, 1H), 7.37 (s, 1H,), 7.25 (d, 1H, J=8.3), 7.21 (s, 1H), 6.80 (d, 1H, J=8.3 Hz), 4.54 (t, 2H, J=8.85), 3.19 (t, 2H, J=8.85)

Example 5

Preparation of 5-[(7-methoxy-1,3-benzodioxol-5-yl)methylene]-1,3-thiazolidine-2,4-dione

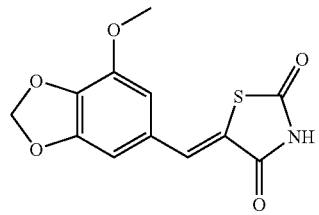

Following the general method as outlined in Example 1, starting from 7-methoxy-1,3-benzodioxol-5-yl)carbaldehyde and 1,3-thiazolidine-2,4-dione, the title compound was obtained.

HPLC: 3.57 min. LC-MS: M/Z ESI: 1.30 min, 278.07 (M−1). $^1$H NMR: (DMSO-d6) δ 12.63 (br. s, 1H), 7.78 (s, 1H,), 7.65 (s, 1H), 7.57 (d, 1H, J=8.5 Hz), 7.45 (dd, 2H, J=0.8, 7.6).

Example 6

Preparation of 5-[(9,10-dioxo-9,10-dihydroanthracen-2-yl methylene]-1,3-thiazolidine-2,4-dione

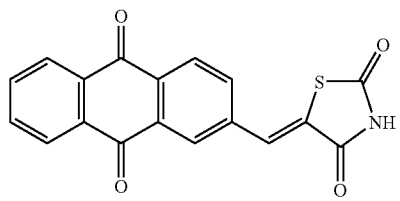

Following the general method as outlined in Example 1, starting from (9,10-dioxo-9,10-dihydroanthracen-2-yl)carbaldehyde and 1,3-thiazolidine-2,4-dione, the title compound was obtained.

HPLC: 4.12 min. LC-MS: M/Z ESI: 1.50 min, 334.09 (M−1).

Example 7

Preparation of (5-[(2,2-difluoro-1,3-benzodioxol-5-yl)methylene]-1,3-thiazolidine-2,4-dione

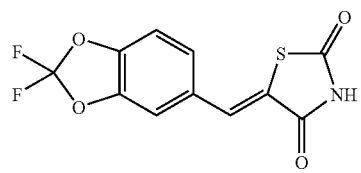

Following the general method as outlined in Example 1, starting from (2,2-difluoro-1,3-benzodioxol-5-yl)carbaldehyde and 1,3-thiazolidine-2,4-dione, the title compound was obtained.

HPLC: 3.85 min. LC-MS (10 min.): M/Z ESI: 3.15 min, 284.11 (M−1). ¹H NMR: (DMSO-d6) δ 12.63 (br. s, 1H), 7.78 (s, 1H,), 7.65 (s, 1H), 7.57 (d, 1H, J=8.5 Hz), 7.45 (dd, 2H, J=0.8, 7.6)

Example 8

Preparation of 5-(1,3-dihydro-2-benzofuran-5-ylmethylene)-1,3-thiazolidine-2,4-dione

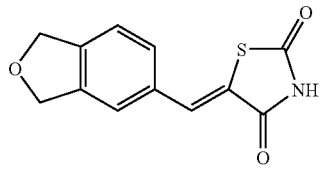

Following the general method as outlined in Example 1, starting from 1,3-dihydro-2-benzofuran-5-carbaldehyde (intermediate 4) and 1,3-thiazolidine-2,4-dione, the title compound was obtained.

HPLC: 2.89 min. LC-MS: M/Z ESI: 1.20 min, 246.20 (M−1). ¹H NMR: (DMSO-d6) δ 12.60 (br. s, 1H), 7.80 (s, 1H,), 7.56-7.42 (m, 2H), 5.03 (s, 4H)

Example 9

Preparation of 5-(1-benzofuran-5-ylmethylene)-1,3-thiazolidine-2,4-dione

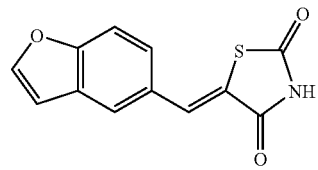

Following the general method as outlined in Example 1, starting from 1-benzofuran-5-carbaldehyde (intermediate 1) and 1,3-thiazolidine-2,4-dione, the title compound was obtained.

HPLC: 3.54 min. LC-MS: M/Z ESI: 1.47 min, 244.20 (M−1). ¹H NMR: (DMSO-d6) δ 12.58 (br. s, 1H), 8.10 (d, 1H, J=2.2 Hz), 7.92 (s, 2H), 7.74 (d, 1H, J=8.6 Hz), 7.57 (d, 1H, J=8.6 Hz), 7.07 (s, 1H)

Example 10

Preparation of 5-[(4-methyl-3-oxo-3,4-dihydro-2H-1,4-benzoxazin-6-ylmethylene]-1,3-thiazolidine-2,4-dione

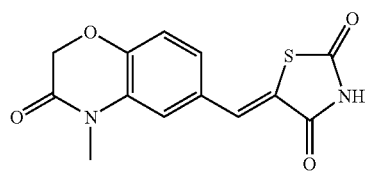

Following the general method as outlined in Example 1, starting from [(4-methyl-3-oxo-3,4-dihydro-2H-1,4-benzoxazin-6-yl)carbaldehyde (intermediate 2) and 1,3-thiazolidine-2,4-dione, the title compound was obtained.

HPLC: 2.79 min. LC-MS: M/Z ESI: 1.19 min, 289.22 (M−1). ¹H NMR: (DMSO-d6) δ 12.58 (br. s, 1H), 7.81 (s, 1H), 7.41 (s, 1H), 7.13-7.26 (d, 2H), 4.74 (s, 2H), 2.99 (s, 3H)

Example 11

Preparation of 5-(1,3-benzodioxol-5-ylmethylene)-2-imino-1,3-thiazolidine-4-one

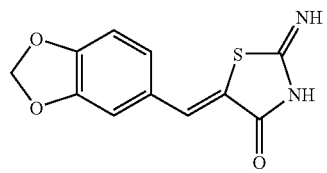

Following the general method as outlined in Example 1, starting from 1,3-benzodioxol-5-carbaldehyde and 2-imino-1,3-thiazolidin-4-one, the title compound was obtained.

HPLC: 2.29 min. LC-MS: M/Z ESI: 1.21 min, 247.25 (M−1).

Example 12

Preparation of 5-Quinolin-6-ylmethylene-thiazolidine-2,4-dione

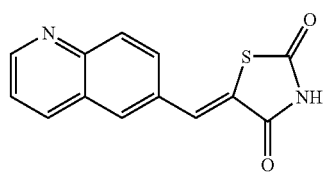

Following the general method as outlined in Example 1, starting from quinoline-6-carbaldehyde (intermediate 5) and 1,3-thiazolidine-2,4-dione, the title compound was obtained.

HPLC: 1.445 min. LC-MS: M/Z ESI: 1.17 min, 257.21 (M+1). ¹H NMR: (DMSO-d6) δ 8.88 (d, J=6 Hz, 1H), 8.40 (d, J=9 Hz, 1H), 8.07-7.90 (m, 3H), 7.55 (q, J=6 Hz, 9 Hz, 1H), 7.45 (s, 1H).

Example 13

5-Quinolin-6-ylmethylene-2-thioxo-thiazolidin-4-one

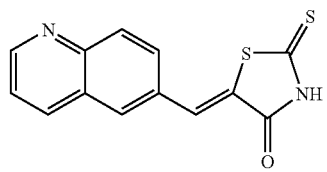

Following the general method as outlined in Example 1, starting from quinoline-6-carbaldehyde (intermediate 5) and rhodanine, the title compound was obtained.

HPLC: 2.05 min. LC-MS: M/Z ESI: 1.25 min, 273.14 (M+1). ¹H NMR: (DMSO-d6) δ 14.00 (br. s, 1H), 8.97 (d, J=2.3 Hz, 1H), 8.23 (d, J=9 Hz, 1H), 8.10 (d, J=9 Hz, 1H), 7.95 (d, J=9 Hz, 1H), 7.79 (s, 1H), 7.61 (q, J=3 Hz, 9 Hz, 1H).

Example 14

2-Imino-5-quinolin-6-ylmethylene-thiazolidin-4-one

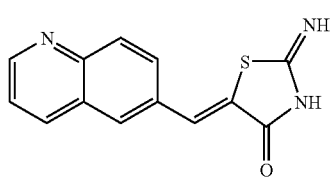

Following the general method as outlined in Example 1, starting from quinoline-6-carbaldehyde (intermediate 5) and 2-imino-1,3-thiazolidin-4-one, the title compound was obtained.

HPLC: 1.16 min. LC-MS: M/Z ESI: 1.10 min, 256.18 (M+1). $^1$H NMR: (DMSO-d6) δ 12.58 (br. s, 1H), 8.84 (s, 1H), 8.37 (d, J=6 Hz, 1H), 8.02-7.86 (m, 3H), 7.52 (q, J=6 Hz, 9 Hz, 1H), 7.26 (s, 1H), 7.02 (b. s, 1H).

Example 15

5-(3-Methyl-benzo[d]isoxazol-5-ylmethylene)-thiazolidine-2,4-dione

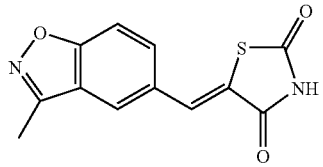

Following the general method as outlined in Example 1, starting from 3-Methyl-benzo[d]isoxazole-5-carbaldehyde (intermediate 6) and 1,3-thiazolidine-2,4-dione, the title compound was obtained.

HPLC: 2.99 min. LC-MS: M/Z ESI: 1.30 min, 259.17 (M−1). $^1$H NMR: (DMSO-d6) δ 12.58 (br. s, 1H), 8.08 (s, 1H), 7.95 (s, 1H), 7.85 (s, 2H), 2.59 (s, 3H).

Example 16

5-(4-Phenyl-quinazolin-6-ylmethylene)-thiazolidine-2,4-dione

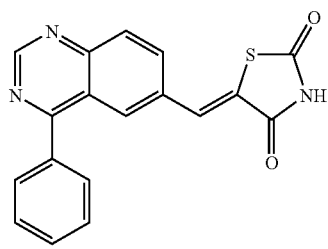

Following the general method as outlined in Example 1, starting from 4-Phenyl-quinazoline-6-carbaldehyde (intermediate 13) and 1,3-thiazolidine-2,4-dione, the title compound was obtained.

HPLC: 3.45 min. LC-MS: M/Z ESI: 1.25 min, 334.15 (M+1). $^1$H NMR: (DMSO-d6) δ 12.74 (br. s, 1H), 9.43 (s, 1H), 8.24 (m, 2H), 8.00-7.86 (m, 2H), 7.72-7.66 (m, 5H).

Example 17

5-(4-Dimethylamino-quinazolin-6-ylmethylene)-thiazolidine-2,4-dione

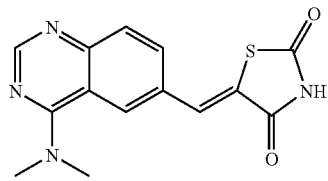

Following the general method as outlined in Example 1, starting from 4-Dimethylamino-quinazoline-6-carbaldehyde (intermediate 14) and 1,3-thiazolidine-2,4-dione, the title compound was obtained.

HPLC: 1.47 min. LC-MS: M/Z ESI: 1.26 min, 301.26 (M+1). $^1$H NMR: (DMSO-d6) δ 8.81 (s, 1H), 8.54 (s, 1H), 8.16-7.95 (m, 3H), 7.13-7.26 (d, 2H), 3.63 (s, 6H).

The following examples were synthesized as described in Example 1 and 17 starting from intermediates 15 to 31 and 1,3-thiazolidine-2,4-dione

| Example | Intermediate# as starting material | Compound name | Mass (M + 1) |
|---|---|---|---|
| 18 | 16 | 5-[(4-aminoquinazolin-6-yl)methylene]-1,3-thiazolidine-2,4-dione | 273.29 |
| 19 | 15 | 5-[(4-piperidin-1-ylquinazolin-6-yl)methylene]-1,3-thiazolidine-2,4-dione | 341.40 |
| 20 | 22 | 5-[(4-morpholin-4-ylquinazolin-6-yl)methylene]-1,3-thiazolidine-2,4-dione | 343.20 |
| 21 | 17 | 5-{[4-(benzylamino)quinazolin-6-yl]methylene}-1,3-thiazolidine-2,4-dione | 363.10 |
| 22 | 21 | 5-{[4-(diethylamino)quinazolin-6-yl]methylene}-1,3-thiazolidine-2,4-dione | 329.30 |

-continued

| Example | Intermediate# as starting material | Compound name | Mass (M + 1) |
|---|---|---|---|
| 23 | 18 | 5-({4-[(pyridin-2-ylmethyl)amino]quinazolin-6-yl}methylene)-1,3-thiazolidine-2,4-dione | 364.40 |
| 24 | 19 | 5-({4-[(pyridin-3-ylmethyl)amino]quinazolin-6-yl}methylene)-1,3-thiazolidine-2,4-dione | 364.40 |
| 25 | 23 | ethyl 1-{6-[(2,4-dioxo-1,3-thiazolidin-5-ylidene)methyl]quinazolin-4-yl}piperidine-3-carboxylate | 413.20 |
| 26 | 25 | ethyl 1-{6-[(2,4-dioxo-1,3-thiazolidin-5-ylidene)methyl]quinazolin-4-yl}piperidine-4-carboxylate | 413.30 |
| 27 | 24 | tert-butyl 1-{6-[(2,4-dioxo-1,3-thiazolidin-5-ylidene)methyl]quinazolin-4-yl}-L-prolinate | 427.20 |
| 28 | 20 | 5-{[4-(4-methylpiperazin-1-yl)quinazolin-6-yl]methylene}-1,3-thiazolidine-2,4-dione | 356.13 |
| 29 | 31 | 5-{[4-(4-pyrimidin-2-ylpiperazin-1-yl)quinazolin-6-yl]methylene}-1,3-thiazolidine-2,4-dione | 420.20 |
| 30 | 30 | 5-({4-[4-(4-fluorophenyl)piperidin-1-yl]quinazolin-6-yl}methylene)-1,3-thiazolidine-2,4-dione | 435.30 |
| 31 | 29 | 5-{[4-(4-benzylpiperidin-1-yl)quinazolin-6-yl]methylene}-1,3-thiazolidine-2,4-dione | 431.30 |
| 32 | 28 | 5-({4-[4-(2-phenylethyl)piperidin-1-yl]quinazolin-6-yl}methylene)-1,3-thiazolidine-2,4-dione | 445.40 |
| 33 | 27 | 5-{[4-(4-methylpiperidin-1-yl)quinazolin-6-yl]methylene}-1,3-thiazolidine-2,4-dione | 355.20 |
| 34 | 26 | 5-{[4-(4-hydroxypiperidin-1-yl)quinazolin-6-yl]methylene}-1,3-thiazolidine-2,4-dione | 357.40 |

Example 35

1-[6-(2,4-Dioxo-thiazolidin-5-ylidenemethyl)-quinazolin-4-yl]-piperidine-4-acid

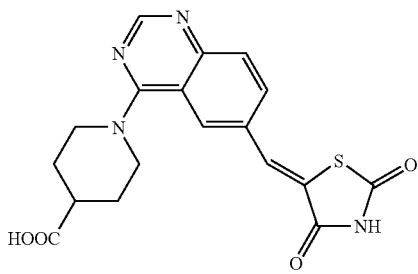

50 mg of Ethyl 1-{6-[(2,4-dioxo-1,3-thiazolidin-5-ylidene)methyl]quinazolin-4-yl}piperidine-4-carboxylate (example 26) was dissolved in 2 ml solution of THF/water (1/1). A few drops of 5N NaOH were added, and the reaction was stirred for 12 h at rt. After completion of the reaction, solvents were evaporated and titled compound was precipitated in diethylether as a yellow solid (40 mg, 82%).

HPLC: 1.43 min. LC-MS: M/Z ESI: 1.15 min, 385.20 (M+1).

Example 36

1-[6-(2,4-Dioxo-thiazolidin-5-ylidenemethyl)-quinazol-4-yl]-piperidine-3-carboxylic acid

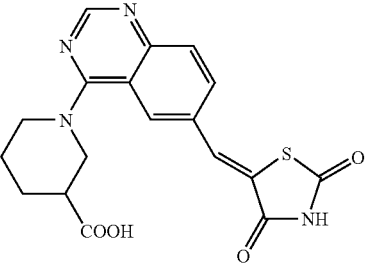

Following the general method as outlined in Example 35, the title compound was obtained.

HPLC:1.50 min. LC-MS: M/Z ESI: 1.10 min, 385.40 (M+1).

Example 37

1-[6-(2,4-Dioxo-thiazolidin-5-ylidenemethyl)-quinazolin-4-yl]-pyrrolidine-2-carboxylic acid

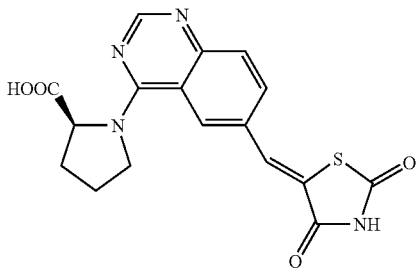

10 mg of tert-butyl 1-{6-[(2,4-dioxo-1,3-thiazolidin-5-ylidene)methyl]quinazolin-4-yl}-L-prolinate (example 27) was stirred in a 25% (TFA/DCM) solution for 12 h at rt. The solvents were evaporated under vacuo and expected compound was precipitated with diethyl ether to give pure 1-[6-(2,4-Dioxo-thiazolidin-5-ylidenemethyl)-quinazolin-4-yl]-pyrrolidine-2-carboxylic acid (7 mg, 81%).

HPLC: 1.43 min. LC-MS: M/Z ESI: 1.10 min, 371.30 (M+1).

Example 38

5-(4-Methylamino-quinazolin-6-ylmethylene)-thiazolidine-2,4-dione

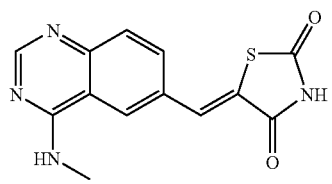

Following the general method as outlined in Example 1, starting from 4-methylamino-quinazoline-6-carbaldehyde (intermediate 11) and 1,3-thiazolidine-2,4-dione, the title compound was obtained.

HPLC: 1.43 min. LC-MS: M/Z ESI: 1.03 min, 287.19 (M+1). $^1$H NMR: (DMSO-d6) δ 11.97 (br. s, 1H), 8.53 (br. s, 2H), 8.37 (s, 1H), 7.92 (d, J=8 Hz, 1H), 7.76 (s, 2H), 3.03 (s, 3H)

Example 39

5-(4-Methoxy-quinazolin-6-ylmethylene)-thiazolidine-2,4-dione

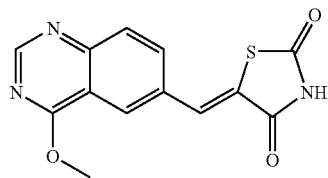

Following the general method as outlined in Example. 1, starting from 4-methoxy-quinazoline-6-carbaldehyde (intermediate 10) and 1,3-thiazolidine-2,4-dione, the title compound was obtained.

HPLC: 2.57 min. LC-MS: M/Z ESI: 1.12 min, 288.20 (M+1). $^1$H NMR: (DMSO-d6) δ 12.74 (br. s, 1H), 8.86 (s, 1H), 8.32 (s, 1H), 8.11 (m, 1H), 8.03-7.98 (m, 2H), 4.18 (s, 3H)

Example 40

2-Imino-5-(4-methylamino-quinazolin-6-ylmethylene)-thiazolidin-4-one

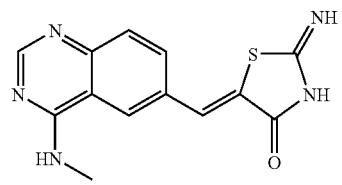

Following the general method as outlined in Example 1, starting from 4-methylamino-quinazoline-6-carbaldehyde (intermediate 11) and 2-imino-1,3-thiazolidin-4-one, the title compound was obtained.

HPLC: 2.43 min. LC-MS: M/Z ESI: 1.07 min, 286.14 (M+1).

Example 41

2-Imino-5-(4-piperidine-quinazolin-6-ylmethylene)-thiazolidin-4-one

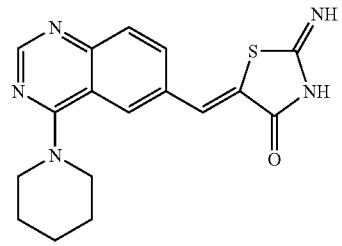

Following the general method as outlined in Example 1, starting from 4-piperidine-quinazoline-6-carbaldehyde (intermediate 72) and 2-imino-1,3-thiazolidin-4-one, the title compound was obtained.

HPLC: 1.78 min. LC-MS: M/Z ESI: 1.40 min, 340.26 (M+1). $^1$H NMR: (DMSO-d6) δ 8.76 (s, 1H), 8.18 (s, 1H), 8.16 (d, J=6 Hz, 1H), 7.88 (d, J=9 Hz, 1H), 7.80 (s, 1H), 4.09 (s, 4H), 1.80 (s, 6H).

Example 42

2-Imino-5-(4-dimethylamino-quinazolin-6-ylmethylene)-thiazolidin-4-one

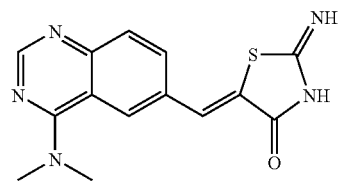

Following the general method as outlined in Example 1, starting from 4-piperidine-quinazoline-6-carbaldehyde (intermediate 14) and 2-imino-1,3-thiazolidin-4-one, the title compound was obtained.

HPLC: 1.32 min. LC-MS (10 min.): M/Z ESI: 1.54 min, 300.23 (M+1). $^1$H NMR: (DMSO-d6) δ 8.82 (s, 1H), 8.53 (s, 1H), 8.16 (d, J=9 Hz, 1H), 7.87 (t, J=9 Hz, 2H), 3.65 (s, 6H).

Example 43

5-(2-Methyl-2H-benzotriazol-5-ylmethylene)-thiazolidine-2,4-dione

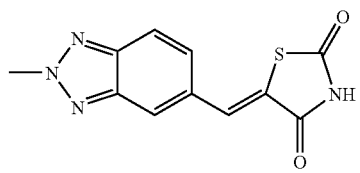

Following the general method as outlined in Example 1, starting from 2-Methyl-2H-benzotriazole-5-carbaldehyde (intermediate 33) and thiazolidinedione, the title compound was obtained.

HPLC: 2.68 min. $^1$H NMR: (DMSO-d6) δ 12.58 (br. s, 1H), 7.98 (s, 1H), 7.92 (d, J=9 Hz, 1H), 7.62 (d, J=6 Hz, 1H), 7.43 (s, 1H), 4.48 (s, 3H).

Example 44

5-(3-Methyl-3H-benzotriazol-5-ylmethylene)-thiazolidine-2,4-dione

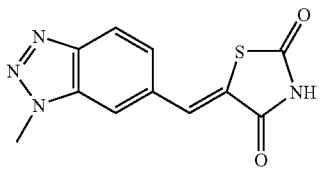

Following the general method as outlined in Example 1, starting from 3-Methyl-3H-benzotriazole-5-carbaldehyde (intermediate 34) and thiazolidinedione, the title compound was obtained.

HPLC: 2.35 min. LC-MS: M/Z ESI: 1.22 min, 259.23 (M−1). $^1$H NMR: (DMSO-d6) δ 12.58 (br. s, 1H), 8.17 (d, J=9 Hz, 1H), 8.07 (s, 1H), 7.62 (d, J=6 Hz, 1H), 7.47 (s, 1H), 4.33 (s, 3H).

Example 45

5-(3-Ethyl-3H-benzimidazol-5-ylmethylene)-thiazolidine-2,4-dione

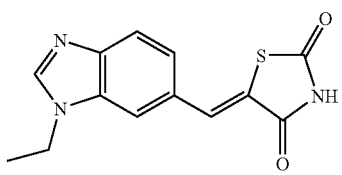

5(4-Amino-3-ethylamino-benzylidene)-thiazolidine-2,4-dione (50 mg, 0.19 mmol) (intermediate 36) was dissolved in formic acid (5 mL) and the solution stirred at 100° C. over night. Formic acid was then removed in vacuo. The crude residue was then purified by silica gel column to give the title compound (35 mg, 63%).

HPLC: 1.71 min. LC-MS: M/Z ESI: 0.82 min, 274.21 (M+1).

The following examples were synthesized as described in Example 45 starting from intermediates 37 to 54 and 1,3-thiazolidine-2,4-dione.

| Example | Intermediate# as starting material | Compound name | Mass(M + 1) |
|---|---|---|---|
| 46 | 37 | 5-{[1-(4-phenylbutyl)-1H-benzimidazol-6-yl]methylene}-1,3-thiazolidine-2,4-dione | 378.30 |
| 47 | 50 | 5-[(1-prop-2-yn-1-yl-1H-benzimidazol-6-yl)methylene]-1,3-thiazolidine-2,4-dione | 284.24 |
| 48 | 38 | 5-[(1-{2-[4-(trifluoromethyl)phenyl]ethyl}-1H-benzimidazol-6-yl)methylene]-1,3-thiazolidine-2,4-dione | 418.17 |
| 49 | 39 | 5-({1-[2-(4-hydroxyphenyl)ethyl]-1H-benzimidazol-6-yl}methylene)-1,3-thiazolidine-2,4-dione | 366.26 |
| 50 | 40 | methyl 4-{6-[(2,4-dioxo-1,3-thiazolidin-5-ylidene)methyl]-1H-benzimidazol-1-yl}cyclohexanecarboxylate | 386.35 |
| 51 | 41 | 5-({1-[2-(5-methoxy-1H-indol-3-yl)ethyl]-1H-benzimidazol-6-yl}methylene)-1,3-thiazolidine-2,4-dione | 419.21 |
| 52 | 42 | 5-({1-[(1-methyl-1H-pyrazol-4-yl)methyl]-1H-benzimidazol-6-yl}methylene)-1,3-thiazolidine-2,4-dione | 340.99 |
| 53 | 43 | 5-({1-[2-(3,4-dimethoxyphenyl)ethyl]-1H-benzimidazol-6-yl}methylene)-1,3-thiazolidine-2,4-dione | 410.37 |
| 54 | 54 | 5-({1-[2-(4-phenoxyphenyl)ethyl]-1H-benzimidazol-6-yl}methylene)-1,3-thiazolidine-2,4-dione | 442.51 |
| 55 | 44 | 5-({1-[4-(trifluoromethyl)benzyl]-1H-benzimidazol-6-yl}methylene)-1,3-thiazolidine-2,4-dione | 404.16 |

| Example | Intermediate# as starting material | Compound name | Mass(M + 1) |
|---|---|---|---|
| 56 | 45 | 4-{6-[(2,4-dioxo-1,3-thiazolidin-5-ylidene)methyl]-1H-benzimidazol-1-yl}cyclohexanecarboxylic acid | 372.18 |
| 57 | 46 | 5-[(1-isobutyl-1H-benzimidazol-6-yl)methylene]-1,3-thiazolidine-2,4-dione | 302.25 |
| 58 | 47 | 5-({1-[2-(1,3-benzodioxol-4-yl)ethyl]-1H-benzimidazol-6-yl}methylene)-1,3-thiazolidine-2,4-dione | 394.27 |
| 59 | 48 | 5-({1-[2-(2-phenoxyphenyl)ethyl]-1H-benzimidazol-6-yl}methylene)-1,3-thiazolidine-2,4-dione | 442.29 |
| 60 | 49 | 5-{[1-(3,3-diphenylpropyl)-1H-benzimidazol-6-yl]methylene}-1,3-thiazolidine-2,4-dione | 440.27 |
| 61 | 51 | 5-{[1-(2-methoxybenzyl)-1H-benzimidazol-6-yl]methylene}-1,3-thiazolidine-2,4-dione | 366.33 |
| 62 | 52 | 5-{[1-(3-furylmethyl)-1H-benzimidazol-6-yl]methylene}-1,3-thiazolidine-2,4-dione | 326.24 |
| 63 | 53 | 5-[(1-propyl-1H-benzimidazol-6-yl)methylene]-1,3-thiazolidine-2,4-dione | 288.18 |

Example 64

5-Quinoxalin-6-ylmethylene-thiazolidine-2,4-dione

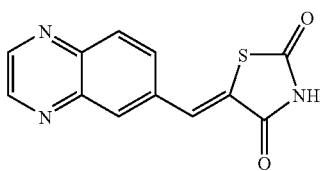

Following the general method as outlined in Example 1, starting from quinoxaline-6-carbaldehyde (intermediate 55) and thiazolidinedione, the title compound was obtained.

HPLC: 2.48 min. LC-MS: M/Z ESI: 1.01 min, 256.20 (M−1). $^1$H NMR: (DMSO-d6) δ 12.58 (br. s, 1H), 8.93 (d, J=9 Hz, 2H), 8.18 (s, 1H), 8.10 (d, J=9 Hz, 1H), 8.03 (d, J=9 Hz, 1H), 7.51 (s, 1H).

Example 65

5-Quinoxalin-6-ylmethylene-2-thioxo-thiazolidin-4-one

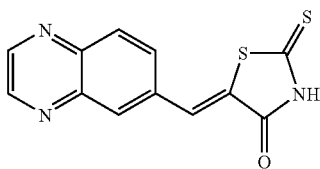

Following the general method as outlined in Example 1, starting from quinoxaline-6-carbaldehyde (intermediate 55) and rhodanine, the title compound was obtained.

HPLC: 3.10 min. LC-MS: M/Z ESI: 1.17 min, 272.13 (M−1). $^1$H NMR: (DMSO-d6) δ 12.00 (br. s, 1H), 9.02 (s, 2H), 8.31 (s, 1H), 8.21 (d, J=9 Hz, 1H), 8.04 (d, J=9 Hz, 1H), 7.90 (s, 1H)

Example 66

2-Imino-5-quinoxalin-6-ylmethylene-thiazolidin-4-one

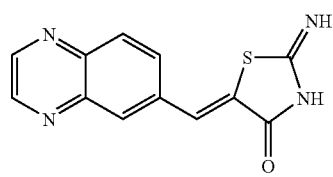

Following the general method as outlined in Example 1, starting from quinoxaline-6-carbaldehyde (intermediate 55) and 2-imino-1,3-thiazolidin-4-one, the title compound was obtained.

HPLC: 1.97 min. LC-MS: M/Z ESI: 1.02 min, 255.19 (M−1). $^1$H NMR: (DMSO-d6) δ9.57-9.30 (b. d, J=81 Hz, 2H), 9.00 (s, 2H), 8.26-8.07 (m, 3H), 7.84 (s, 1H).

Example 67

5-Benzothiazol-6-ylmethylene-thiazolidine-2,4-dione

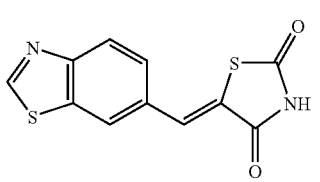

Following the general method as outlined in Example 1, starting from quinoxaline-6-carbaldehyde (intermediate 56) and thiazolidinedione, the title compound was obtained.

HPLC: 2.85 min. LC-MS: M/Z ESI: 1.06 min, 261.11 (M−1). $^1$H NMR: (DMSO-d6) δ 12.58 (br. s, 1H), 9.39 (s, 1H), 8.27 (s, 1H), 8.11 (d, J=9 Hz, 1H), 7.70 (d, J=9 Hz, 1H), 7.42 (s, 1H).

Example 68

5-(3-Methyl-benzofuran-5-ylmethylene)-thiazolidine-2,4-dione

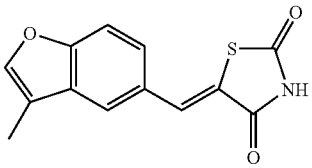

Following the general method as outlined in Example 1, starting from 3-Methyl-benzofuran-5-carbaldehyde (intermediate 57) and 1,3-thiazolidine-2,4-dione, the title compound was obtained.

HPLC: 1.47 min. LC-MS: M/Z ESI: 1.15 min, 257.21 (M−1). $^1$H NMR: (DMSO-d6) δ 12.50 (br. s, 1H), 8.87 (d, J=6 Hz, 1H), 8.38 (d, J=9 Hz, 1H), 8.07 (t, J=12 Hz, 2H), 7.92 (d, J=9 Hz, 1H), 7.53 (q, J=6 Hz, 12 Hz, 1H), 7.45 (s, 1H).

Example 69

5-(2-Bromo-3-methyl-benzofuran-5-ylmethylene)-thiazolidine-2,4-dione

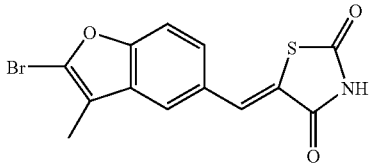

In a 25 ml 3 neck flask was placed 5-(3-methyl-benzofuran-5-ylmethylene)-thiazolidine-2,4-dione (100 mg, 0.39 mmol) (example 68) and Br2 (20 ul, 1 eq.) in 2 ml of AcOH at 0° C. The mixture was allowed to warm to room temperature. After 2 h at room temperature another equivalent of Br$_2$ was added. After 3 h the reaction was filtered off to obtain a yellow product being the title compound (87 mg, 66%).

LC-MS: M/Z ESI: 1.69 min, 339.8 (M+1). $^1$H NMR: (DMSO-d6) δ12.50 (br. s, 1H), 7.93 (s, 1H), 7.82 (s, 1H), 7.72 (d, J=6 Hz, 1H), 7.54 (d, J=6 Hz, 1H), 2.20 (s, 3H).

Example 70

5-(3-bromo-benzofuran-5-ylmethylene)-thiazolidine-2,4-dione

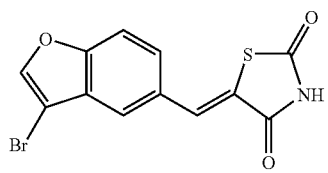

Following the general method as outlined in Example 1, starting from 3-Bromo-benzofuran-5-carbaldehyde (intermediate 58) and 1,3-thiazolidine-2,4-dione, the title compound was obtained.

HPLC: 3.92 min. LC-MS: M/Z ESI: 1.57 min, 325.17 (M+1). $^1$H NMR: (DMSO-d6) δ 12.60 (br. s, 1H), 8.42 (s, 1H), 8.00 (s, 1H), 7.85 (d, J=23 Hz, 1H), 7.76 (s, 1H), 7.63 (d, J=23 Hz, 1H).

Example 71

3-[5-(2,4-Dioxo-thiazolidin-5-ylidenemethyl)-benzofuran-3-yl]-acrylic acid ethyl ester

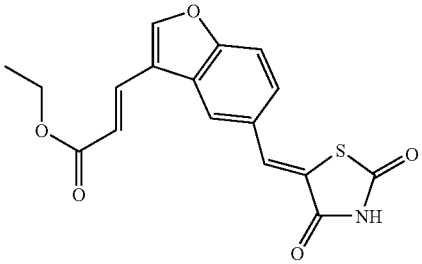

Following the general method as outlined in Example 1, starting from 3-(5-Formyl-benzofuran-3-yl)-acrylic acid ethyl ester (intermediate 60) and 1,3-thiazolidine-2,4-dione, the title compound was obtained.

HPLC: 4.00 min. LC-MS: M/Z ESI: 1.60 min, 342.20 (M−1). $^1$H NMR: (DMSO-d6) δ 12.50 (br. s, 1H), 8.63 (s, 1H), 8.42 (s, 1H), 8.08 (s, 1H), 7.83 (m, 2H), 7.62 (s, 1H), 4.22 (q, J=6 Hz, 9 Hz, 2H), 1.28 (t, J=9 Hz, 3H).

Example 72

3-[5-(2,4-Dioxo-thiazolidin-5-ylidenemethyl)-benzofuran-3-yl]-acrylic acid

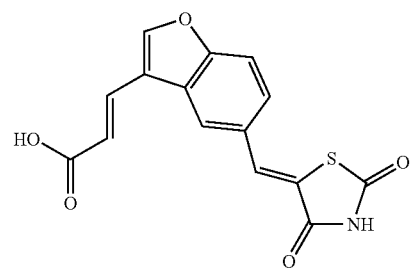

3-[5-(2,4-Dioxo-thiazolidin-5-ylidenemethyl)-benzofuran-3-yl]-acrylic acid ethyl ester (205 mg, 0.6 mmol) (example 71) were dissolved in THF/water 4:2. To this solution was added under stirring 81 mg (4 eq.) of LiOH.H$_2$O. The reaction was stirred for 15 h. The solvents were evaporated, and the residue was precipitated with ether. The solid was washed with 1NHCl and dried to afford 170 mg (90%) of pure 3-[5-(2,4-Dioxo-thiazolidin-5-ylidenemethyl)-benzofuran-3-yl]-acrylic acid.

HPLC: 3.25 min. LC-MS: M/Z ESI: 1.01 min, 314.11 (M−1). $^1$H NMR: (DMSO-d6) δ 8.22 (s, 1H), 8.03 (s, 1H), 7.58 (dd, J=9 Hz, 33 Hz, 2H), 7.43 (s, 1H), 7.25 (d, J=118 Hz, 1H), 7.07 (s, 1H).

Example 73

5-[3-(3-Oxo-3-piperidin-1-yl-propenyl)-benzofuran-5-ylmethylene]-thiazolidine-2,4-dione

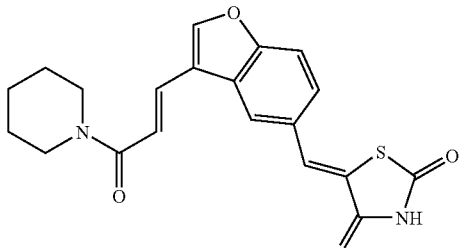

180 mg (0.57 mmol) of 3-[5-(2,4-Dioxo-thiazolidin-5-ylidenemethyl)-benzofuran-3-yl]-acrylic acid (example 72) was suspended in THF (25 ml). To this suspension was added DIEA (2 eq.) and piperidine (3 eq.). Under stirring was added PyBOP (1.5 eq.). After 30 min the reaction mixture became clear, after an additional 1 h a precipitate was formed. The reaction was stirred overnight. The precipitate was filtered off and washed with THF and 1N HCl affording the title compound in high purity.

HPLC: 3.91 min. LC-MS: M/Z ESI: 1.58 min, 383.22 (M+1). $^1$H NMR: (DMSO-d6) δ 8.46 (s, 1H), 8.19 (s, 1H), 7.71-7.51 (m, 4H), 7.23 (d, J=15 Hz, 1H), 3.73 (d, J=48 Hz, 2H), 1.51 (d, J=36 Hz, 3H).

The following amides were synthesized according to the synthesis of example 73.

| Example | Amine as starting material | Compound name | Mass(M + 1) |
| --- | --- | --- | --- |
| 74 | Proline-methylester | Methyl 1-((3-{5-[(2,4-dioxo-1,3-thiazolidin-5-ylidene)methyl]-1-benzofuran-3-yl}prop-2-enoyl)prolinate | 427.15 |
| 75 | D-proline-methylester | Methyl 1-((3-{5-[(2,4-dioxo-1,3-thiazolidin-5-ylidene)methyl]-1-benzofuran-3-yl}prop-2-enoyl)-D-prolinate | 413.15 |
| 76 | Pyrollidine | (5-({3-[(3-oxo-3-pyrrolidin-1-ylprop-1-en-1-yl]-1-benzofuran-5-yl}methylene)-1,3-thiazolidine-2,4-dione | 369.52 |
| 77 | Morpholine | 5-({3-[3-morpholin-4-yl-3-oxoprop-1-en-1-yl]-1-benzofuran-5-yl}methylene)-1,3-thiazolidine-2,4-dione | 385.07 |
| 78 | L-proline-methylester | Methyl 1-(3-{5-[(2,4-dioxo-1,3-thiazolidin-5-ylidene)methyl]-1-benzofuran-3-yl}prop-2-enoyl)-L-prolinate | 427.13 |
| 79 | N-methyl-cyclohexylamine | N-cyclohexyl-3-{5-[(2,4-dioxo-1,3-thiazolidin-5-ylidene)methyl]-1-benzofuran-3-yl}-N-methylacrylamide | 411.12 |
| 80 | N-ethyl-hydroxyethyl-amine | 3-{5-[(2,4-dioxo-1,3-thiazolidin-5-ylidene)methyl]-1-benzofuran-3-yl}-N-ethyl-N-(2-hydroxyethyl)acrylamide | 387.10 |
| 81 | Cyclobutylamine | N-cyclobutyl-3-{5-[(2,4-dioxo-1,3-thiazolidin-5-ylidene)methyl]-1-benzofuran-3-yl}acrylamide | 369.13 |
| 82 | Azetidine | 5-({3-[3-azetidin-1-yl-3-oxoprop-1-en-1-yl]-1-benzofuran-5-yl}methylene)-1,3-thiazolidine-2,4-dione | 355.64 |
| 83 | 1,3-dihydro-2H-isoindole | 5-({3-[3-(1,3-dihydro-2H-isoindol-2-yl)-3-oxoprop-1-en-1-yl]-1-benzofuran-5-yl}methylene)-1,3-thiazolidine-2,4-dione | 415.00 (M − 1) |
| 84 | Azepan | 5-({3-[3-azepan-1-yl-3-oxoprop-1-en-1-yl]-1-benzofuran-5-yl}methylene)-1,3-thiazolidine-2,4-dione | 397.46 |
| 85 | Piperidin-1-ylamine | 3-{5-[(2,4-dioxo-1,3-thiazolidin-5-ylidene)methyl]-1-benzofuran-3-yl}-N-piperidin-1-ylacrylamide | 398.00 |
| 86 | Pyridin-3-yl-methylamine | 3-{5-[(2,4-dioxo-1,3-thiazolidin-5-ylidene)methyl]-1-benzofuran-3-yl}-N-(pyridin-3-ylmethyl)acrylamide | 406.10 |
| 87 | Cyclohexylamine | N-cyclohexyl-3-{5-[(2,4-dioxo-1,3-thiazolidin-5-ylidene)methyl]-1-benzofuran-3-yl}acrylamide | 397.08 |
| 88 | 4-N-methyl-piperazine | 5-({3-[3-(4-methylpiperazin-1-yl)-3-oxoprop-1-en-1-yl]-1-benzofuran-5-yl}methylene)-1,3-thiazolidine-2,4-dione | 398.02 |
| 89 | Cycloheptylamine | N-cycloheptyl-3-{5-[(2,4-dioxo-1,3-thiazolidin-5-ylidene)methyl]-1-benzofuran-3-yl}acrylamide | 411.44 |
| 90 | Pyroline | 5-({3-[3-(2,5-dihydro-1H-pyrrol-1-yl)-3-oxoprop-1-en-1-yl]-1-benzofuran-5-yl}methylene)-1,3-thiazolidine-2,4-dione | 367.11 |
| 91 | Cyclopentylamine | N-cyclopentyl-3-{5-[(2,4-dioxo-1,3-thiazolidin-5-ylidene)methyl]-1-benzofuran-3-yl}acrylamide | 383.11 |

Example 92

3-[5-(2,4-Dioxo-thiazolidin-5-ylidenemethyl)-benzofuran-3-yl]-propionic acid ethyl ester

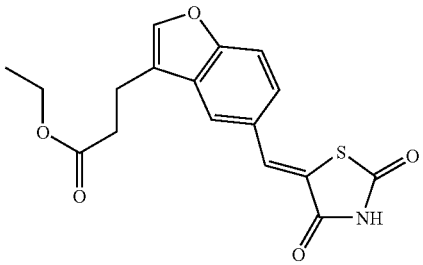

Following the general method as outlined in Example 1, starting from 3-(5-Formyl-benzofuran-3-yl)-propionic acid ethylester (intermediate 71) and 1,3-thiazolidine-2,4-dione, the title compound was obtained.

HPLC: 3.94 nm. LC-MS: M/Z ESI: 2.87 min, 346.15 (M+1). $^1$H NMR: (DMSO-d6) δ 12.58 (br. s, 1H), 7.92 (d, J=6 Hz, 3H), 7.72 (d, J=9 Hz, 1H), 7.53 (d, J=9 Hz, 1H), 4.03 (q, J=9 Hz, 15 Hz, 2H), 2.94 (t, J=9 Hz, 2H), 2.73 (t, J=6 Hz, 2H), 1.14 (t, J=6 Hz).

Example 93

3-[5-(2,4-Dioxo-thiazolidin-5-ylidenemethyl)-benzofuran-3-yl]-propionic acid

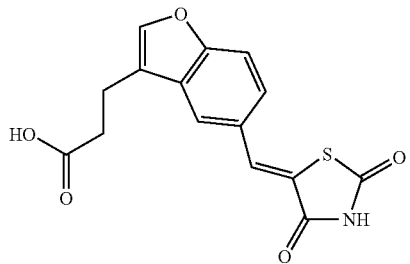

The title compound was obtained applying standard saponifications techniques as described for example 72 using example 92 as starting material.

HPLC: 3.09 min. LC-MS (10 min.): M/Z ESI: 1.19 min, 316.14 (M−1). $^1$H NMR: (DMSO-d6) δ 12.58 (br. s, 1H), 12.22 (b. s, 1H), 7.93 (d, J=12 Hz, 3H), 7.70 (d, J=9 Hz, 1H), 7.54 (d, J=9 Hz, 1H), 2.91 (t, J=9 Hz, 2H), 2.65 (t, 6 Hz, 2H).

Example 94

5-[3-(3-Oxo-3-piperidin-1-yl-propyl)-benzofuran-5-ylmethylene]-thiazolidine-2,4-dione

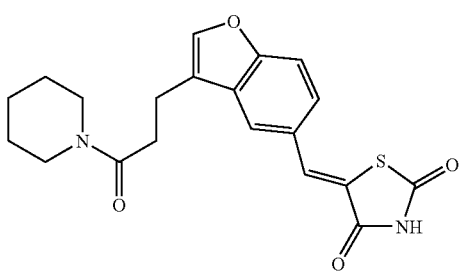

The title compound was obtained applying the synthetic protocol as described for example 73 using example 93 as starting material.

HPLC: 3.783 min. LC-MS: M/Z ESI: 1.46 min, 385.14 (M+1). $^1$H NMR: (DMSO-d6) δ 12.66 (br. s, 1H), 8.06 (s, 3H), 8.01 (s, 1H), 7.79 (s, 1H), 3.50-1.60 (m, 14H).

Example 95

6-(2,4-Dioxo-thiazolidin-5-ylidenemethyl)-2,3-dihydro-benzo[1,4]oxazine-4-carboxylic acid tert-butyl ester

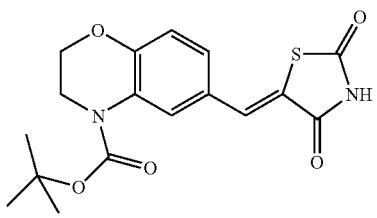

Following the general method as outlined in Example 1, starting from 6-Formyl-2,3-dihydro-benzo[1,4]oxazine-4-carboxylic acid tert-butyl ester (intermediate 62) and 1,3-thiazolidine-2,4-dione, the title compound was obtained.

HPLC: 2.52 min. LC-MS: M/Z ESI: min, 261.21 (M-Boc-1).

Example 96

5-(3,4-Dihydro-2H-benzo[1,4]oxazin-6-ylmethylene)-thiazolidine-2,4-dione

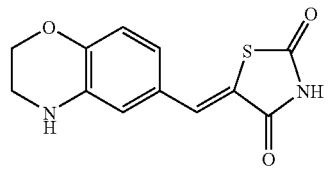

100 mg of 6-Formyl-2,3-dihydro-benzo[1,4]oxazine-4-carboxylic acid tert-butyl ester (intermediate 62) were treated with TFA/DCM 25% for 2 h. The solvents were evaporated to dryness and the remaining crude was used for the Knoevenagel reaction as outlined in Example 1 without further purification to obtain the title compound as yellow solid.

HPLC: 2.56 min. LC-MS: M/Z ESI: 1.14 min, 261.24 (M−1). $^1$H NMR: (DMSO-d6) δ 12.58 (br. s, 1H), 7.57 (s, 1H), 6.78 (s, 3H), 4.17 (t, J=3 Hz, 2H), 3.28 (t, J=6 Hz, 2H).

Example 97

5-(4-Benzoyl-3,4-dihydro-2H-benzo[1,4]oxazin-6-ylmethylene)-thiazolidine-2,4-dione

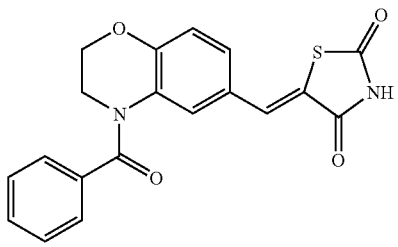

5-(3,4-Dihydro-2H-benzo[1,4]oxazin-6-ylmethylene)-thiazolidine-2,4-dione (example 96) (35 mg, 0.13 mmol) in 4 ml anhydrous THF were treated with benzoylchloride (156 uL, 10 eq.) in the presence of DIEA (2 eq.) for 3 h. Excess of benzoylchloride was hydrolysed, EtOAc was added and the organic phase was washed with NaHCO$_3$ and brine. The crude was purified on silica gel using EtOAc/cyclohexane 3:7 as eluent affording 14 mg (35%) of the title compound.

HPLC: 4.57 min. LC-MS: M/Z ESI: 2.11 min, 364.91 (M−1).

The following example was synthesized in the same way as described for example 97.

Example 98

5-(4-Acetyl-3,4-dihydro-2H-benzo[1,4]oxazin-6-ylmethylene)-thiazolidine-2,4-dione

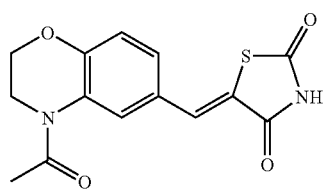

Yield=43 mg (95%)

HPLC: 2.65 min. LC-MS: M/Z ESI: 1.12 min, 305.24 (M+1). $^1$H NMR: (DMSO-d6) δ 12.58 (br. s, 1H), 8.30 (b s, 1H), 7.71 (s, 1H), 7.35 (d, J=9 Hz, 1H), 7.05 (d, J=9 Hz, 1H), 4.33 (t, J=6 Hz, 2H), 4.00 (t, J=6 Hz, 2H).

Example 99

6-(2,4-Dioxo-thiazolidin-5-ylidenemethyl)-benzo[1,4]oxazine-4-carboxylic acid tert-butyl ester

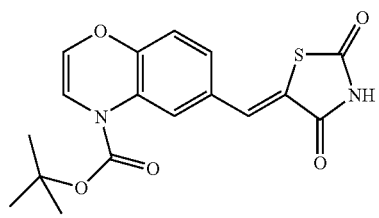

Following the general method as outlined in Example 1, starting from 6-Formyl-benzo[1,4]oxazine-4-carboxylic acid tert-butyl ester (intermediate 63) and 1,3-thiazolidine-2,4-dione, the title compound was obtained.

HPLC: 4.23 min. LC-MS: M/Z ESI: 1.82 min, 359.16 (M−1). $^1$H NMR: (DMSO-d6) δ 12.50 (br. s, 1H), 7.63 (d, J=3 Hz, 2H), 7.31 (d, J=3 Hz, 1H), 6.95 (d, J=6 Hz, 1H), 6.30 (s, 2H).

Example 100

[6-(2,4-Dioxo-thiazolidin-5-ylidenemethyl)-3-oxo-2,3-dihydro-benzo[1,4]-oxazin-4-yl]-acetic acid methyl ester

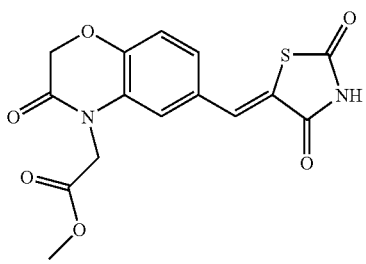

Following the general method as outlined in Example 1, starting from (6-Formyl-3-oxo-2,3-dihydro-benzo[1,4]oxazin-4-yl)-acetic acid methyl ester (intermediate 64) and 1,3-thiazolidine-2,4-dione, the title compound was obtained.

HPLC: 2.83 min. LC-MS: M/Z ESI: 1.20 min, 347.25 (M−1). $^1$H NMR: (DMSO-d6) δ 12.58 (br. s, 1H), 7.76 (s, 1H), 7.36 (s, 1H), 7.20 (m, 2H), 4.82 (d, J=15 Hz, 4H), 3.71 (s, 3H).

Example 101

N-Benzyl-2-[6-(2,4-dioxo-thiazolidin-5-ylidenemethyl)-3-oxo-2,3-dihydro-benzo[1,4]oxazin-4-yl]-acetamide

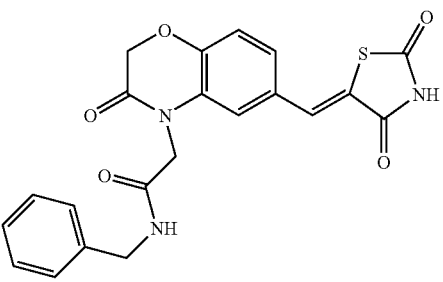

[6-(2,4-Dioxo-thiazolidin-5-ylidenemethyl)-3-oxo-2,3-dihydro-benzo[1,4]-oxazin-4-yl]-acetic acid methyl ester (195 mg, 0.56 mmol) (example 100) were saponified using 2 eq. of LiOH as described for example 74 affording [6-(2,4-Dioxo-thiazolidin-5-ylidenemethyl)-3-oxo-2,3-dihydro-benzo[1,4]oxazin-4-yl]-acetic acid. The so obtained acid (50 mg, 0.15 mmol) was dissolved in THF. HOBt (32 mg, 1.5 eq.), EDC (43 mg, 1.5 eq.) and benzylamine (25 mg, 1.5 eq.) were added while stirring. The reaction mixture was stirred for 15 h at rt. EtOAc was added and the organic phase was washed with 1N HCl, NaHCO$_3$, brine each of which three times. The crude residue after evaporating the solvents was purified on silica gel using DCM/EtOAc as eluents to give the title compound as colourless powder (35 mg, 54%).

HPLC: 3.06 min. LC-MS: M/Z ESI: 1.27 min, 424.21 (M+1).

Example 102

5-(4-Butyl-3-oxo-3,4-dihydro-2H-benzo[1,4]oxazin-6-ylmethylene)-thiazolidine-2,4-dione

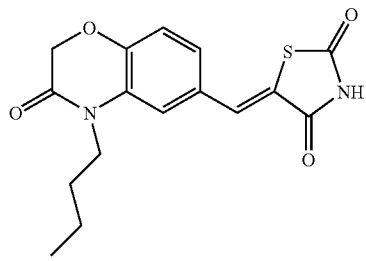

Following the general method as outlined in Example 1, starting from 4-Butyl-3-oxo-3,4-dihydro-2H-benzo[1,4]oxazine-6-carbaldehyde (intermediate 65) and 1,3-thiazolidine-2,4-dione, the title compound was obtained.

HPLC: 3.67 min. LC-MS: M/Z ESI: 1.49 min. 331.23 (M−1). $^1$H NMR: (DMSO-d6) δ 12.58 (br. s, 1H), 7.85 (s, 1H), 7.43 (s, 1H), 7.24 (d, J=6 Hz, 1H), 7.15 (d, J=9 Hz, 1H), 4.73 (s, 2H), 3.91 (t, J=3 Hz, 2H), 1.57, (m, 2H), 1.36 (m, 2H), 0.91 (t, J=9 Hz, 3H).

Example 103

5-(4-Benzyl-3-oxo-3,4-dihydro-2H-benzo[1,4]oxazin-6-ylmethylene)-thiazolidine-2,4-dione

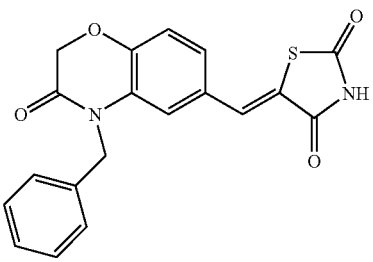

Following the general method as outlined in Example 1, starting from 4-Benzyl-3-oxo-3,4-dihydro-2H-benzo[1,4]oxazine-6-carbaldehyde (intermediate 66) and 1,3-thiazolidine-2,4-dione, the title compound was obtained.

HPLC: 3.67 min. LC-MS: M/Z ESI: 1.46 min, 365.17 (M−1). $^1$H NMR: (DMSO-d6) δ 12.58 (br. s, 1H), 7.68 (s, 1H), 7.38-7.22 (m, 8H), 5.24 (s, 2H), 4.97 (s, 2H).

Example 104

5-(2-Chloro-benzofuran-5-ylmethylene)-thiazolidine-2,4-dione

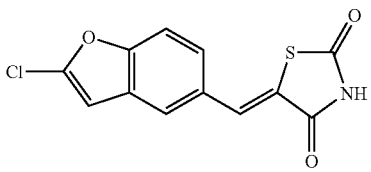

Following the general method as outlined in Example 1, starting from 2-Chloro-5-[1,3]dioxolan-2-yl-benzofurane (intermediate 67) and 1,3-thiazolidine-2,4-dione, the title compound was obtained.

HPLC: 3.84 min. LC-MS: M/Z ESI: 1.62 min, 278.12 (M−1). $^1$H NMR: (DMSO-d6) δ7.90-7.75 (M, 2H), 7.68 (d, j=9 Hz, 1H), 7.52 (d, J=9 Hz, 1H), 7.09 (s, 1H).

Example 105

5-(3-Amino-benzo[d]isoxazol-5-ylmethylene)-thiazolidine-2,4-dione

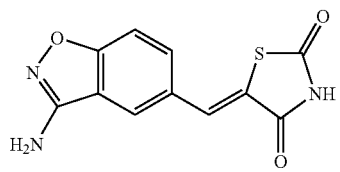

Following the general method as outlined in Example 1, starting from 3-Amino-benzo[d]isoxazole-5-carbaldehyde (intermediate 68) and 1,3-thiazolidine-2,4-dione, the title compound was obtained.

HPLC: 2.45 min. LC-MS: M/Z ESI: 0.97 min, 260.17 (M−1). $^1$H NMR: (DMSO-d6) δ 12.60 (br. s, 1H), 8.01 (s, 1H), 7.85 (s, 1H), 7.60 (d, J=9 Hz, 1H), 6.67 (s, 1H).

Example 106

5-(3-Phenylethynyl-benzofuran-5-ylmethylene)-thiazolidine-2,4-dione

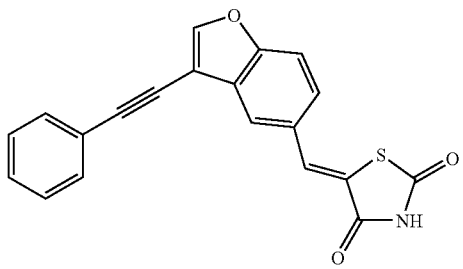

Following the general method as outlined in Example 1, starting from 3-Phenylethynyl-benzofuran-5-carbaldehyde (intermediate 59) and 1,3-thiazolidine-2,4-dione, the title compound was obtained.

HPLC: 4.82 min. LC-MS: M/Z ESI: 2.02 min, 344.18 (M−1). $^1$H NMR: (DMSO-d6) δ 12.58 (br. s, 1H), 8.49 (s, 1H), 7.92 (s, 1H), 7.72 (d, J=9 Hz, 1H), 7.62 (m, 3H), 7.45 (m, 4H).

Example 107

5-Benzo[1,2,5]thiadiazol-5-ylmethylene-thiazolidine-2,4-ione

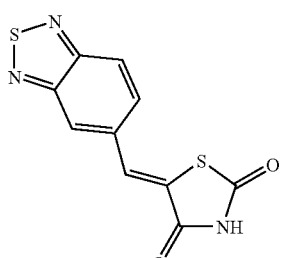

Following the general method as outlined in Example 1, starting from 2,1,3-Benzothiadiazole-5-carbaldehyde and 1,3-thiazolidine-2,4-dione, the title compound was obtained.

HPLC: 3.03 min. LC-MS: M/Z ESI: 1.14 min, 262.11 (M−1). $^1$H NMR: (DMSO-d6) δ 12.58 (br. s, 1H), 8.11 (m, 2H), 7.90 (d, J=9 Hz, 1H), 7.47 (s, 1H).

Example 108

5-Benzo[1,2,5]oxadiazol-5-ylmethylene-thiazolidine-2,4-ione

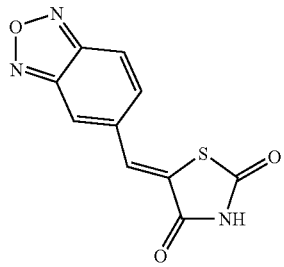

Following the general method as outlined in Example 1, starting from 2,1,3-Benzoxadiazole-5-carbaldehyde and 1,3-thiazolidine-2,4-dione, the title compound was obtained.

HPLC: 3.02 min. LC-MS: M/Z ESI: 1.17 min, 246.17 (M−1). $^1$H NMR: (DMSO-d6) δ 12.58 (br. s, 1H), 8.07 (m, 2H), 7.82 (d, J=9 Hz, 1H), 7.40 (s, 1H).

Example 109

5-(2-Methyl-benzofuran-6-ylmethylene)-thiazolidine-2,4-dione

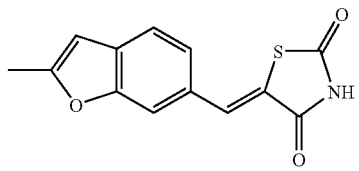

Following the general method as outlined in Example 1, starting from 2-Methyl-5-[1,3]dioxolan-2-yl-benzofuran (intermediate 72) and 1,3-thiazolidine-2,4-dione, the title compound was obtained after purification on reverse phase HPLC (solvents gradient H$_2$O/CH$_3$CN 0.1% TFA).

HPLC: 3.65 min, 90.75%. LC-MS: M/Z ESI: 1.65 min, 258.21 (M−1). $^1$H NMR: (DMSO-d6) δ 12.45 (s1, 1H), 7.88 (s, 1H), 7.77 (d, 1H, J=1.5 Hz), 7.64 (d, 1H, J=8.6 Hz), 7.47 (dd, 1H, J=8.6, 1.5 Hz), 6.69 (s, 1H), 2.37 (s, 3H).

Example 110

5-(2-Carboxymethyl-benzofuran-6-ylmethylene)-thiazolidine-2,4-dione

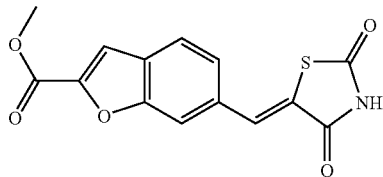

Following the general method as outlined in Example 1, starting from 5-[1,3]Dioxolan-2-yl-benzofuran-2-carboxylic acid methyl ester (intermediate 73) and 1,3-thiazolidine-2,4-dione, the title compound was obtained after purification on reverse phase HPLC (solvents gradient H$_2$O/CH$_3$CN 0.1% TFA).

HPLC: 3.32 min, 92.06%. LC-MS: M/Z ESI: 1.51 min, 302.19 (M−1). $^1$H NMR: (DMSO-d6) δ 12.52 (s1, 1H), 7.97 (d, 1H, J=1.5 Hz), 7.82 (m, 3H), 7.69 (dd, 1H, J=8.6, 1.5 Hz), 3.90 (s, 3H).

Example 111

5-(3-Bromo-2-fluoro-2,3-dihydro-benzofuran-6-ylmethylene)-thiazolidine-2,4-dione

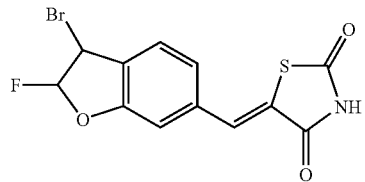

Following the general method as outlined in Example 1, starting from 3-Bromo-2-fluoro-benzofuran-5-carbaldehyde (intermediate 74) and 1,3-thiazolidine-2,4-dione, the title compound was obtained after purification on reverse phase HPLC (solvents gradient H$_2$O/CH$_3$CN 0.1% TFA).

HPLC: 3.66 min, 92.37%. LC-MS: M/Z ESI: 1.56 min, 343.09 (M−1). $^1$H NMR: (DMSO-d6) δ 12.82 (s1, 1H), 8.00 (d, 1H, J=1.8 Hz), 7.88 (dd, 1H, J=8.5, 1.8 Hz), 7.55 (d, 1H, J=8.5 Hz), 7.03 (d, 1H, $^2J_{H\text{-}F}$=59.5 Hz), 6.20 (d, 1H, $^3J_{H\text{-}F}$=15.3 Hz). $^{19}$F NMR: (DMSO-d6) δ-114.66.

Example 112

5-(2-Fluoro-benzofuran-6-ylmethylene)-thiazolidine-2,4-dione

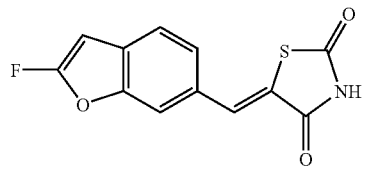

Following the general method as outlined in Example 1, starting from 2-Fluoro-5-[1,3]dioxolan-2-yl-benzofuran (intermediate 75) and 1,3-thiazolidine-2,4-dione, the title compound was obtained after purification on reverse phase HPLC (solvents gradient H$_2$O/CH$_3$CN 0.1% TFA).

HPLC: 3.67 min, 99.47%. LC-MS: M/Z ESI: 1.51 min, 262.14 (M−1). $^1$H NMR: (DMSO-d6) δ 12.04 (s1, 1H), 7.89 (d, 1H, J=1.5 Hz), 7.83 (d, 1H, J=1.5 Hz), 7.73 (d, 1H, J=8.6 Hz), 7.55 (dd, 1H, J=8.6, 1.5 Hz), 6.47 (d, 1H, $^3J_{H\text{-}F}$=6.4 Hz). $^{19}$F NMR: (DMSO-d6) δ-111.28, −112.18.

Example 113

Preparation of a Pharmaceutical Formulation

The following formulation examples illustrate representative pharmaceutical compositions according to the present invention being not restricted thereto.

Formulation 1—Tablets

A compound of formula (I) is admixed as a dry powder with a dry gelatin binder in an approximate 1:2 weight ration. A minor amount of magnesium stearate is added as a lubricant. The mixture is formed into 240-270 mg tablets (80-90 mg) of active azolidinone compound per tablet) in a tablet press.

Formulation 2—Capsules

A compound of formula (I) is admixed as a dry powder with a starch diluent in an approximate 1:1 weight ratio. The mixture is filled into 250 mg capsules (125 mg of active azolidinone compound per capsule).

Formulation 3—Liquid

A compound of formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active azolidinone compound) in a tablet press.

Formulation 5—Injection

A compound of formula (I) is dissolved in a buffered sterile saline injectable aqueous medium to a concentration of approximately 5 mg/ml.

Example 114

Biological Assays

The compounds of the present invention may be subjected to the following assays:

a) High Throughput PI3K Lipid Kinase Assay (Binding Assay):

The assay combines the scintillation proximity assay technology (SPA, Amersham) with the capacity of neomycin (a polycationic antibiotic) to bind phospholipids with high affinity and specificity. The Scintillation Proximity Assay is based on the properties of weakly emitting isotopes (such as $^3$H, $^{125}$I, $^{33}$P). Coating SPA beads with neomycin allows the detection of phosphorylated lipid substrates after incubation with recombinant PI3K and radioactive ATP in the same well, by capturing the radioactive phospholipids to the SPA beads through their specific binding to neomycin.

To a 384 wells MTP containing 5 µl of the test compound of formula (I) (solubilized in 6% DMSO; to yield a concentration of 100, 30, 10, 3, 1, 0.3, 0.1, 0.03, 0.01, 0.001 µM of the test compound), the following assay components are added. 1) 5 µl (58 ng) of Human recombinant GST-PI3Kγ (in Hepes 40 mM, pH 7.4, DTT 1 mM and ethyleneglycol 5%) 2) 10 µl of lipid micelles and 3) 10 µl of Kinase buffer ([$^{33}$P]γATP 45 µM/60 nCi, MgCl$_2$ 30 mM, DTT 1 mM, β-Glycerophosphate 1 mM, Na$_3$VO$_4$ 100 µM, Na Cholate 0.3%, in Hepes 40 mM, pH 7.4). After incubation at room temperature for 180 minutes, with gentle agitation, the reaction is stopped by addition of 60 µl of a solution containing 100 µg of neomycin-coated PVT SPA beads in PBS containing ATP 10 mM and EDTA 5 mM. The assay is further incubated at room temperature for 60 minutes with gentle agitation to allow binding of phospholipids to neomycin-SPA beads. After precipitation of the neomycin-coated PVT SPA beads for 5 minutes at 1500×g, radioactive PtdIns(3)P is quantified by scintillation counting in a Wallac MicroBeta™ plate counter.

The values indicated in respect of PI3Kγ refer to the IC$_{50}$ (µM), i.e. the amount necessary to achieve 50% inhibition of said target. Said values show a considerable potency of the azolidinone-vinyl fused-benzene compounds with regard to PI3Kγ.

The tested compounds according to formula (I) display an inhibition (IC$_{50}$) with regard to PI3Kγ of less than 2 µM, more preferred equal or less than 1 µM.

Examples of inhibitory activities for test compounds 41, 61, 66, 73, 103, 107 and 110 as set out in Table 1.

TABLE 1

IC$_{50}$ values of azolidinone-vinyl fused-benzene derivatives against PI3Kγ.

| Example No | PI3Kγ, IC$_{50}$ (µM) |
|---|---|
| 41 | <1 |
| 61 | <1 |
| 66 | <1 |
| 73 | <1 |
| 103 | <1 |
| 107 | <1 |
| 110 | <1 | b) Cell Based ELISA to Monitor PI3K Inhibition:

Measurement of Akt/PKB phosphorylation in macrophages after stimulation with C5a: Raw 264: Raw 264-7 macrophages (cultured in DMEM-F12 medium containing 10% Fetal Calf serum and antibiotics) are plated at 20'000 cells/well in a 96 MTP 24 h before cell stimulation. Previous to the stimulation with 50 nM of Complement 5a (C5a; which is a well known chemokine which stimulates the used cells) during 5 minutes, Cells are serum starved for 2 h, and pretreated with inhibitors for 20 minutes. After stimulation cells are fixed in 4% formaldehyde for 20 minutes and washed 3 times in PBS containing 1% Triton X-100 (PBS/Triton). Endogenous peroxidase is blocked by a 20 minutes incubation in 0.6% H$_2$O$_2$ and 0.1% Sodium Azide in PBS/Triton and washed 3 times in PBS/Triton. Cells are then blocked by 60 minutes incubation with 10% fetal calf serum in PBS/Triton. Next, phosphorylated Atk/PKB is detected by an overnight incubation at 4° C. with first antibody (anti phospho Serine 473 Akt 1HC, Cell Signaling) diluted 800-fold in PBS/Triton, containing 5% bovine serum albumin (BSA). After 3 washes in PBS/Triton, cells are incubated for 60 minutes with a peroxidase conjugated goat-anti-rabbit antibody (1/400 dilution in PBS/Triton, containing 5% BSA), washed 3 times in PBS/Triton, and 2 times in PBS and further incubated in 100 µl of substrate reagent solution (R&D) for 20 minutes.

The reaction is stopped by addition of 50 µl of 1 M H$_2$SO$_4$ and absorbance is read at 450 nm.

The values indicated reflect the percentage of inhibition of AKT phosphorylation as compared to basal level. Said values show a clear effect of the azolidinone-vinyl fused-benzene compounds on the activation of AKT phosphorylation in macrophages.

Compounds of examples 1, 19, 66 and 107, when used at 1 μM completely (about 100%) inhibit C5a-mediated AKT phosphorylation. Examples 17, 19 or 73, when used at 1 μM, inhibit 95% of the C5a-mediated AKT-phosphorylation.

The invention claimed is:

1. A method for the treatment of inflammation, the method comprising, administering to a subject in need thereof, an effective amount of a compound of formula (I):

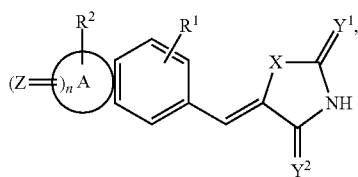

(I)

as well as its geometrical isomers, its optically active forms as enantiomers, diastereomers and its racemate forms, as well as pharmaceutically acceptable salts thereof, wherein A is a 5-8 membered heterocyclic group;
X is S or O;
$Y^1$ and $Y^2$ are independently S or O;
Z is S or O;
R' is H, CN, carboxy, acyl, $C_1$-$C_6$-alkoxy, halogen, hydroxy, acyloxy, $C_1$-$C_6$-alkyl carboxy, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, acylamino, $C_1$$C_6$-alkyl acylamino, ureido, $C_1$-$C_6$-alkyl ureido, amino, $C_1$-$C_6$-alkyl amino, ammonium, sulfonyloxy, $C_1$-$C_6$-alkyl sulfonyloxy, sulfonyl, $C_1$-$C_6$-alkyl sulfonyl, sulfinyl, $C_1$-$C_6$-alkyl sulfinyl, sulfanyl, $C_1$-$C_6$-alkyl sulfanyl, sulfonylamino, $C_1$-$C_6$-alkyl sulfonylamino or carbamate;
$R^2$ is selected from the group consisting of H, halogen, acyl, amino, $C_1$-$C_6$-alkyl, $C_2$-$C_6$-alkenyl, $C_2$-$C_6$-alkynyl, $C_1$-$C_6$-alkyl carboxy, $C_1$-$C_6$-alkyl acyl, $C_1$-$C_6$-alkyl alkoxycarbonyl, $C_1$-$C_6$-alkyl aminocarbonyl, $C_1$-$C_6$-alkyl acyloxy, $C_1$-$C_6$-alkyl acylamino, $C_1$-$C_6$-alkyl ureido, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, $C_3$-$C_8$-cycloalkyl or heterocycloalkyl, $C_1$-$C_6$-alkyl aryl, $C_2$-$C_6$-alkenyl-aryl, $C_2$-$C_6$-alkynyl aryl, carboxy, cyano, hydroxy, $C_1$-$C_6$-alkoxy, nitro, acylamino, ureido, $C_1$-$C_6$-alkyl carbamate, sulfonylamino, sulfanyl, or sulfonyl;
n is 0, 1 or 2;
with the proviso that the following compounds are excluded:

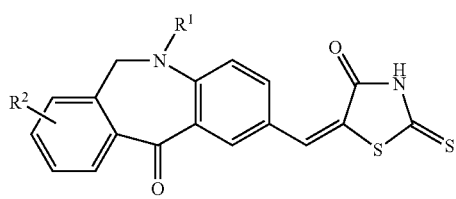

(TE)

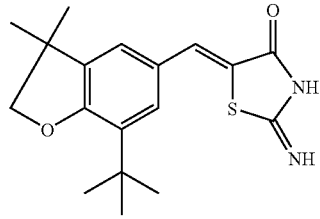

(JA)

wherein $R^1$ is a lower alkyl or aralkyl and $R^2$ is H or a halogen.

2. The method according to claim 1, wherein $Y^1$ and $Y^2$ are both oxygen.

3. The method according to claim 1, wherein n is 1 or 2 and $R^1$ and $R^2$ are both H.

4. The method according to claim 1, wherein, in the compound of formula (I), X is S, $Y^1$ and $Y^2$ are both O, and n is 0.

5. The method according to claim 1, whereby the compound of formula (I) is a thiazolidinone-vinyl fused-benzene of the formula (Ia)

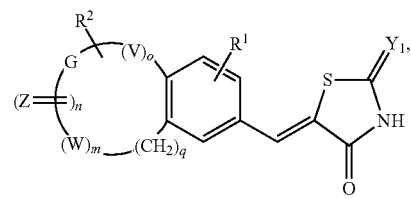

(Ia)

wherein $Y^1$, $R^1$, $R^2$, Z and n are as above defined for the compound of formula (I);
V and W are each, independently from each other, O, S or —$NR^3$ wherein $R^3$ is H or $C_1$-$C_6$ alkyl;
G is a $C_1$-$C_5$ alkylene or a $C_1$-$C_5$ alkenylene group;
o and m are each, independently from each other, 0 or 1; and
q is an integer from 0 to 4.

6. The method according to claim 5, whereby the thiazolidinone-vinyl fused-benzene has the formula (Ib):

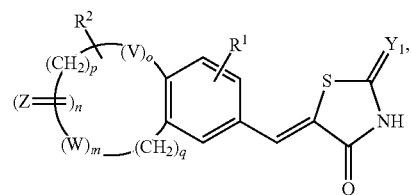

(Ib)

wherein $Y^1$, $R^1$, $R^2$, V, Z, W, m, n, o, q are as above defined in the compound of formula (Ia), and p is an integer from 1 to 4.

7. The method according to claim 5, whereby the thiazolidinone-vinyl fused-benzene has the formula (Ic):

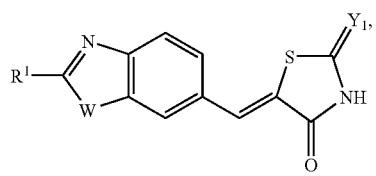

(Ic)

wherein W, as well as $R^1$ and $Y^1$, are as above defined in the compound of formula (Ia).

8. The method according to claim 5, whereby the thiazolidinone-vinyl fused-benzene has the formula (Id):

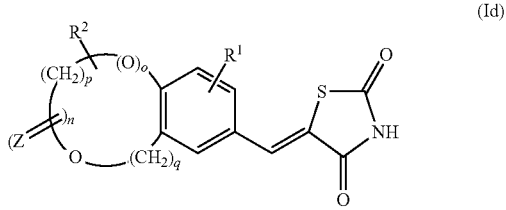

(Id)

wherein $R^1$, $R^2$, Z and n are as above defined in formula (Ia); o is 0 or 1;

p is an integer from 1 to 4 and q is an integer from 0 to 4.

9. The method according to claim 5, wherein, in formula (Ia), Z is O, m is 0, n is 1, p is 1 or 2, q is 1, and $R^1$ and $R^2$ are each as above defined for the compound of formula (Ia).

10. The method according to claim 5, wherein, in formula (Ia), m is 1, n is 0, p is 1 or 2, q is 0, and $R^1$ and $R^2$ are each as above defined for the compound of formula (Ia).

11. The method according to claim 5, wherein, in formula (Ia), m is 0, n is 1, p is 1 or 2, q is 0, and $R^1$ and $R^2$ are each as defined above for the compound of formula (I).

12. The method according to claim 5, wherein, in formula (Ia), $R^1$ is halogen or hydrogen.

13. A thiazolidinone-vinyl fused-benzene according to formula (II-a):

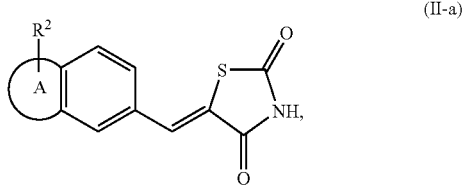

(II-a)

wherein A is selected from the group consisting of dioxol, dioxin, dihydrofuran, (dihydro) furanyl, (dihydro)oxazinyl, pyridinyl, isooxazolyl, oxazolyl (dihydro) napthalenyl, pyrimidinyl, triazolyl, imidazolyl, pyrazinyl, thiazolidinyl, thiadiazolyl, and oxadiazolyl;

$R^2$ is selected from the group consisting of H, halogen, acyl, amino, $C_1$-$C_6$-alkyl, $C_2$-$C_6$-alkenyl, $C_2$-$C_6$-alkenyl, $C_1$-$C_6$-alkyl carboxy, $C_1$-$C_o$-alkyl acyl, $C_1$-$C_6$-alkyl alkoxycarbonyl, $C_1$-$C_6$-alkyl aminocarbonyl, $C_1$-$C_o$-alkyl acyloxy, $C_1$-$C_6$-alkyl acylamino, $C_1$-$C_6$-alkyl ureido, $C_1$-$C_6$-alkyl carbamate, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, $C_3$-$C_8$-cycloalkyl or heterocycloalkyl, $C_1$-$C_6$-alkyl aryl, $C_2$-$C_6$-alkenyl-aryl, $C_2$-$C_6$-alkynyl aryl, carboxy, cyano, hydroxy, $C_1$-$C_6$-alkoxy, nitro, acylamino, ureido, sulfonylamino, sulfanyl, and sulfonyl.

14. A thiazolidinone-vinyl fused-benzene according to formula (II):

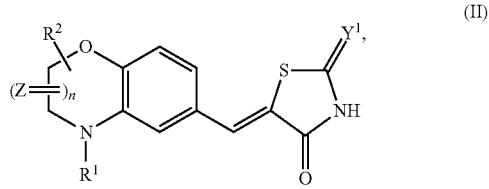

(II)

as well as its geometrical isomers, its optically active forms as enantiomers, diastereomers and its racemate forms, as well as pharmaceutically acceptable salts thereof, wherein $Y^1$ is S or O;

Z is S or O;

$R^1$ is H, CN, carboxy, acyl, $C_1$-$C_6$-alkoxy, halogen, hydroxy, acyloxy, $C_1$-$C_6$-alkyl carboxy, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, acylamino, $C_1$-$C_6$-alkyl acylamino, ureido, $C_1$-$C_6$-alkyl ureido, amino, $C_1$-$C_6$-alkyl amino, ammonium, sulfonyloxy, $C_1$-$C_6$-alkyl sulfonyloxy, sulfonyl, $C_1$-$C_6$-alkyl sulfonyl, sulfinyl, $C_1$-$C_6$-alkyl sulfinyl, sulfanyl, $C_1$-$C_6$-alkyl sulfanyl, sulfonylamino, $C_1$-$C_6$-alkyl sulfonylamino or carbamate;

$R^2$ is selected from the group consisting of H, halogen, acyl, amino, $C_1$-$C_6$-alkyl, $C_2$-$C_6$-alkenyl, $C_2$-$C_6$-alkynyl, $C_1$-$C_6$-alkyl carboxy, $C_1$-$C_6$-alkyl acyl, $C_1$-$C_6$-alkyl alkoxycarbonyl, $C_1$-$C_6$-alkyl aminocarbonyl, $C_1$-$C_6$-alkyl acyloxy, $C_1$-$C_6$-alkyl acylamino, $C_1$-$C_6$-alkyl ureido, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, $C_3$-$C_8$-cycloalkyl or heterocycloalkyl, $C_1$-$C_6$-alkyl aryl, $C_2$-$C_6$-alkenyl-aryl, $C_2$-$C_6$-alkynyl aryl, carboxy, cyano, hydroxy, $C_1$-$C_6$-alkoxy, nitro, acylamino, ureido, $C_1$-$C_6$-alkyl carbamate, sulfonylamino, sulfanyl, and sulfonyl;

n is 0 or 1.

15. The thiazolidinone-vinyl fused-benzene according to claim 14, wherein $Y^1$ is O.

16. The thiazolidinone-vinyl fused-benzene according to claim 14, wherein $R^1$ is selected from the group consisting of $C_1$-$C_6$-alkyl, $C_1$-$C_6$-alkyl aryl, aryl, $C_3$-$C_8$-cycloalkyl or heterocycloalkyl, $C_1$-$C_6$-alkyl aryl, $C_2$-$C_6$-alkenyl-aryl and $C_2$-$C_6$-alkynyl aryl.

17. A thiazolidinone-vinyl fused-benzene according to formula (III):

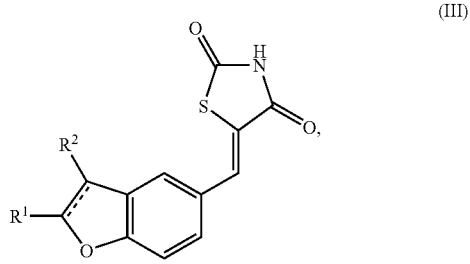

(III)

as well as its geometrical isomers, its optically active forms as enantiomers, diastereomers and its racemate forms, as well as pharmaceutically acceptable salts thereof, and wherein $R^1$ is H, CN, carboxy, acyl, $C_1$-$C_6$-alkoxy, halogen, hydroxy, acyloxy, $C_1$-$C_6$-alkyl carboxy, $C_1$-$C_6$-alkyl acyloxy, $C_1$-$C_6$-alkyl alkoxy, alkoxycarbonyl, $C_1$-$C_6$-alkyl alkoxycarbonyl, aminocarbonyl, $C_1$-$C_6$-alkyl aminocarbonyl, acyloxy, $C_1$-$C_6$-alkyl acylamino, ureido, $C_1$-$C_6$-alkyl ureido, amino, $C_1$-$C_6$-alkyl amino, ammonium, sulfonyloxy, $C_1$-$C_6$-alkyl sulfonyloxy, sulfonyl, $C_1$-$C_6$-alkyl sulfonyl, sulfinyl, $C_1$-$C_6$-alkyl sulfinyl, sulfanyl, $C_1$-$C_6$-alkyl sulfanyl, sulfonylamino, $C_1$-$C_6$-alkyl sulfonylamino or carbamate;

$R^2$ is selected from the group consisting of H, halogen, acyl, amino, $C_1$-$C_6$-alkyl, $C_2$-$C_o$-alkenyl, $C_2$-$C_6$-alkynyl, $C_1$-$C_o$-alkyl carboxy, $C_1$-$C_6$-alkyl acyl, $C_1$-$C_6$-alkyl alkoxycarbonyl, $C_1$-$C_6$-alkyl aminocarbonyl, acyloxy, $C_1$-$C_6$-alkyl acylamino, $C_1$-$C_6$-alkyl ureido, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, $C_3$-$C_8$-cycloalkyl or heterocycloalkyl, $C_1$-$C_6$-alkyl aryl, $C_2$-$C_6$-alkenyl-aryl, $C_2$-$C_6$-alkynyl aryl, carboxy, cyano, hydroxy, $C_1$-$C_6$-alkoxy, nitro, acylamino, ureido, $C_1$-$C_6$-alkyl carbamate, sulfonylamino, sulfanyl, and sulfonyl.

18. A thiazolidinone-vinyl fused-benzene according any of formulae (IV), (V) and (VI):

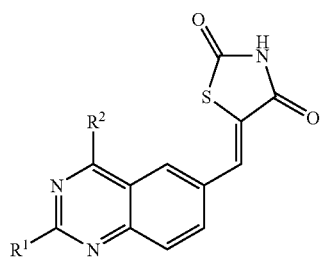

(IV)

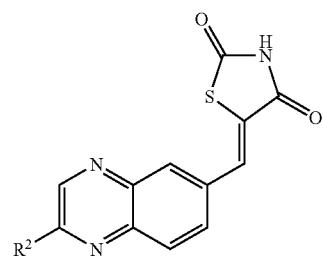

(V)

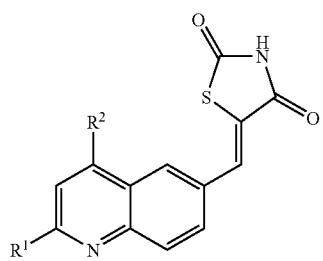

(VI)

wherein $R^1$ is selected from the group consisting of hydrogen, halogen, cyano, $C_1$-$C_6$-alkyl, $C_1$-$C_6$-alkoxy, acyl, and alkoxy cabonyl, and $R^2$ is selected from the group consisting of H, halogen, acyl, amino, $C_1$-$C_6$-alkyl, $C_2$-$C_6$-alkenyl, $C_2$-$C_6$-alkynyl, $C_1$-$C_6$-alkyl carboxy, $C_1$-$C_6$-alkyl acyl, $C_1$-$C_6$-alkyl alkoxycarbonyl, $C_1$-$C_6$-alkyl aminocarbonyl, $C_1$-$C_6$-alkyl acyloxy, $C_1$-$C_6$-alkyl acylamino, $C_1$-$C_6$-alkyl ureido, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, $C_3$-$C_8$-cycloalkyl or heterocycloalkyl, $C_1$-$C_6$-alkyl aryl, $C_2$-$C_6$-alkenyl-aryl, $C_2$-$C_6$-alkynyl aryl, carboxy, cyano, hydroxy, $C_1$-$C_6$-alkoxy, nitro, acylamino, ureido, $C_1$-$C_6$-alkyl carbamate, sulfonylamino, sulfanyl, and sulfonyl.

19. The thiazolidinone-vinyl fused-benzene according to claim 13, selected from the group consisting of:
- 5-(1,3-benzodioxol-5-ylmethylene)-1,3-thiazolidine-2,4-dione,
- 5-(1,3-benzodioxol-5-ylmethylene)-2-thioxo-1,3-thiazolidin-4-one,
- 5-(2,3-dihydro-1,4-benzodioxin-6-ylmethylene)-1,3-thiazolidine-2,4-dione,
- 5-(2,3-dihydro-1-benzofuran-5-ylmethylene)-1,3-thiazolidine-2,4-dione,
- 5-[(7-methoxy-1,3-benzodioxol-5-yl)methylene]-1,3-thiazolidine-2,4-dione,
- 5-[(9,10-dioxo-9,10-dihydroanthracen-2-yl)methylene]-1,3-thiazolidine-2,4-dione,
- (5-[(2,2-difluoro-1,3-benzodioxol-5-yl)methylene]-1,3-thiazolidine-2,4-dione,
- (5Z)-5-(1,3-dihydro-2-benzofuran-5-ylmethylene)-1,3-thiazolidine-2,4-dione,
- 5-(1-benzofuran-5-ylmethylene)-1,3-thiazolidine-2,4-dione,
- 5-[(4-methyl-3-oxo-3,4-dihydro-2H-1,4-benzoxazin-6-yl)methylene]-1,3-thiazolidine-2,4-dione,
- 5-(1,3-benzodioxol-5-ylmethylene)-2-imino-1,3-thiazolidin-4-one,
- 5-Quinolin-6-ylmethylene-thiazolidine-2,4-dione,
- 5-Quinolin-6-ylmethylene-2-thioxo-thiazolidin-4-one,
- 2-Imino-5-quinolin-6-ylmethylene-thiazolidin-4-one,
- 5-(3-Methyl-benzo[d]isoxazol-5-ylmethylene)-thiazolidine-2,4-dione,
- 5-(4-Phenyl-quinazolin-6-ylmethylene)-thiazolidine-2,4-dione,
- 5-(4-Dimethylamino-quinazolin-6-ylmethylene)-thiazolidine-2,4-dione,
- 5-[(4-aminoquinazolin-6-yl)methylene]-1,3-thiazolidine-2,4-dione,
- 5-[(4-piperidin-1-ylquinazolin-6-yl)methylene]-1,3-thiazolidine-2,4-dione,
- 5-[(4-morpholin-4-ylquinazolin-6-yl)methylene]-1,3-thiazolidine-2,4-dione,
- 5-{[4-(benzylamino)quinazolin-6-yl]methylene}-1,3-thiazolidine-2,4-dione,
- 5-{[4-(diethylamino)quinazolin-6-yl]methylene)-1,3-thiazolidine-2,4-dione,
- 5-({4-[(pyridin-2-ylmethyl)amino]quinazolin-6-yl}methylene)-1,3-thiazolidine-2,4-dione,
- 5-({4-[(pyridin-3-ylmethyl)amino]quinazolin-6-yl}methylene)-1,3-thiazolidine-2,4-dione,
- ethyl 1-{6-[(2,4-dioxo-1,3-thiazolidin-5-ylidene)methyl]quinazolin-4-yl}piperidine-3-carboxylate,
- ethyl 1-{6-[(2,4-dioxo-1,3-thiazolidin-5-ylidene)methyl]quinazolin-4-yl)piperidine-4-carboxylate,
- tert-butyl-1-{6-[(2,4-dioxo-1,3-thiazolidin-5-ylidene)methyl]quinazolin-4-yl)-L-prolinate,
- 5-{[4-(4-methylpiperazin-1-yl)quinazolin-6-yl]methylene}-1,3-thiazolidine-2,4-dione,
- 5-{[4-(4-pyrimidin-2-ylpiperazin-1-yl)quinazolin-6-yl]methylene}-1,3-thiazolidine-2,4-dione,
- 5-({4-[4-(4-fluorophenyl)piperidin-1-yl]quinazolin-6-yl}methylene)-1,3-thiazolidine-2,4-dione, 5-{[4-(4-benzylpiperidin-1-yl)quinazolin-6-yl]methylene}-1,3-thiazolidine-2,4-dione,
5-({4-[4-(2-phenylethyl)piperidin-1-yl]]quinazolin-6-yl}methylene)-1,3-thiazolidine-2,4-dione,
5-{[4-(4-methylpiperidin-1-yl)quinazolin-6-yl]methylene}-1,3-thiazolidine-2,4-dione,
5-{[4-(4-hydroxypiperidin-1-yl)quinazolin-6-yl]methylene}-1,3-thiazolidine-2,4-dione,
1-[6-(2,4-Dioxo-thiazolidin-5-ylidenemethyl)-quinazolin-4-yl]-piperidine-4-carboxylic acid,
1-[6-(2,4-Dioxo-thiazolidin-5-ylidenemethyl)-quinazolin-4-yl]-piperidine-3-carboxylic acid,
1-[6-(2,4-Dioxo-thiazolidin-5-ylidenemethyl)-quinazolin-4-yl]-pyrrolidine-2-carboxylic acid,
5-(4-Methylamino-quinazolin-6-ylmethylene)-thiazolidine-2,4-dione,
5-(4-Methoxy-quinazolin-6-ylmethylene)-thiazolidine-2,4-dione
2-Imino-5-(4-methylamino-quinazolin-6-ylmethylene)-thiazolidin-4-one,
2-Imino-5-(4-piperidine-quinazolin-6-ylmethylene)-thiazolidin-4-one,
2-Imino-5-(4-dimethylamino-quinazolin-6-ylmethylene)-thiazolidin-4-one,
5-(2-Methyl-2H-benzotriazol-5-ylmethylene)-thiazolidine-2,4-dione,
5-(3-Methyl-3H-benzotriazol-5-ylmethylene)-thiazolidine-2,4-dione,
5-(3-Ethyl-3H-benzoimidazol-5-ylmethylene)-thiazolidine-2,4-dione,
5-{[1-(4-phenylbutyl)-1H-benzimidazol-6-yl]methylene}-1,3-thiazolidine-2,4-dione,
5-[(1-prop-2-yn-1-yl-H-benzimidazol-6-yl)methylene]-1,3-thiazolidine-2,4-dione,
5-[(1-{2-[4-(trifluoromethyl)phenyl]ethyl}-1H-benzimidazol-6-yl)methylene]-1,3-thiazolidine-2,4-dione,
5-([1-{2-(4-hydroxyphenyl)ethyl]-1H-benzimidazol-6-yl}methylene)-1,3-thiazolidine-2,4-dione,
methyl 4-{6-[(2,4-dioxo-1,3-thiazolidin-5-ylidene)methyl]-1H-benzimidazol-1-yl}cyclohexanecarboxylate,
5-({1-[2-(5-methoxy-1H-indol-3-yl)ethyl]-1H-benzimidazol-6-yl}methylene)-1,3-thiazolidine-2,4-dione,
5-({1-[(1-methyl-1H-pyrazol-4-yl)methyl]-1H-benzimidazol-6-yl}methylene)-1,3-thiazolidine-2,4-dione,
5-({1-[2-(3,4-dimethoxyphenyl)ethyl]-1H-benzimidazol-6-yl}methylene)-1,3-thiazolidine-2,4-dione,
5-({1-[2-(4-phenoxyphenyl)ethyl]-1H-benzimidazol-6-yl}methylene)-1,3-thiazolidine-2,4-dione,
5-({1-[4-(trifluoromethyl)benzyl]-1H-benzimidazol-6-yl}methylene)-1,3-thiazolidine-2,4-dione,
4-{6-[(2,4-dioxo-1,3-thiazolidin-5-ylidene)methyl]-1H-benzimidazol-1-yl}cyclohexanecarboxylic acid,
5-[(1-isobutyl-1H-benzimidazol-6-yl)methylene]-1,3-thiazolidine-2,4-dione,
5-({1-[2-(1,3-benzodioxol-4-yl)ethyl]-1H-benzimidazol-6-yl}methylene)-1,3-thiazolidine-2,4-dione,
5-({1-[2-(2-phenoxyphenyl)ethyl]-1H-benzimidazol-6-yl}methylene)-1,3-thiazolidine-2,4-dione,
5-{[1-(3,3-diphenylpropyl)-1H-benzimidazol-6-yl]methylene}-1,3-thiazolidine-2,4-dione,
5-{[1-(2-methoxybenzyl)-1H-benzimidazol-6-yl]methylene}-1,3-thiazolidine-2,4-dione,
5-{[1-(3-furylmethyl)-1H-benzimidazol-6-yl]methylene}-1,3-thiazolidine-2,4-dione,
5-[(1-propyl-1H-benzimidazol-6-yl)methylene]-1,3-thiazolidine-2,4-dione,
5-Quinoxalin-6-ylmethylene-thiazolidine-2,4-dione,
5-Quinoxalin-6-ylmethylene-2-thioxo-thiazolidin-4-one,
2-Imino-5-quinoxalin-6-ylmethylene-thiazolidin-4-one,
5-Benzothiazol-6-ylmethylene-thiazolidine-2,4-dione,
5-(3-Methyl-benzofuran-5-ylmethylene)-thiazolidine-2,4-dione,
5-(2-Bromo-3-methyl-benzofuran-5-ylmethylene)-thiazolidine-2,4-dione,
5-(3-bromo-benzofuran-5-ylmethylene)-thiazolidine-2,4-dione,
3-[5-(2,4-Dioxo-thiazolidin-5-ylidenemethyl)-benzofuran-3-yl]-acrylic acid ethyl ester,
3-[5-(2,4-Dioxo-thiazolidin-5-ylidenemethyl)-benzofuran-3-yl]-acrylic acid,
5-[3-(3-oxo-3-piperidin-1-yl-propenyl)-benzofuran-5-ylmethylene]-thiazolidine-2,4-dione,
Methyl 1-((3-{5-[(2,4-dioxo-1,3-thiazolidin-5-ylidene)methyl]-1-benzofuran-3-yl}prop-2-enoyl)prolinate,
Methyl 1-((3-{5-[(2,4-dioxo-1,3-thiazolidin-5-ylidene)methyl]-1-benzofuran-3-yl}prop-2-enoyl)-D-prolinate,
(5-({3-[(3-oxo-3-pyrrolidin-1-ylprop-1-en-1-yl]-1-benzofuran-5-yl}methylene)-1,3-thiazolidine-2,4-dione,
5-({3-[3-morpholin-4-yl-3-oxoprop-1-en-1-yl]-1-benzofuran-5-yl}methylene)-1,3-thiazolidine-2,4-dione,
Methyl 1-(3-{5-[(2,4-dioxo-1,3-thiazolidin-5-ylidene)methyl]-1-benzofuran-3-yl}prop-2-enoyl)-L-prolinate,
N-cyclohexyl-3-{5-[(2,4-dioxo-1,3-thiazolidin-5-ylidene)methyl]-1-benzofuran-3-yl)-N-methylacrylamide,
3-{5-[(2,4-dioxo-1,3-thiazolidin-5-ylidene)methyl]-1-benzofuran-3-yl}-N-ethyl-N-(2-hydroxyethyl)acrylamide,
N-cyclobutyl-3-{5-[(2,4-dioxo-1,3-thiazolidin-5-ylidene)methyl]-1-benzofuran-3-yl}acrylamide,
5-({3-[3-azetidin-1-yl-3-oxoprop-1-en-1-yl]-1-benzofuran-5-yl}methylene)-1,3-thiazolidine-2,4-dione,
5-({3-[3-(1,3-dihydro-2H-isoindol-2-yl)-3-oxoprop-1-en-1-yl]-1-benzofuran-5-yl}methylene)-1,3-thiazolidine-2,4-dione,
5-({3-[3-azepan-1-yl-3-oxoprop-1-en-1-yl]-1-benzofuran-5-yl}methylene)-1,3-thiazolidine-2,4-dione,
3-{5-[(2,4-dioxo-1,3-thiazolidin-5-ylidene)methyl]-1-benzofuran-3-yl}-N-piperidin-1-ylacrylamide,
3-{5-[(2,4-dioxo-1,3-thiazolidin-5-ylidene)methyl]-1-benzofuran-3-yl}-N-(pyridin-3-ylmethyl)acrylamide,
N-cyclohexyl-3-{5-[(2,4-dioxo-1,3-thiazolidin-5-ylidene)methyl]-1-benzofuran-3-yl}acrylamide,
5-({3-[3-(4-methylpiperazin-1-yl)-3-oxoprop-1-en-1-yl]-1-benzofuran-5-yl}methylene)-1,3-thiazolidine-2,4-dione,
N-cycloheptyl-3-{5-[(2,4-dioxo-1,3-thiazolidin-5-ylidene)methyl]-1-benzofuran-3-yl}acrylamide,
5-({3-[3-(2,5-dihydro-1H-pyrrol-1-yl)-3-oxoprop-1-en-1-yl]-1-benzofuran-5-yl}methylene)-1,3-thiazolidine-2,4-dione,
N-cyclopentyl-3-{5-[(2,4-dioxo-1,3-thiazolidin-5-ylidene)methyl]-1-benzofuran-3-yl}acrylamide,
3-[5-(2,4-Dioxo-thiazolidin-5-ylidenemethyl)-benzofuran-3-yl]-propionic acid ethyl ester,
3-[5-(2,4-Dioxo-thiazolidin-5-ylidenemethyl)-benzofuran-3-yl]-propionic acid,
5-[3-(3-oxo-3-piperidin-1-yl-propyl)-benzofuran-5-ylmethylene]-thiazolidine-2,4-dione,
6-(2,4-Dioxo-thiazolidin-5-ylidenemethyl)-2,3-dihydro-benzo[1,4]oxazine-4-carboxylic acid tert-butyl ester,
5-(3,4-Dihydro-2H-benzo[1,4]oxazin-6-ylmethylene)-thiazolidine-2,4-dione, 5-(4-Benzoyl-3,4-dihydro-2H-benzo[1,4]oxazin-6-ylm-
ethylene)-thiazolidine-2,4-dione, 5-(4-Acetyl-3,4-dihydro-2H-benzo[1,4]oxazin-6-ylmeth-
ylene)-thiazolidine-2,4-dione, 6-(2,4-Dioxo-thiazolidin-5-ylidenemethyl)-benzo[1,4]
oxazine-4-carboxylic acid tert-butyl ester,

[6-(2,4-Dioxo-thiazolidin-5-ylidenemethyl)-3-oxo-2,3-
dihydro-benzo[1,4]-oxazin-4-yl]-acetic acid methyl
ester, N-Benzyl-2-[6-(2,4-dioxo-thiazolidin-5-ylidenemethyl)-
3-oxo-2,3-dihydro-benzo[1,4]oxazin-4-yl]-acetamide, 5-(4-Butyl-3-oxo-3,4-dihydro-2H-benzo[1,4]oxazin-6-
ylmethylene)-thiazolidine-2,4-dione, 5-(4-Benzyl-3-oxo-3,4-dihydro-2H-benzo[1,4]oxazin-6-
ylmethylene)-thiazolidine-2,4-dione, 5-(2-Chloro-benzofuran-5-ylmethylene)-thiazolidine-2,
4-dione, 5-(3-Amino-benzo[d]isoxazol-5-ylmethylene)-thiazoli-
dine-2,4-dione, 5-(3-Phenylethynyl-benzofuran-5-ylmethylene)-thiazoli-
dine-2,4-dione, 5-Benzo[1,2,5]thiadiazol-5-ylmethylene-thiazolidine-2,
4-dione, 5-Benzo[1,2,5]oxadiazol-5-ylmethylene-thiazolidine-2,
4-dione, 5-(2-Methyl-benzofuran-6-ylmethylene)-thiazolidine-2,
4-dione, 5-(2-Carboxymethyl-benzofuran-6-ylmethylene)-thiazo-
lidine-2,4-dione, 5-(3-Bromo-2-fluoro-2,3-dihydro-benzofuran-6-ylmeth-
ylene)-thiazolidine-2,4-dione, and 5-(2-Fluoro-benzofuran-6-ylmethylene)-thiazolidine-2,4-
dione.

20. A method of preparing a medicament, comprising, contacting the thiazolidinone-vinyl fused-benzene according to claim 13, with one or more pharmaceutically acceptable additives.

21. A pharmaceutical composition, comprising at least one thiazolidinone-vinyl fused-benzene according to claim 13, and a pharmaceutically acceptable carrier, diluent or excipient thereof.

22. A method for the treatment of inflammation, the method comprising administering to a subject in need thereof, an effective amount of the thiazolidinone-vinyl fused-benzene according to claim 13.

23. A method of preparing a thiazolidinone-vinyl fused-benzene of formula (II), according to claim 14, comprising the following step:

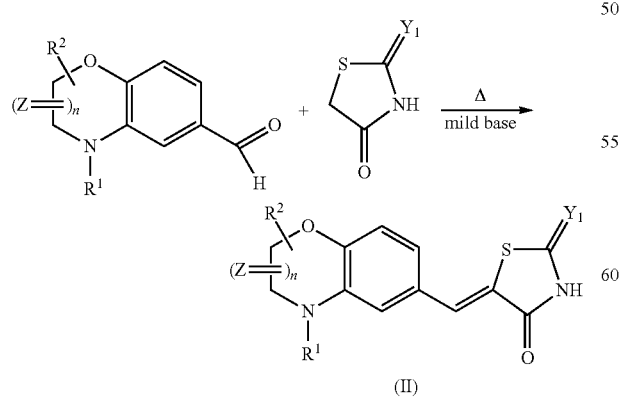

wherein $R^1$, $R^2$, $Y^1$, Z and n are as above defined in formula (II).

24. A method of preparing a thiazolidinone-vinyl fused-benzene of formula (III), according to claim 17, comprising the following step:

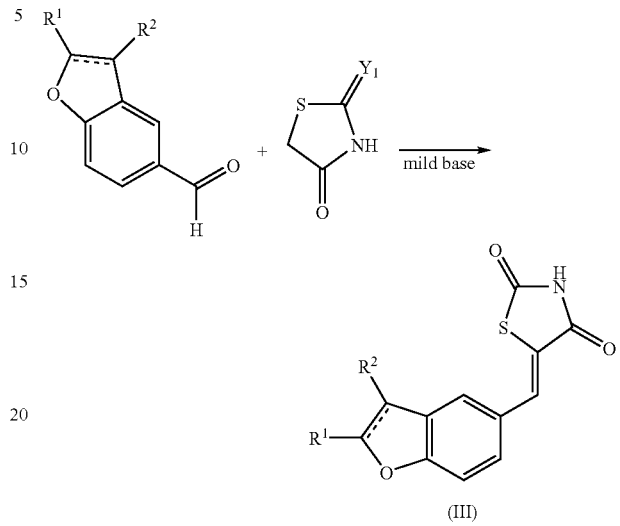

wherein $R^1$, $R^2$ are as above defined for formula (III), and $Y^1$ is O, S or NH.

25. A composition, comprising, a pharmaceutically acceptable carrier, diluent or excipient and at least one compound according to formula (I):

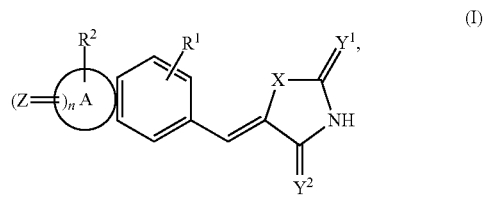

as well as its geometrical isomers, its optically active forms as enantiomers, diastereomers and its racemate forms, as well as pharmaceutically acceptable salts thereof, wherein A is a 5-8 membered heterocyclic group;

X is S or O;

$Y^1$ and $Y^2$ are independently S or O;

Z is S or O;

$R^1$ is H, CN, carboxy, acyl, $C_1$-$C_6$-alkoxy, halogen, hydroxy, acyloxy, $C_1$-$C_6$-alkyl carboxy, $C_1$-$C_6$-alkyl acyloxy, alkoxy, alkoxycarbonyl, $C_1$-$C_6$-alkyl alkoxycarbonyl, aminocarbonyl, $C_1$-$C_6$-alkyl aminocarbonyl, acylamino, $C_1$-$C_6$-alkyl acylamino, ureido, $C_1$-$C_6$-alkyl ureido, amino, $C_1$-$C_6$-alkyl amino, ammonium, sulfonyloxy, $C_1$-$C_6$-alkyl sulfonyloxy, sulfonyl, sulfonyl, sulfinyl, $C_1$-$C_6$-alkyl sulfinyl, sulfanyl, $C_1$-$C_6$-alkyl sulfanyl, sulfonylamino, $C_1$-$C_6$-alkyl sulfonylamino or carbamate;

$R^2$ is selected from the group consisting of H, halogen, acyl, amino, $C_1$-$C_6$-alkyl, $C_2$-$C_6$-alkenyl, $C_2$-$C_6$-alkynyl, $C_1$-$C_6$-alkyl carboxy, $C_1$-$C_o$-alkyl acyl, $C_1$-$C_o$-alkyl alkoxycarbonyl, $C_1$-$C_6$-alkyl aminocarbonyl, $C_1$-$C_6$-alkyl acyloxy, $C_1$-$C_6$-alkyl acylamino, $C_1$-$C_6$-alkyl ureido, $C_1$-$C_6$-alkyl amino, $C_1$-$C_6$-alkyl alkoxy, $C_1$-$C_6$-alkyl sulfanyl, $C_1$-$C_6$-alkyl sulfinyl, $C_1$-$C_6$-alkyl sulfonyl, $C_1$-$C_6$-alkyl sulfonylaminoaryl, aryl, $C_3$-$C_8$-cycloalkyl or heterocycloalkyl, $C_1$-$C_o$-alkyl aryl, $C_2$-$C_6$-alkenyl-aryl, $C_2$-$C_6$-alkynyl aryl, carboxy, cyano, hydroxy, $C_1$-$C_6$-alkoxy, nitro, acylamino, ureido, $C_1$-$C_6$-alkyl carbamate, sulfonylamino, sulfanyl, or sulfonyl;
n is 0, 1 or 2;
with the proviso that the following compounds are excluded:
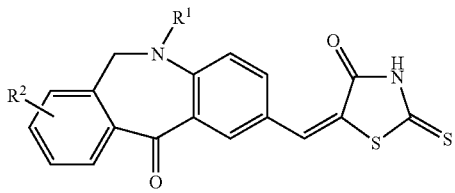
(TE)
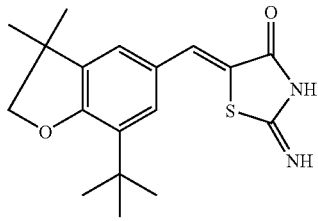
(JA)
wherein $R^1$ is a lower alkyl or aralkyl and $R^2$ is H or a halogen.
* * * * *